(12) United States Patent
Bade et al.

(10) Patent No.: US 10,907,125 B2
(45) Date of Patent: Feb. 2, 2021

(54) FLOW THROUGH ELECTROPORATION MODULES AND INSTRUMENTATION

(71) Applicant: Inscripta, Inc., Boulder, CO (US)

(72) Inventors: Nathan Bade, Boulder, CO (US); Jorge Bernate, Boulder, CO (US); Phillip Belgrader, Pleasanton, CA (US); Don Masquelier, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 16/904,386

(22) Filed: Jun. 17, 2020

(65) Prior Publication Data

US 2020/0399579 A1 Dec. 24, 2020

Related U.S. Application Data

(60) Provisional application No. 62/964,203, filed on Jan. 22, 2020, provisional application No. 62/864,368, filed on Jun. 20, 2019.

(51) Int. Cl.
*C12M 1/42* (2006.01)
*C12M 1/00* (2006.01)

(52) U.S. Cl.
CPC ............ *C12M 35/02* (2013.01); *C12M 29/04* (2013.01)

(58) Field of Classification Search
None
See application file for complete search history.

(56) References Cited

U.S. PATENT DOCUMENTS

| | | |
|---|---|---|
| 5,710,381 A | 1/1998 | Atwood et al. |
| 5,792,943 A | 8/1998 | Craig |
| 6,074,605 A | 6/2000 | Meserol et al. |
| 6,127,141 A | 10/2000 | Kopf |
| 6,150,148 A | 11/2000 | Nanda et al. |
| 6,482,619 B1 | 11/2002 | Rubinsky et al. |
| 6,654,636 B1 | 11/2003 | Dev et al. |
| 6,746,441 B1 | 6/2004 | Hofmann et al. |
| 6,837,995 B1 | 1/2005 | Vassarotti et al. |
| 7,029,916 B2 | 4/2006 | Dzekunov et al. |
| 7,141,425 B2 | 11/2006 | Dzekunov et al. |
| 7,166,443 B2 | 1/2007 | Walker et al. |
| 7,422,889 B2 | 9/2008 | Sauer et al. |

(Continued)

FOREIGN PATENT DOCUMENTS

| | | |
|---|---|---|
| EP | 2135626 | 1/2011 |
| EP | 1766004 | 8/2016 |

(Continued)

OTHER PUBLICATIONS

Pudasaini et al., "Continuous flow microfluidic cell inactivation with the use of insulating micropillars for multiple electroporation zones". Electrophoresis, vol. 40 (Jun. 8, 2019), Issues 18-19, pp. 2522-2529. (Year: 2019).*

(Continued)

*Primary Examiner* — William H. Beisner
(74) *Attorney, Agent, or Firm* — Sarah Brashears; Dianna L. DeVore

(57) ABSTRACT

The present disclosure provides a flow-through electroporation device configured for use in an automated multi-module cell processing environment and configured to decrease cell processing time and the risk of clogging.

19 Claims, 38 Drawing Sheets

(56) References Cited

U.S. PATENT DOCUMENTS

| | | |
|---|---|---|
| 8,110,112 B2 | 2/2012 | Alburty et al. |
| 8,153,432 B2 | 4/2012 | Church et al. |
| 8,569,041 B2 | 10/2013 | Church et al. |
| 8,584,535 B2 | 11/2013 | Page et al. |
| 8,584,536 B2 | 11/2013 | Page et al. |
| 8,667,839 B2 | 3/2014 | Kimura |
| 8,667,840 B2 | 3/2014 | Lee et al. |
| 8,677,839 B2 | 3/2014 | Page et al. |
| 8,677,840 B2 | 3/2014 | Page et al. |
| 8,697,359 B1 | 4/2014 | Zhang et al. |
| 8,726,744 B2 | 5/2014 | Alburty et al. |
| 8,758,623 B1 | 6/2014 | Alburty et al. |
| 8,932,850 B2 | 1/2015 | Chang et al. |
| 9,029,109 B2 | 5/2015 | Hur et al. |
| 9,063,136 B2 | 6/2015 | Talebpour et al. |
| 9,534,989 B2 | 1/2017 | Page et al. |
| 9,546,350 B2 | 1/2017 | Dzekunov et al. |
| 9,593,359 B2 | 3/2017 | Page et al. |
| 9,738,918 B2 | 8/2017 | Alburty et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 10,017,760 B2 | 7/2018 | Gill et al. |
| 2002/0139741 A1 | 10/2002 | Kopf |
| 2003/0059945 A1 | 3/2003 | Dzekunov et al. |
| 2003/0073238 A1 | 4/2003 | Dzekunov et al. |
| 2003/0104588 A1 | 6/2003 | Orwar et al. |
| 2004/0115784 A1 | 6/2004 | Dzekunov et al. |
| 2004/0171156 A1 | 9/2004 | Hartley et al. |
| 2005/0064584 A1 | 3/2005 | Bargh |
| 2005/0118705 A1 | 6/2005 | Rabbitt et al. |
| 2006/0001865 A1 | 1/2006 | Bellalou et al. |
| 2006/0224192 A1 | 10/2006 | Dimmer et al. |
| 2007/0042427 A1 | 2/2007 | Gerdes et al. |
| 2007/0105206 A1 | 5/2007 | Lu et al. |
| 2007/0231873 A1 | 10/2007 | Ragsdale |
| 2007/0249036 A1 | 10/2007 | Ragsdale et al. |
| 2008/0138877 A1 | 6/2008 | Dzekunov et al. |
| 2010/0055790 A1 | 3/2010 | Simon |
| 2010/0076057 A1 | 3/2010 | Sontheimer et al. |
| 2011/0002812 A1 | 1/2011 | Asogawa et al. |
| 2011/0003303 A1 | 1/2011 | Pagano et al. |
| 2011/0009807 A1 | 1/2011 | Kjeken et al. |
| 2011/0065171 A1 | 3/2011 | Dzekunov et al. |
| 2011/0189650 A1* | 8/2011 | Ayliffe .................. C12M 47/04 435/3 |
| 2011/0213288 A1 | 9/2011 | Choi et al. |
| 2011/0236962 A1 | 9/2011 | Loebbert et al. |
| 2012/0156786 A1 | 6/2012 | Bebee |
| 2013/0005025 A1 | 1/2013 | Church et al. |
| 2013/0015119 A1 | 1/2013 | Pugh et al. |
| 2013/0196441 A1 | 8/2013 | Rubinsky et al. |
| 2014/0068797 A1 | 3/2014 | Doudna et al. |
| 2014/0121728 A1 | 5/2014 | Dhillon et al. |
| 2014/0199767 A1 | 7/2014 | Barrangou et al. |
| 2014/0273226 A1 | 9/2014 | Wu et al. |
| 2014/0350456 A1 | 11/2014 | Caccia |
| 2015/0072413 A1 | 3/2015 | Zenhausern et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0297887 A1 | 10/2015 | Dhillon et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0168592 A1 | 6/2016 | Church et al. |
| 2016/0272961 A1 | 9/2016 | Lee |
| 2016/0281047 A1 | 9/2016 | Chen et al. |
| 2016/0289673 A1 | 10/2016 | Huang et al. |
| 2016/0298074 A1 | 10/2016 | Dai |
| 2016/0298134 A1 | 10/2016 | Chen et al. |
| 2016/0310943 A1 | 10/2016 | Woizenko et al. |
| 2016/0313306 A1 | 10/2016 | Ingber et al. |
| 2016/0367991 A1 | 12/2016 | Cepheid |
| 2017/0002339 A1 | 1/2017 | Barrangou et al. |
| 2017/0029805 A1 | 2/2017 | Li et al. |
| 2017/0051310 A1 | 2/2017 | Doudna et al. |
| 2017/0073705 A1 | 3/2017 | Chen et al. |
| 2017/0218355 A1 | 3/2017 | Buie et al. |
| 2017/0159045 A1 | 6/2017 | Serber et al. |
| 2017/0191123 A1 | 7/2017 | Kim et al. |
| 2017/0233692 A1* | 8/2017 | Pawell ..................... B81B 1/00 435/455 |
| 2017/0240922 A1 | 8/2017 | Gill et al. |
| 2017/0283761 A1 | 10/2017 | Corso |
| 2017/0307606 A1 | 10/2017 | Hallock |
| 2017/0349874 A1 | 12/2017 | Jaques et al. |
| 2018/0023045 A1 | 1/2018 | Hallock et al. |
| 2018/0051327 A1 | 2/2018 | Blainey et al. |
| 2018/0142196 A1 | 5/2018 | Coppeta et al. |
| 2018/0155665 A1 | 6/2018 | Zenhausern et al. |
| 2018/0169148 A1 | 6/2018 | Adair et al. |
| 2018/0179485 A1 | 6/2018 | Borenstein et al. |
| 2019/0136224 A1 | 5/2019 | Garcia Dominquez et al. |

FOREIGN PATENT DOCUMENTS

| | | |
|---|---|---|
| EP | 2459696 | 11/2017 |
| WO | WO 2003/057819 | 7/2001 |
| WO | WO 2009/091578 | 7/2009 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO 2015/021270 | 2/2015 |
| WO | WO 2016/003485 | 1/2016 |
| WO | WO 2016/054939 | 4/2016 |
| WO | WO 2016/145290 | 9/2016 |
| WO | WO 2018/015544 | 1/2018 |
| WO | WO 2018/191715 | 10/2018 |
| WO | WO 2012/012779 | 1/2019 |

OTHER PUBLICATIONS

Bao, et al., "Genome-scale engineering of *Saccharomyces cerevisiae* with single-nucleotide precision", Nature Biotechnology, doi:10.1038/nbt.4132, pp. 1-6 (May 7, 2018).

Dicarlo, et al., "Genome engineering in *Saccharomyces cervisiae* using CRISPR-Case systems", Nucleic Acids Research, 41(7):4336-43 (2013).

Garst, et al., "Genome-wide mapping of mutations at single-nucleotide resolution for protein, metabolic and genome engineering", Nature Biotechnology, 35(1):48-59 (2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Verwaal, et al., "CRISPR/Cpf1 enables fast and simple genome editing of *Saccharamyces cerevisiae*", Yeast, 35:201-11 (2018).

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).

Roy, et cl., "Multiplexed precision genome editing with trackable genomic barcodes in yeast", Nature Biotechnolgy, doi:10.1038/nbt.4137, pp. 1-16 (2018).

Dong, "Establishment of a highly efficient virus-inducible CRISPR/Cas9 system in insect cells," Antiviral Res., 130:50-7(2016).

Epinat et al., "A novel engineered meganuclease induces homologous recombination in eukaryotic cells, e.g., yeast and mammalian cells", Nucleic Acids Research, 31(11): 2952-2962.

Farasat et al., "A Biophysical Model of CRISPR/Cas9 Activity for Rational Design of Genome Editing and Gene Regulation," PLoS Comput Biol., 29:12(1):e1004724 (2016).

(56) References Cited

OTHER PUBLICATIONS

Liu et al., "A chemical-inducible CRISPR-Cas9 system for rapid control of genome editing", Nature Chemical Biology, 12:980-987(2016).
Adamo, et al., "Flow-through comb electroporation device for delivery of macromolecules", Analytical Chemistry, 85(3):1637-41 (2015).
International Search Report and Written Opinion for International Application No. PCT/US2018/040519, dated Sep. 26, 2018, p. 1-8.
International Search Report and Written Opinion for International Application No. PCT/US2018/053670, dated Jan. 3, 2019, p. 1-13.
International Search Report and Written Opinion for International Application No. PCT/US2018/053671, dated Nov. 23, 2018, p. 1-12.
International Search Report and Written Opinion for International Application No. PCT/US2019/023342, dated Jun. 6, 2019, p. 1-12.
International Search Report and Written Opinion for International Application No. PCT/US2019/026836, dated Jul. 2, 2019, p. 1-10.
International Search Report and Written Opinion for International Application No. PCT/US2019/030085, dated Jul. 23, 2019, p. 1-14.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication for U.S. Appl. No. 16/024,831, dated Feb. 12, 2019, p. 1-37.
NonFinal Office Action for U.S. Appl. No. 16/399,988, dated Jul. 31, 2019, p. 1-20.
First Office Action Interview Pilot Program Pre-Interview Communication for U.S. Appl. No. 16/454,865 dated Aug. 16, 2019, p. 1-36.
International Search Report and Written Opinion for International Application No. PCT/US2018/053608, dated Dec. 13, 2018, p. 1-9.
International Search Report and Written Opinion for International Application No. PCT/US19/46515, dated Oct. 28, 2019, p. 1-11.
International Search Report and Written Opinion for International Application No. PCT/US19/49735, dated Nov. 18, 2019, p. 1-13.

* cited by examiner

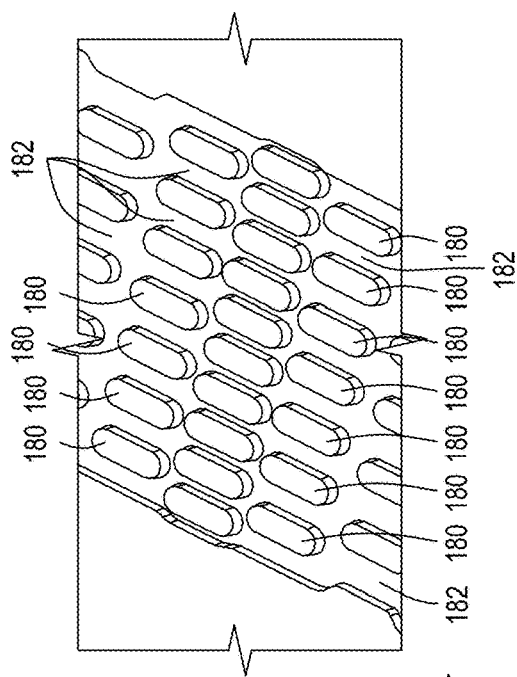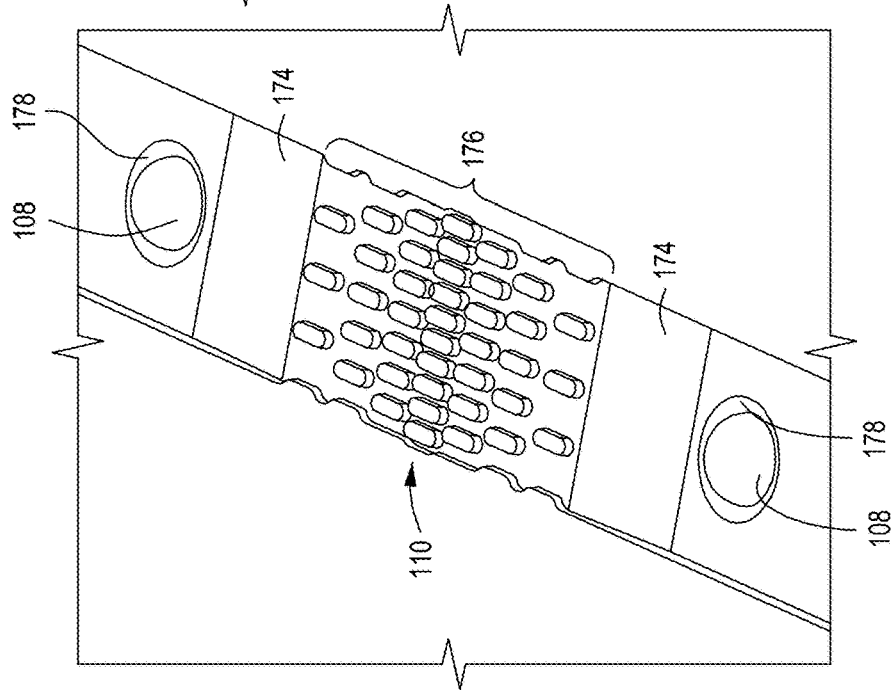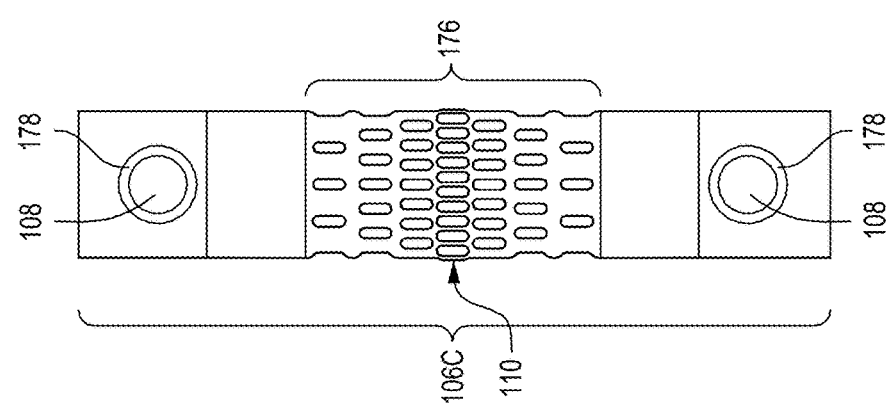

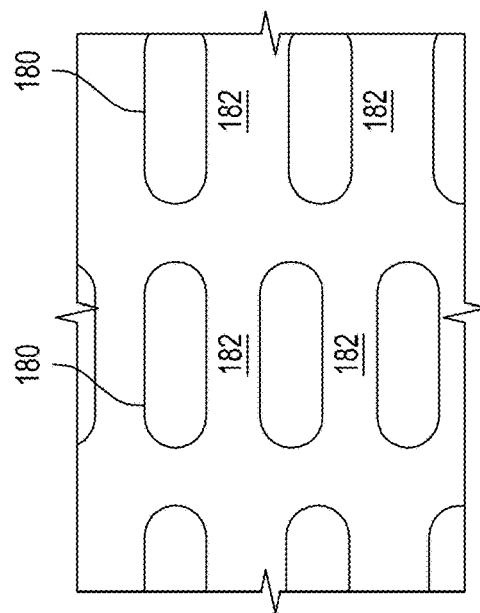
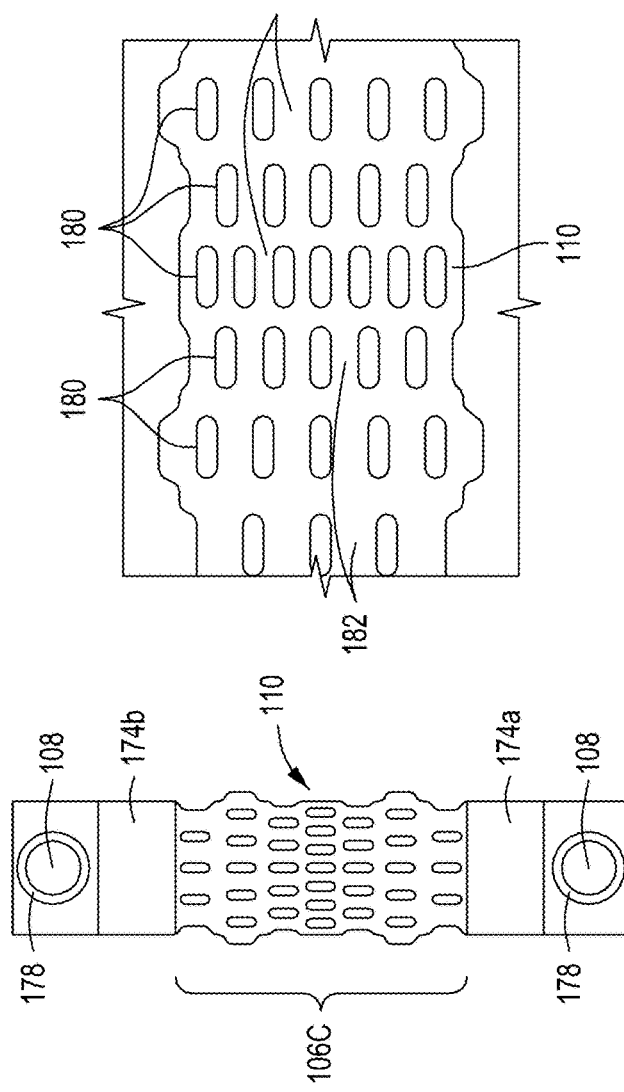

| 240 → | A | B | C | D |
|---|---|---|---|---|
| 1 | 210 | 214 | 218 | 222 |
| 2 | 211 | 215 | 219 | 223 |
| 3 | 212 | 216 | 220 | 224 |
| 4 | 213 | 217 | 221 | 225 |

FLOW THROUGH ELECTROPORATION MODULES AND INSTRUMENTATION

RELATED CASES

The present application claims priority to U.S. Ser. No. 62/864,368, filed 20 Jun. 2019, entitled "Flow Through Electroporation Modules and Instrumentation"; and U.S. Ser. No. 62/964,203, filed 22 Jan. 2020, entitled "Flow Through Electroporation Modules and Instrumentation", both of which are incorporated herein in their entirety.

FIELD OF THE INVENTION

The present disclosure relates to flow-through electroporation devices configured as stand-alone electroporation modules or as one module in automated multi-module cell processing instruments.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The cell membrane constitutes the primary barrier for the transport of molecules and ions between the interior and the exterior of a cell. Electroporation, also known as electropermeabilization, substantially increases cell membrane permeability in the presence of a pulsed electric field. Traditional electroporation systems have been widely used; however, traditional systems require high current input and suffer from adverse environmental conditions such as electric field distortion, local pH variation, metal ion dissolution and excess heat generation, all of which may contribute to low electroporation efficiency and/or cell viability. Further, traditional electroporation systems are not easily automated or incorporated into automated cell processing systems where electroporation is but one process of many processes performed. There is thus a need for automated multi-module cell processing systems and components thereof capable of transforming multiple cells in an efficient and automated fashion. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides an electroporation device configured both for use as a stand-alone electroporation device and for use in an automated multi-module cell processing environment. The electroporation device utilizes a microfluidic flow-through configuration that facilitates continuous processing of cell suspensions. By decreasing the cross-sectional area of paths or lanes of fluid flow in the flow channel between electrodes and adjusting the pressure driving the fluid flow through the device, the electric field strength experienced by cells can be made sufficiently high with a desired duration of poration to porate the plasma membrane. The narrow flow channels are parallelized to decrease processing time and reduce the chance of catastrophic failure due to clogging.

In certain embodiments, there is provided a flow-through electroporation (FTEP) device for introducing an exogenous material into cells in a fluid, the FTEP device comprising: an inlet and an inlet channel for receiving a fluid comprising cells and/or exogenous material into the FTEP device; an outlet and an outlet channel for removing a fluid comprising transformed cells and exogenous material from the FTEP device; a flow channel intersecting and positioned between the inlet channel and the outlet channel, wherein the flow channel has, moving from the inlet channel toward the outlet channel, an inlet-filter region, an inlet-proximal region, a central region, an outlet-proximal region, and an outlet-filter region; an inlet filter comprising filter elements disposed in the inlet-filter region of the flow channel and an outlet filter comprising filter elements disposed in the outlet-filter region of the flow channel; a plurality of obstructions defining flow paths disposed within the central region of the flow channel; and a first and a second electrode positioned in electrode channels, wherein the first electrode is positioned in the inlet proximal region of the flow channel and the second electrode is positioned in the outlet proximal region of the flow channel; wherein the electrodes are positioned perpendicularly to the flow channel, are in fluid and electrical communication with fluid in the flow channel, and wherein the electrodes apply one or more electric pulses to the cells in the fluid as they pass through the flow channel, thereby introducing exogenous material into the cells in the fluid.

In some aspects of this embodiment, the plurality of obstructions defining flow paths disposed within the central region of the flow channel increase in density from the inlet proximal region of the flow channel to a central portion of the central region and decrease in density from the central portion of the central region to the outlet proximal region of the flow channel.

In some aspects of this embodiment, the FTEP device further comprises a reservoir coupled to the inlet for introducing the cells in fluid into the FTEP device and a reservoir coupled to the outlet for removing transformed cells from the FTEP device, and in some aspects, the FTEP device comprises a second inlet and a second inlet channel and further comprises a reservoir coupled to the second inlet for introducing exogenous material into the FTEP device. In some configurations, the second inlet and second inlet channel are located between the inlet channel and the first electrode, and in alternative configurations the second inlet and second inlet channel are located between the first electrode and the central region.

In some aspects, elongated obstructions may be arranged in a parallel configuration, and in some aspects, peg-like obstructions may be arranged in rows.

The FTEP devices described herein are configured for use with bacterial, yeast and mammalian cells.

In some aspects, the number of obstructions in the central region of the flow channel is from 5 to 100, and in other aspects, the number of obstructions in the central region of the flow channel is from 6 to 80, 7 to 60 or 8 to 40.

In some aspects, the inlet filter region comprises an inlet filter comprising filter elements disposed in the inlet-filter region of the flow channel, wherein the inlet filter elements comprise triangular-, square-, rectangular-, pentagonal-, hexagonal-, oval-, or elliptical-shaped elements.

In some aspects, the outlet filter region comprises an outlet filter comprising filter elements disposed in the outlet-filter region of the flow channel, wherein the outlet filter elements comprise elongated oval-, triangular-, square-, rectangular-, pentagonal-, hexagonal-, oval-, or elliptical-shaped elements.

In some aspects, the narrowest flow path between obstructions is from 10 μm to 350 μm wide, and in other aspects, narrowest flow path between obstructions is from 30 μm to 250 μm wide.

In some aspects, the obstructions are triangular-, square-, rectangular-, pentagonal-, hexagonal-, oval-, or elliptical-shaped obstructions, or a combination of two or more shaped obstructions.

In many aspects, there is presented herein an automated multi-module cell processing instrument comprising the FTEP devices described herein.

In some aspects, the FTEP device demonstrates optimal uptake at 6.8 psi and 3 kV and recapitulates a rectangular pulse and residence time similar to a cuvette system.

In some aspects of the FTEP device, the electrodes supply a voltage of 1-25 kV/cm, and in some aspects, the electrodes supply a voltage of 5-60 kV/cm, or 10-50 kV/cm, or 20-40 kV/cm.

In some aspects, the flow through the FTEP device is from 0.01 mL/min to 7.5 mL/min and the pressure in the FTEP is from 1-30 psi, or from 2-10 psi. In some aspects, the FTEP is from 3-15 cm long, or from 4-12 cm long, and from 0.5 to 5 cm wide.

In some aspects, the FTEP device further comprises a ramp in the central region proximal to the inlet-proximal region of the flow channel extending to a central portion of the central region, wherein the flow channel height decreases at the central portion, and a ramp from the central portion of the central region to the central region proximal to the outlet-proximal region of the flow channel wherein the flow channel height increases at the outlet-proximal region. In some aspects, the FTEP device further comprises steps instead of ramps wherein the decrease in channel height from the inlet-proximal region to the central region and the increase in channel height from the central region to the outlet-proximal region is an abrupt step rather than a ramp.

These aspects and other features and advantages of the invention are described below in more detail.

BRIEF DESCRIPTION OF THE DRAWINGS

The foregoing and other features and advantages of the present disclosure will be more fully understood from the following detailed description of illustrative embodiments taken in conjunction with the accompanying drawings in which:

FIG. 1F-1H are representations of an obstruction array and individual obstruction structures. FIGS. 1I-1K are representations of an obstruction array and individual obstruction structures. FIG. 1O depicts (i) electrodes arrayed on an electrode platform before insertion into an FTEP assembly; (ii) an electrode; and (iii) the electrode inserted into an electrode channel with the electrode and electrode channel adjacent to the flow channel.

It should be understood that the drawings are not necessarily to scale, and that like reference numbers refer to like features.

DETAILED DESCRIPTION

Figure 1A:
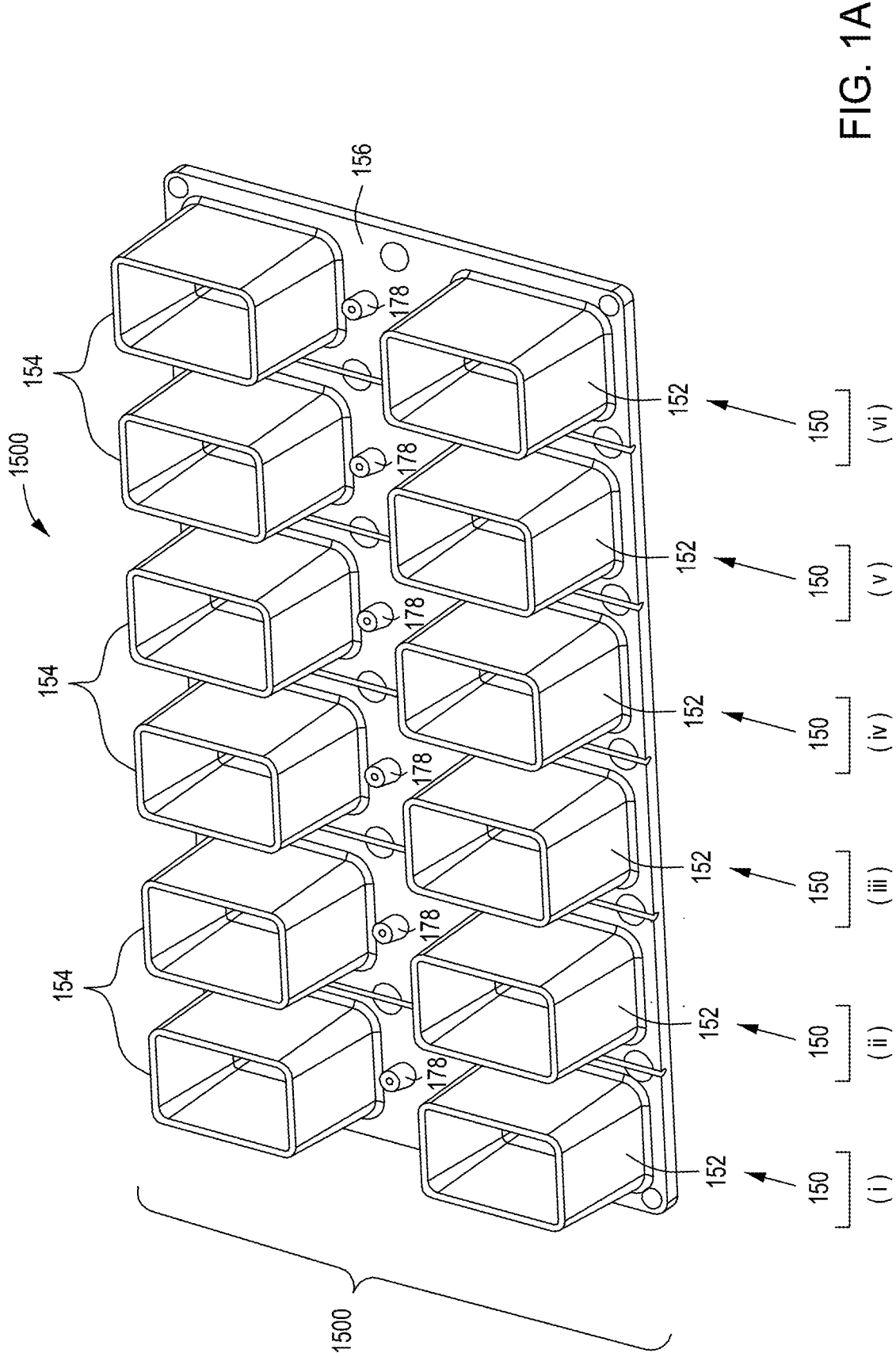
FIGS. 1A through 1C are top perspective, bottom perspective, and bottom views, respectively, of a flow-through electroporation device assembly.

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual*. 4th, ed., Cold Spring Harbor Laboratory Press, Cold Spring Harbor, N.Y., (2014); *Current Protocols in Molecular Biology*, Ausubel, et al. eds., (2017); Neumann, et al., *Electroporation and Electrofusion in Cell Biology*, Plenum Press, New York, 1989; and Chang, et al., *Guide to Electroporation and Electrofusion*, Academic Press, California (1992), all of which are herein incorporated in their entirety by reference for all purposes. Nucleic acid-guided nuclease techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," and/or "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Additionally, the terms "approximately," "proximate," "minor," and similar terms generally refer to ranges that include the identified value within a margin of 20%, 10% or preferably 5% in certain embodiments, and any values therebetween.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components-translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell-will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

As used herein, "enrichment" refers to enriching for edited cells by singulation, optionally inducing editing, and growth of singulated or substantially singulated cells into terminal-sized colonies (e.g., saturation or normalization of colony growth). Alternatively, "enrichment" may be performed on a bulk liquid culture, by inducing editing when the cells are at the end of the logarithmic stage of growth or just after the cells enter growth senescence. Inducing editing entails inducing transcription of the nuclease, gRNA or both.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible, and in some embodiments-particularly many embodiments in which enrichment is employed—the transcription of at least one component of the nucleic acid-guided nuclease editing system is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, rifampicin, puromycin, hygromycin, blasticidin, and G418 may be employed. In other embodiments, selectable markers include, but are not limited to sugars such as rhamnose, human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, in a nucleic acid (e.g., genome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, YACs, BACs, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto. Engine vectors also typically comprise a selectable marker. As used herein the phrase "editing vector" comprises a donor nucleic acid, optionally including an alteration to the target sequence that prevents nuclease binding at a PAM or spacer in the target sequence after editing has taken place, and a coding sequence for a gRNA. The editing vector may also comprise a selectable marker and/or a barcode. In some embodiments, the engine vector and editing vector may be combined; that is, all editing and selection components may be found on a single vector. Further, the engine and editing vectors comprise control sequences operably linked to, e.g., the nuclease coding sequence, recombineering system coding sequences (if present), donor nucleic acid, guide nucleic acid, and selectable marker(s).

The Invention Generally

Electroporation is a widely-used method for permeabilization of cell membranes that works by temporarily generating pores in the cell membranes with electrical stimulation. The applications of electroporation include the delivery of DNA, RNA, siRNA, peptides, proteins, antibodies, drugs or other substances to a variety of cells such as mammalian cells (including human cells), plant cells, archaea, yeasts, other eukaryotic cells, bacteria, and other cell types. Further, mixtures of cell types can also be electroporated in a single run; e.g., mixtures of E. coli strains, mixtures of bacterial strains, mixtures of yeast strains, mixtures of mammalian cells. Electrical stimulation may also be used for cell fusion in the production of hybridomas or other fused cells. During a typical electroporation procedure, cells are suspended in a buffer or medium that is favorable for cell survival. For bacterial cell electroporation, low conductance mediums, such as water, glycerol solutions and the like, are often used to reduce the heat production by transient high current. The cells and material to be electroporated into the cells (collectively "the cell sample") is then placed in a cuvette embedded with two flat electrodes for an electrical discharge. For example, Bio-Rad (Hercules, Calif.) makes the GENE PULSER XCELL™ line of products to electroporate cells in cuvettes. Traditionally, electroporation requires high field strength.

Generally speaking, microfluidic flow-through electroporation (FTEP)—using cell suspension volumes of less than approximately 10 ml and as low as 1 μl—allows for more precise control over the transfection or transformation process and permits flexible integration with other cell processing tools compared to bench-scale electroporation devices. Microfluidic flow-through electroporation thus provides unique advantages for, e.g., single cell transformation, processing, and analysis; microfluidic electroporation may be used for multi-unit FTEP device configurations; and microfluidic electroporation devices may be integrated into automated multi-module cell processing instruments.

A particular characteristic of the FTEP devices disclosed herein is that rather than having a single flow path for the cells to be porated, the FTEP devices described herein have a single flow channel but many flow paths. The flow channel comprises obstructions or flow diverters such that the single flow channel is separated or parallelized into many flow paths. Configuring the flow channel into many flow paths provides the advantage that if one flow path becomes clogged, there are several to many alternative flow paths that may be taken. That is, if only a single flow path is present and this single flow path is clogged or obstructed, the result is a catastrophic failure of the electroporation device. Further, at constant applied voltage, electric field strength can be increased by reducing the spacing between the obstructions in the obstruction array. Thus, as the spacing between obstructions gets smaller, the electric field increases and thus the efficiency of electroporation of the cells increases.

The present disclosure provides FTEP devices, automated multi-module instruments and methods of using FTEP devices that achieve high efficiency cell electroporation with low toxicity where the electroporation devices and systems can be integrated with other automated cell processing tools. Further, the electroporation device of the disclosure allows for multiplexing where two to many electroporation units are constructed and used in parallel, which allows for particularly easy integration with robotic liquid handling instrumentation. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

During the electroporation process, it is important to use voltage sufficient for achieving electroporation of material into the cells, but not too much voltage as too much power will decrease cell viability. For example, to electroporate a suspension of a human cell line, 200 volts is needed for a 0.2 ml sample in a 4 mm-gap cuvette with exponential discharge from a capacitor of about 1000 μF. However, if the same 0.2 ml cell suspension is placed in a longer container with 2 cm electrode distance (5 times of cuvette gap distance), the voltage required would be 1000 volts, but a capacitor of only 40 μF (1/25 of 1000 μF) is needed because the electric energy from a capacitor follows the equation of:

$$E=0.5U^2C$$

where E is electric energy, U is voltage and C is capacitance. Therefore, a high voltage pulse generator is easy to manufacture because it needs a much smaller capacitor to store a similar amount of energy. Similarly, it would not be difficult to generate other wave forms of higher voltages.

The electroporation devices of the disclosure allow for a high rate of cell transformation in a relatively short amount of time. The rate of cell transformation is dependent on the cell type and the number of cells being transformed. For example, for E. coli, the electroporation devices can provide a cell transformation rate of $10^3$ to $10^{12}$ cells per minute, $10^4$ to $10^{10}$ per minute, $10^5$ to $10^9$ per minute, or $10^6$ to $10^8$ per minute. Typically, $10^7$ to $10^8$ yeast cells are subjected to transformation and $10^4$ to $10^5$ are transformed per round of transformation, and $10^9$-$10^{10}$ bacterial are subjected to transformation and $10^6$ to $10^7$ are transformed per round of transformation. The electroporation devices also allow transformation of batches of cells ranging from 1 cell to $10^{11}$ cells in a single transformation procedure using parallel devices.

Exemplary FTEP Embodiments

Figure 1B:
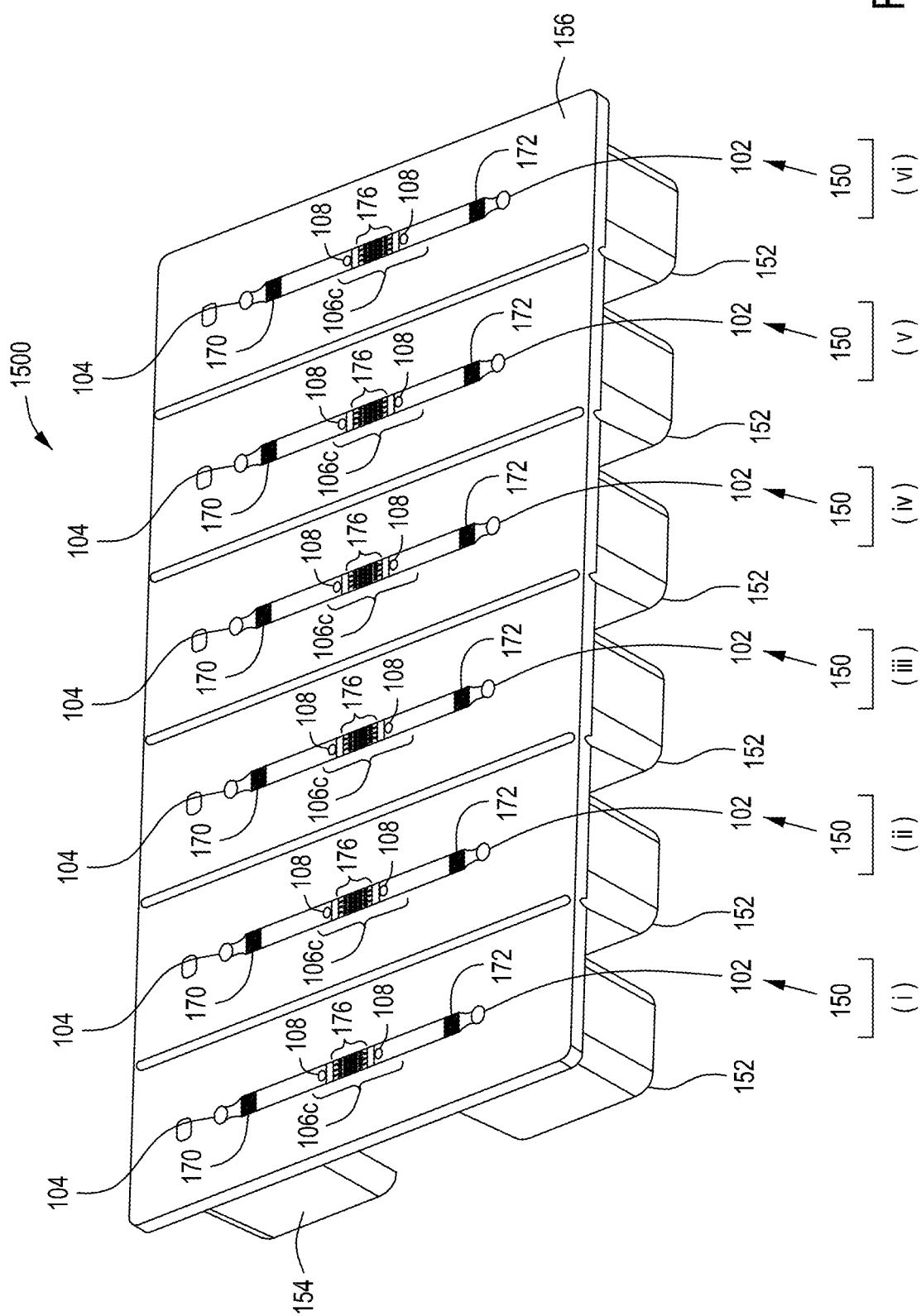
Figure 1C:
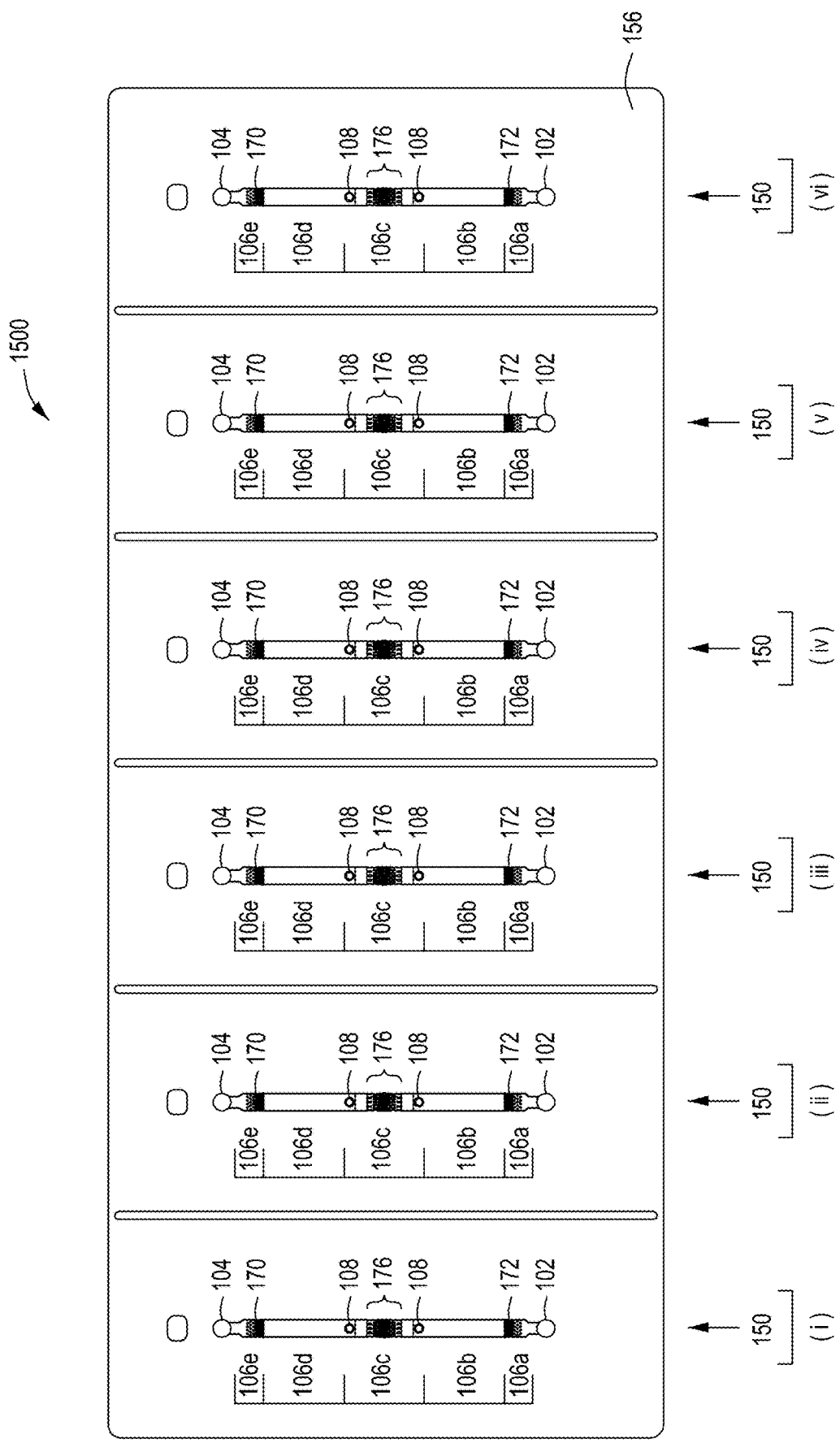

An FTEP assembly is illustrated in FIGS. 1A-1C. FIGS. 1A through 1C are top perspective, bottom perspective, and bottom views, respectively, of an FTEP assembly 1500 comprising six co-joined FTEP devices 150. FIG. 1A depicts six FTEP units 150 arranged on a single, integrally-formed injection molded substrate 156. Each of the six FTEP units 150 have wells 152 that define inlets and wells 154 that define outlets. Further, on each FTEP unit one of two electrode channels 178 can be seen. FIG. 1B is a bottom perspective view of the FTEP assembly 1500 with the six co-joined FTEP devices 150 of FIG. 15A arranged on a single substrate 156. Six inlet wells 152 can be seen, one for each flow-through electroporation unit 150, and one outlet well 154 can be seen on the left-most FTEP unit. Also seen in FIG. 1B for each FTEP unit 150 are an inlet 102, an outlet 104, a flow channel 106 comprising five regions: an inlet-filter region 106a, an inlet-proximal region 106b, a central region 106c, an outlet-proximal region 106d, and an outlet-filter region 106e (only central region 106c is labeled in this FIG. 1B, but see FIG. 1C). Each FTEP unit further comprises two electrodes 108 flanking central region 106c of flow channel 106. Central region 106c of flow channel 106 comprises a central portion (not labeled) comprising an obstruction array 176 that includes a plurality of obstructions (not seen clearly in this FIG. 1B) which provide several to many paths for cells to travel through flow channel 106. Additionally seen are filters 172 and 170 included in the inlet-filter region 106a and outlet-filter region 106e, respectively, of flow channel 106 to prevent clogging in flow channel 106.

FIG. 1C is a bottom view of the FTEP assembly 1500 of the six co-joined FTEP devices 150 of FIGS. 1A and 1B. Depicted in FIG. 1C are six FTEP units 150 arranged on a single substrate 156, where each FTEP unit 150 comprises an inlet 102, an outlet 104, a flow channel 106 comprising five regions: an inlet-filter region 106a, an inlet-proximal region 106b, a central region 106c, an outlet-proximal region 106d, and an outlet-filter region 106e. Each FTEP unit further comprises two electrodes 108 flanking the central region 106c of flow channel 106. Central region 106c of flow channel 106 comprises a central portion comprising an obstruction array 176 that includes a plurality of obstructions (not seen clearly in this FIG. 1C) which provide a number of flow paths for cells travelling through flow channel 106. Additionally seen are filters 172 and 170 included in the inlet-filter region 106a and outlet-filter region 106e, respectively, of flow channel 106 to prevent clogging of the channel. Once the six FTEP units 150 are fabricated, they can be separated from one another (e.g., "snapped apart") upon the depicted score lines and used one at a time; alternatively, the FTEP units may be used in embodiments where two or more FTEP units 150 are used in parallel.

The FTEP described herein comprises a filter 172 in the inlet-filter region 106a of flow channel 106 and a filter 170 in the outlet-filter region 106e of flow channel 106, as well as the obstruction array 176 comprising a plurality of obstructions. The filters serve the purpose of filtering the fluid containing the cells and DNA (or other material to be porated into the cells) before the fluid encounters either the inlet-proximal region 106b or outlet-proximal region 106d of flow channel 106. In this embodiment, there are filters both at the inlet-filter region 106a and outlet-filter region 106e of flow channel 106 because the FTEP devices may utilize a push-pull pneumatic means to flow liquids from inlet 102 to outlet 104, then from outlet 104 back to inlet 102 for another round of electroporation. The filter, like the obstruction array, decreases the likelihood that cells or other matter will clog the flow channel. Instead, if there is particulate matter that poses a threat to clogging the flow channel, the filter will catch the particulate matter leaving other pores or flow paths through which the rest of the cell/DNA/fluid can pass. Note that in this embodiment, the filter has a gradient flow path size, from large flow paths at the inlet to smaller flow paths toward the inlet proximal region 106b of the flow channel 106, and from large flow paths at the outlet 104 to small flow paths toward the outlet-proximal region 106d of flow channel 106; however, in alternative embodiments the flow paths may be the same size (e.g., not gradiated) or have an alternative gradient configuration.

The obstruction array 176 provides a number of flow paths for the cells and the material to be porated into the cells that travel through flow channel 106. Such a configuration reduces the likelihood of catastrophic failure of the FTEP device from clogging compared to devices with a single flow path. If one of the flow paths becomes clogged, the cells and material to be porated into the cells can flow through an alternative flow path. Again, a particular characteristic of the FTEP devices disclosed herein is that rather than having a single flow path for the cells to be porated, the FTEP devices have a single flow channel with many flow paths. In the devices described herein, the flow channel comprises obstructions of flow diverters such that the flow channel is separated or parallelized into many flow paths. Configuring the flow channel into many flow paths provides the advantage that if one flow path becomes clogged, there are several to many alternative flow paths that may be taken. That is, if only a single flow path is present and this single flow path is clogged or obstructed, the result is a catastrophic failure of the electroporation device.

The substrate, inlet wells, outlet wells, filters and obstruction arrays of the FTEP device can be made from many materials depending on whether the FTEP device is to be reused, autoclaved, or is disposable, including stainless steel, silicon, glass, resin, polyvinyl chloride, polyethylene, polyamide, polystyrene, polyethylene, polypropylene, acrylonitrile butadiene, polycarbonate, polyetheretheketone (PEEK), polysulfone and polyurethane, co-polymers of these and other polymers. Similarly, the walls of the channels in the device can be made of any suitable material including silicone, resin, glass, glass fiber, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Preferred materials include crystal styrene, cyclo-olefin polymer (COP) and cyclic olefin co-polymers (COC), which allow the FTEP device to be formed entirely by injection molding in one piece with the exception of the electrodes and, e.g., a bottom and/or top sealing film if present.

The FTEP devices described herein (or portions of the FTEP devices) can be created or fabricated via various techniques, e.g., as entire devices or by creation of structural layers that are fused or otherwise coupled. For example, for metal FTEP devices, fabrication may include precision mechanical machining or laser machining; for silicon FTEP devices, fabrication may include dry or wet etching; for glass FTEP devices, fabrication may include dry or wet etching, powderblasting, sandblasting, or photostructuring; and for plastic FTEP devices, fabrication may include thermoforming, injection molding, hot embossing, or laser machining. The components of the FTEP devices may be manufactured separately and then assembled, or certain components of the FTEP devices (or even the entire FTEP device except for the electrodes) may be manufactured (e.g., using 3D printing) or molded (e.g., using injection molding) as a single entity, with other components added after molding. For example, housing and channels may be manufactured or molded as a single entity, with the electrodes later added to form the FTEP unit. In some embodiments, a film or a flat substrate may be used to seal the bottom of the device. The film, in some embodiments, is made from the same material as the FTEP device, in this case, e.g., crystal styrene, cyclo-olefin polymer (COP) or cyclic olefin co-polymers (COC). The FTEP device may also be formed in two or more parallel layers, e.g., a layer with the horizontal channel and filter, a layer with the vertical channels, and a layer with the inlet and outlet ports, which are manufactured and/or molded individually and assembled following manufacture.

In specific aspects, the FTEP device can be manufactured using a circuit board as a base, with the electrodes, filter and/or the flow channel formed in the desired configuration on the circuit board, and the remaining housing of the device containing, e.g., the one or more inlet and outlet channels and/or the flow channel formed as a separate layer that is then sealed onto the circuit board. The sealing of the top of the housing onto the circuit board provides the desired configuration of the different elements of the FTEP devices of the disclosure. Also, two to many FTEP devices (up to 48 or more) may be manufactured in parallel on a single substrate, then separated from one another thereafter or used in parallel. In certain embodiments, the FTEP devices are reusable and, in some embodiments, the FTEP devices are disposable. In additional embodiments, the FTEP devices may be autoclavable.

The electrodes 108 can be formed from any suitable metal, such as copper, stainless steel, titanium, aluminum, brass, silver, rhodium, gold or platinum, or graphite. One preferred electrode material is alloy 303 (UNS330300) austenitic stainless steel. An applied electric field can destroy electrodes made from of metals like aluminum. If a multiple-use (e.g., non-disposable) FTEP device is desired—as opposed to a disposable, one-use FTEP device—the electrode plates can be coated with metals resistant to electrochemical corrosion. Conductive coatings like noble metals, e.g., gold, can be used to protect the electrode plates.

The overall size of the FTEP device may be from 3 cm to 15 cm in length, or 4 cm to 12 cm in length, or 4.5 cm to 10 cm in length. The overall width of the FTEP device may be from 0.5 cm to 5 cm, or from 0.75 cm to 3 cm, or from 1 cm to 2.5 cm, or from 1 cm to 1.5 cm.

In embodiments of the FTEP device where reservoirs are used to introduce cells and exogenous material into the FTEP device, the reservoirs range in volume from 100 µL to 10 mL, or from 500 µL to 7.5 mL, or from 1 mL to 5 mL. The flow rate in the FTEP ranges from 0.01 mL to 5.0 mL per minute, or from 0.05 mL to 3.0 mL per minute, or from 0.1 mL to 2.5 mL per minute or from 0.2 to 2.0 mL per minute. The pressure in the FTEP device ranges from 1-30 psi, or from 2-10 psi, or from 3-5 psi.

To avoid different field intensities between the electrodes, the electrodes should be arranged in parallel. Furthermore, the surface of the electrodes should be as smooth as possible without pin holes or peaks. Electrodes having a roughness Rz of 1 to m are preferred. In another embodiment of the invention, the flow-through electroporation device comprises at least one additional electrode which applies a ground potential to the FTEP device.

The electrodes are configured to deliver 1-50 kV/cm, or 5-40 kV/cm, or 10-25 kV/cm. The further apart the electrodes are, the more voltage needs to be supplied; in addition, the voltage delivered of course depends on the types of cells being porated, the medium in which the cells are suspended, the size of the electroporation channel, and the length and diameter of the electrodes. There are many different pulse forms that may be employed with the FTEP device, including exponential decay waves, square or rectangular waves, arbitrary wave forms, or a selected combination of wave forms. One type of common pulse form is the exponential decay wave, typically made by discharging a loaded capacitor to the cell sample. The exponential decay wave can be made less steep by linking an inductor to the cell sample so that the initial peak current can be attenuated. When multiple waveforms in a specified sequence are used, they can be in the same direction (direct current) or different directions (alternating current). Using alternating current can be beneficial in that two topical surfaces of a cell instead of just one can be used for molecular transport, and alternating current can prevent electrolysis. The pulse generator can be controlled by a digital or analog panel. In some embodiments, square wave forms are preferred, and in other embodiments, an initial wave spike before the square wave is preferred.

The FTEP device may be configured to electroporate cell sample volumes between 1 µL to 5 ml, 25 µL to 2.5 ml, 50 µL to 2 ml, 100 µL to 1 µL, or 200 µL to 750 L. The medium or buffer used to suspend the cells and material (reagent) to be electroporated into the cells for the electroporation process may be any suitable medium or buffer for the type of cells being transformed or transfected, such as SOC, MEM, DMEM, IMDM, RPMI, Hanks', PBS and Ringer's solution, where the media may be provided, e.g., in a reagent cartridge as part of a kit. Further, because the cells must be made electrocompetent prior to transformation or transfection, the buffer also may comprise glycerol or sorbitol, and may also comprise a surfactant. For electroporation of most eukaryotic cells the medium or buffer usually contains salts to maintain a proper osmotic pressure. The salts in the medium or buffer also render the medium conductive. For electroporation of very small prokaryotic cells such as bacteria, sometimes water or 10% glycerol is used as a low conductance medium to allow a very high electric field strength. In that case, the charged molecules to be delivered still render water-based medium more conductive than the lipid-based cell membranes and the medium may still be roughly considered as conductive particularly in comparison to cell membranes.

The compound to be electroporated into the cells can be any compound known in the art to be useful for electroporation, such as nucleic acids, oligonucleotides, polynucleotides, DNA, RNA, peptides, proteins and small molecules like hormones, cytokines, chemokines, drugs, or drug precursors. In addition, the FTEP devices may comprise push-pull pneumatic means to allow multi-pass electroporation procedures; that is, cells to be electroporated may be "pulled" from the inlet toward the outlet for one pass of electroporation, then be "pushed" from the outlet end of the flow-through FTEP device toward the inlet end to pass between the electrodes again for another pass of electroporation. This process may be repeated one to many times. Alternatively, the FTEP may be used to porate sequential aliquots of cells; for example, a first volume of cells is porated in a first pass with the first volume then transferred to recovery, then a second volume of cells is porated in a second pass with the second volume then transferred to recovery, and so on with third, fourth and fifth volumes or more.

Figures 1D, 1E:
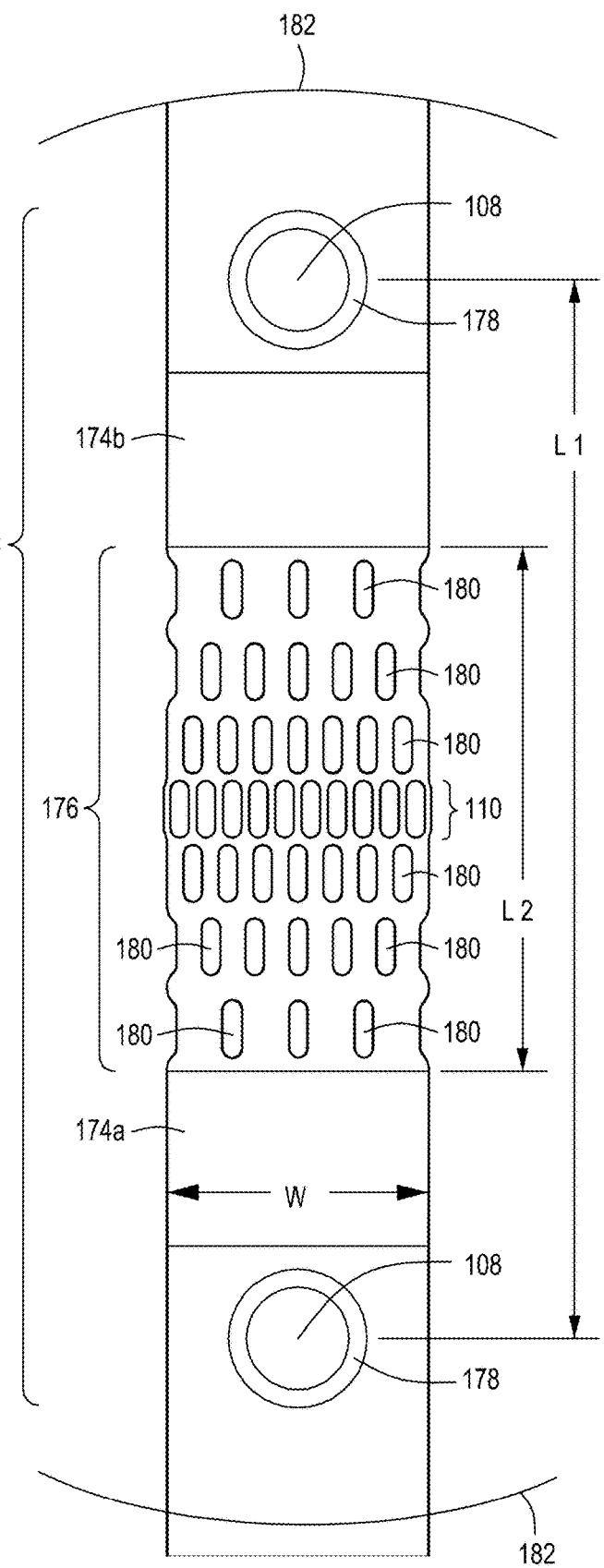
FIG. 1D depicts one embodiment of a bottom view of an FTEP.
FIG. 1E is a blow up of the circled region of FIG. 1D.

FIG. 1D is an enlarged bottom view of an FTEP device 150 with the regions of the flow channel labeled. The FTEP device 150 comprises an inlet 102, an outlet 104, a flow channel 106 comprising five regions: an inlet-filter region 106a, an inlet-proximal region 106b, a central region 106c, an outlet-proximal region 106d, and an outlet-filter region 106e. Two electrodes 108 flank the central region 106c of flow channel 106 which comprises the obstruction array. Also seen are ramps 174a and 174b. Ramp 174a proximal to inlet 102 decreases the cross-sectional area of flow channel 106 from the region of ramp 174a proximal to electrode 108 traveling toward the region of ramp 174a proximal to the central region 106c of flow channel 106. Ramp 174b proximal to outlet 104 increases the cross-sectional area of flow channel 106 from the region of ramp 174b proximal to central region 106c of flow channel 106 traveling toward electrode 108. Channel height is a parameter that can be used to tune electric field strength. At constant applied voltage, the electric field strength can be increased by reducing the cross-sectional area of the flow channel through which the cells pass. For example, as the height of the flow channel decreases, the electric field strength increases. Similarly, as described above, when the spacing between the obstructions in the obstruction array gets smaller, the electric field strength increases. Thus, the optional ramps serve the purpose of increasing electric field strength to achieve enhanced electroporation efficiency. Ramps 174a and 174b may be configured similarly (though in mirror image) or may have different configurations. The ramps can range in length from 0.3 mm to 4.0 mm, or from 0.5 mm to 3.0 mm, or from 0.8 mm to 2.4 mm. Width W of the ramp 174 is preferably equal to that of the channel, such as approximately 0.5 mm to 10 mm, or from 1 mm to 5 mm, or from 1.5 mm to 4 mm. Ramp 174a decreases the cross-sectional height of central region 106c of flow channel 106—and ramp 174b increases the cross-sectional height of central region 106c of flow channel 106 to electrode 108— from 250 µm to 25 µm, or from 200 µm to 50 µm, or from 100 µm to 25 µm. Additionally, the configuration of ramps 174a and 174b may be a smooth transition of flow channel height from larger cross-sectional height to smaller cross-sectional height, or the configuration of ramps 174a and 174b may be stepped. For example for ramp 174a, a first step may decrease the cross-sectional height of central region 106c by 25 mm for a length X of central region 106c, then a next step may decrease the cross-sectional height of central region 106c by another 25 mm for length Y of central region 106c. Again, the configuration of ramp 174b may match (mirror image) the configuration of ramp 174 a or may be different than that of 174a.

Obstruction array 176 includes a plurality (e.g., several to many) of obstructions (not seen clearly in this FIG. 1D) which provide a number of flow paths for cells to travel through flow channel 106. Additionally seen are filters 172 and 170 included in the inlet-filter region 106a and outlet-filter region 106e, respectively, of flow channel 106 to prevent clogging of flow channel 106. FIG. 1E is a blow up of the circled portion 182 of FIG. 1D showing detail of central region 106c of flow channel 106. Seen in FIG. 1E are two electrodes 108, disposed in electrode channels 178, which flank central region 106c of flow channel 106. The detail of obstruction array 176 is seen, with individual obstructions 180. In addition, optional ramp regions 174a and 174b are seen. The ramp regions ramp up (e.g. creates vertical cross-sectional narrowing of flow channel 106) from the inlet-proximal region 106b (not seen) of flow channel 106 toward central region 106c, and ramp down (e.g., creates a vertical widening of flow channel 106) from central region 106c toward outlet proximal region 106d (not shown) of flow channel 106 as described above.

Depending on the type of cells to be electroporated (e.g., bacterial, yeast, mammalian) and the configuration of the electrodes, the distance between the electrodes in the flow channel can vary widely. The length L1 from the mid-point of each electrode 108 is approximately 1 to 15 mm, or 2 to 12 mm, 3 to 10 mm, or 4 mm to 8 mm.

FIG. 1F-1K show different views of obstruction arrays 176, with individual obstructions 180. FIG. 1F depicts a top view of central region 106c of the flow channel (not labeled), with a central portion 110 of central region 106c, ramps 174a and 174b, obstruction array 176, and electrodes 108 disposed in electrode channels 178. FIG. 1G is a top perspective view of the central region (not labeled) of the flow channel (also not labeled), depicting central portion 110 of the central region, obstruction array 176, ramps 174, and electrodes 108 disposed within electrode channels 178. FIG. 1H is a close up of an obstruction array (not labeled) showing obstructions 180 and flow paths 182 between obstructions 180. Although the obstructions are shown in this embodiment as oval-shaped, flat-topped elements, it should be understood that the obstructions may be triangular-, square-, rectangular-, pentagonal-, hexagonal-, rounded peg-, elliptical-, elongated oval—(see, e.g., FIG. 1L-1N), or other faceted-shaped elements, and may be a combination of shapes and configurations of obstruction elements.

In this embodiment, there are 40 total obstructions, and the size of the flow paths moving from the inlet-proximal region of the flow channel (not labeled) to the center region of the central region 106c of the flow channel decreases; that is, the number of obstructions in a row moving from the inlet-proximal region of the flow channel to the center portion 110 of the central region 106c of the flow channel increases from 3 to 5 to 7 to 10. Similarly, the size of the flow paths moving from the center portion 110 of the central region 106c to the outlet-proximal region of the flow channel (not labeled) increases; that is, the number of obstructions in a row moving from the center portion 110 of the central region 106c to the outlet-proximal region of the flow channel (not labeled) decreases from 10 to 7 to 5 to 3. At the mid-point of the obstruction array (e.g., the center portion 110 of center region of the flow path (not labeled) there are 10 obstructions 180 defining 11 flow paths. The number of obstructions can range from 4 to 150, from 6 to 120, from 8 to 100, or from 10 to 90. The pattern or configuration of the obstructions can be symmetrical (as in FIG. 1F-1K) or random. In this embodiment, the oval-shaped or elongated obstructions are approximately 220 µm long and 100 µm wide, and the obstructions are at least about 100 µm apart, thus forming minimal flow path widths of 100 µm. However, in alternative embodiments the obstructions can be from 50 µm long to 20 µm wide, from 100 µm long to 50 µm wide, or from 250 µm long to 150 µm wide. Round obstructions may be used instead or in combination with elongated obstructions or with other configurations of obstructions. Round obstructions may be approximately between 25 µm-200 µm in diameter, or between 50 µm to 150 µm in diameter, or 75 µm to 125 µm in diameter. The flow paths or distance between obstructions can range from 10 µm to 350 µm, from 20 µm to 300 µm, or from 30 µm to 250 µm.

FIGS. 1I-1K are similar to FIG. 1F-1H, showing views of an alternately-configured obstruction array 176 and individual obstruction 180s. FIG. 1I shows a top view of central region 106c of flow channel (not labeled), with central portion 110, ramps 174, and electrodes 108 in electrode channels (not labeled). FIG. 1J is a top view of an area of an obstruction array (not labeled) showing individual obstructions 180 and central portion 110 of the central region (not labeled) of the flow channel (also not labeled). Note that the outer margin of the FTEP device in central region (not labeled) coincident to the obstruction array is contoured to provide flow paths 182 similar to the flow channels between obstructions 180. FIG. 1K is a close-up view of obstructions 180 and flow paths 182. Again the obstructions are shown in this embodiment as oval-shaped, flat-topped elements; however, it should be understood that the obstructions may be triangular-, square-, rectangular-, pentagonal-, hexagonal-, rounded peg-, elliptical-, elongated oval- or other faceted-shaped elements, and may be a combination of shapes and configurations of obstruction elements. In this embodiment, there are 33 total obstructions in a 3-5-5-7-5-5-3 pattern moving from the inlet-proximal region of the flow channel to the center portion of the center region of the flow channel to the outlet-proximal region of the flow channel (regions not labeled).

Figures 1L, 1M:
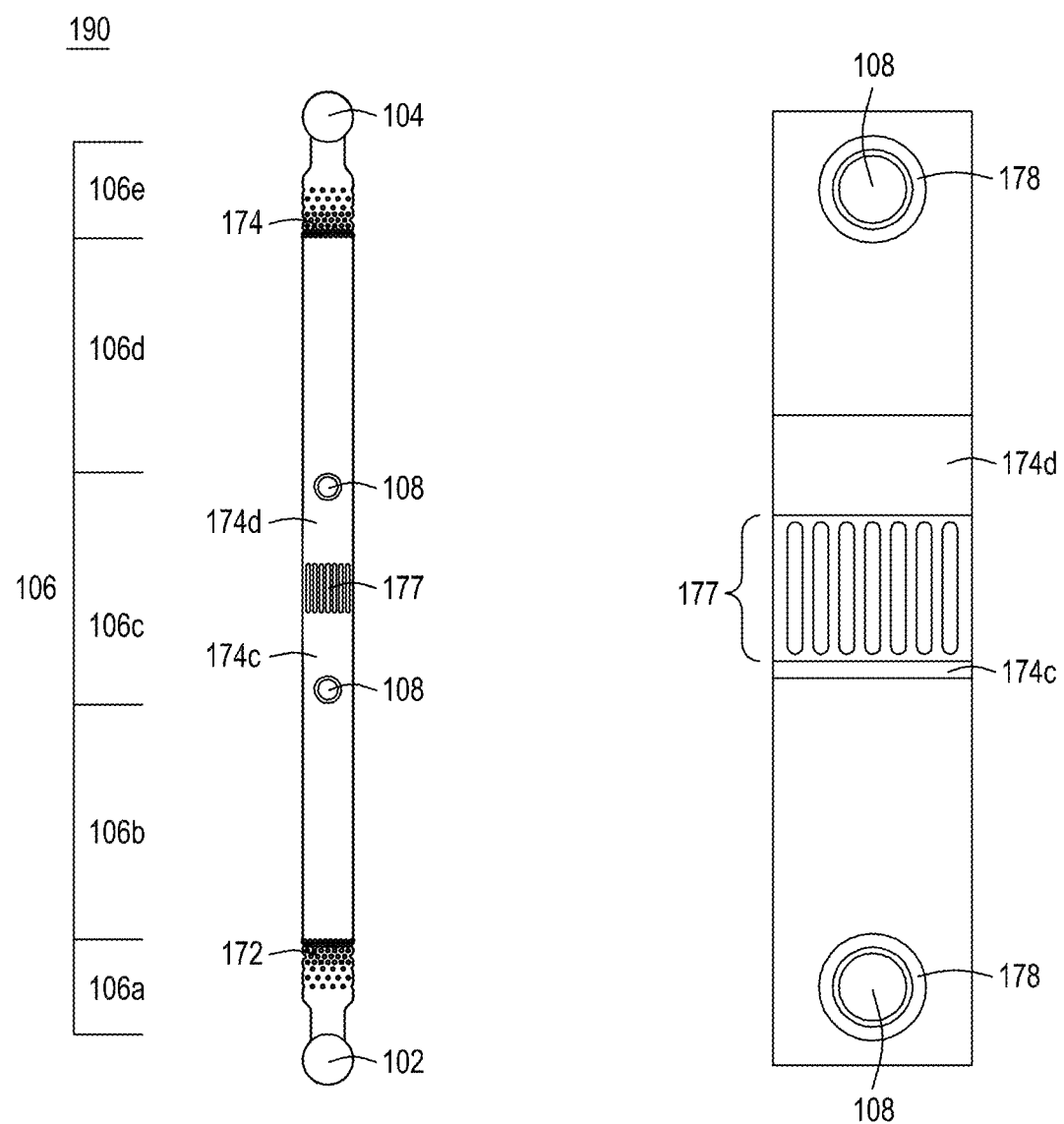
FIG. 1L-1N are representations of an alternative embodiment of an obstruction array and individual obstruction structures.

FIG. 1L is a bottom view of an alternative embodiment of an obstruction FTEP device 190, here a parallel-obstruction device, with the regions of the flow channel labeled. The parallel-obstruction FTEP device 190 comprises an inlet 102, an outlet 104, a flow channel 106 comprising five regions: an inlet-filter region 106a, an inlet-proximal region 106b, a central region 106c, an outlet-proximal region 106d, and an outlet-filter region 106e. Two electrodes 108 flank the central region 106c of flow channel 106 which comprises the obstruction array 177. Also seen are steps 174c and 174d. Steps 174c and 174d are much like ramps 174a and 174b seen in FIGS. 1D, 1E, 1G and 1I; however, instead of a "ramp" or gradual decreasing of channel height (with ramp 174a) or gradual increasing of channel height (as with ramp 174b), steps 174c and 174d are true steps—that is, the decrease or increase in channel height to and from the central channel region 106c is abrupt. Step 174c proximal to inlet 102 decreases the cross-sectional area of flow channel 106 from the region of step 174c proximal to electrode 108 traveling toward the region of step 174c proximal to the central region 106c of flow channel 106. Step 174d proximal to outlet 104 increases the cross-sectional area of flow channel 106 from the region of step 174d proximal to central region 106c of flow channel 106 traveling toward electrode 108 and outlet 104. As described above, channel height is a parameter that can be used to tune electric field strength. At constant applied voltage, the electric field strength can be increased by reducing the cross-sectional area of the flow channel through which the cells pass. For example, as the height of the flow channel decreases, the electric field strength increases. The steps serve the purpose of increasing electric field strength to achieve enhanced electroporation efficiency. As with ramps 174a and 174b, steps 174c and 174d may be configured similarly (though in mirror image) or may have different configurations. For an exemplary channel height of 100 m, the step can range in height from 10 µm to 80 µm, or from 20 µm to 70 µm, or from 20 µm to 60 m. Width W of the steps 174c and 174d is preferably equal to that of the channel, such as approximately 0.5 mm to 3.0 mm, or from 1.0 mm to 2.0 mm, or from 1.25 mm to 1.75 mm. For other channel heights, the steps would be of the same proportion. Again, the configuration of step 174c may match (mirror image) the configuration of step 174d or may be different than that of 174d. Parallel-obstruction array 177 includes a plurality (e.g., several to many) of obstructions in central region 106c (not seen clearly in this FIG. 1L) which provide a number of flow paths for cells to travel through flow channel 106. Additionally seen are filters 172 and 170 included in the inlet-filter region 106a and outlet-filter region 106e, respectively, of flow channel 106 to prevent clogging of flow channel 106.

Figure 1N:
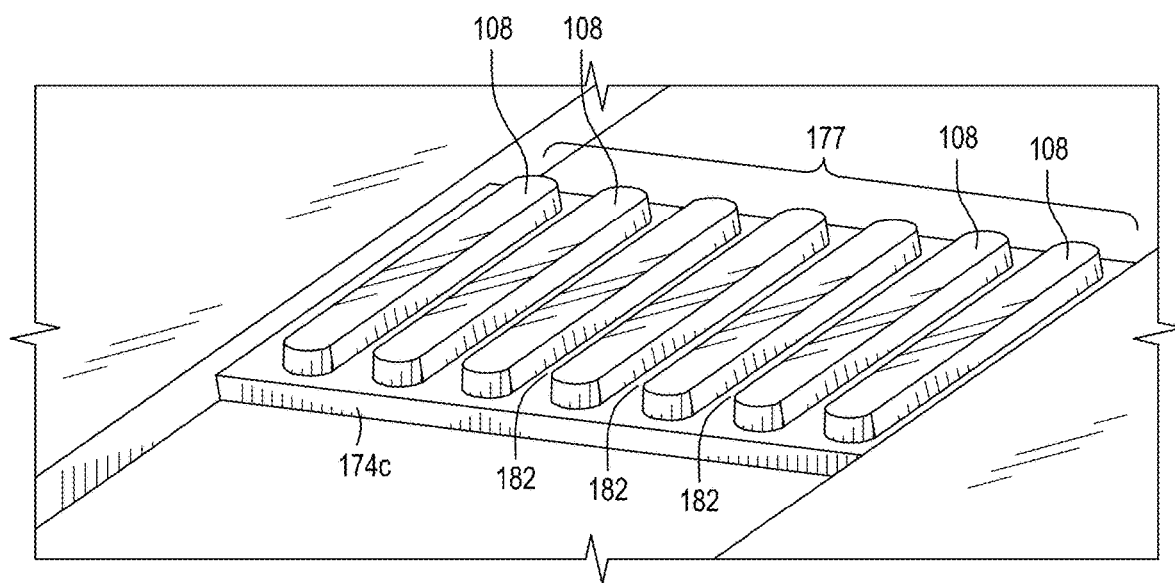

FIGS. 1M and 1N show different views of parallel-obstruction arrays 177 (e.g., obstructions with a different configuration than shown in FIGS. 1D-1K), with individual obstructions 180. In FIGS. 1M and 1N, the obstructions or flow diverters are elongated oval structures that are arranged parallel to one another forming "lanes" for cell flow. That is, instead of a plurality of obstructions arranged in a pattern such as in rows (see, e.g., the 3-5-5-7-5-5-3 pattern in FIGS. 1I-1K), the present parallel-obstruction embodiment comprises elongated obstructions that form flow "lanes." FIG. 1M depicts a top view of central region 106c of the flow channel (not labeled), with a central portion 110 of central region 106c, steps 174c and 174d, obstruction array 177, and electrodes 108 disposed in electrode channels 178. Note that the length of the obstruction array 177 in channel 106 is denoted here as 1.0 mm in length with the length of the "shelf" formed by the steps approximately 1.1 mm in length.

FIG. 1N is a top perspective view of the central region (not labeled) of the flow channel (also not labeled), depicting parallel-obstruction array 177 in channel 106 (not labeled) and step 174c, obstructions 180 and flow paths 182 between obstructions 180. Although the obstructions are shown in this embodiment as long oval-shaped, flat-topped elements, it should be understood that the obstructions may be triangular-, square-, rectangular-, pentagonal-, hexagonal-, rounded peg-, elliptical- or other faceted-shaped elements, and may be a combination of shapes and configurations of obstruction elements. Note that step 174c decreases the channel height in this exemplary embodiment from 100 µm to 50 µm, and the height of obstructions 180 is 50 µm.

In this embodiment, there are 7 total obstructions in parallel, resulting in 8 parallel paths for cell flow. In this embodiment, the elongated obstructions are approximately 1000 µm long and 100 µm wide, and the obstructions are at least about 200 µm apart center-to-center of the obstructions, thus forming minimal flow path widths of approximately 100 µm. However, in alternative embodiments the obstructions can be from 200 µm long to 25 µm wide, from 500 µm long to 50 µm wide, or from 4000 µm long to 100 µm wide, with the length of the obstructions limited only by the distance between electrodes. The flow lanes between obstructions can range from 2 µm to 300 µm, from 10 µm to 200 µm, or from 25 µm to 100 µm in width.

FIG. 1O depicts (i) the electrodes 108 positioned on an electrode platform 158 before insertion into the FTEP array 1500; here an FTEP array comprising six FTEP devices (not labeled), where each FTEP device has an inlet well 152 and an outlet well 154. In use, the FTEP devices are used in an orientation inverted relative to that shown in FIG. 1O (i). FIG. 1O (ii) depicts an electrode 108 contained within and projecting from an electrode sheath 184. FIG. 1O (iii) depicts the electrode 108 within electrode sheath 184 and inserted into an electrode channel 178 with the electrode channel 178 (and electrode 108) adjacent to flow channel 106. In the embodiment shown in FIG. 1O (iii), electrode 108 is even/flush with the wall of flow channel 106; that is, electrode 108 is not in the path of the cells/DNA/fluid flowing through flow channel 106; however, neither is the electrode recessed within the electrode channel 178. In alternative embodiments, electrode 108 may be recessed within electrode channel 178. The configuration of the electrode channel 178 and the flow channel 106 help prevent trapping air and reduce discontinuities in the electric field.

Figure 1P:
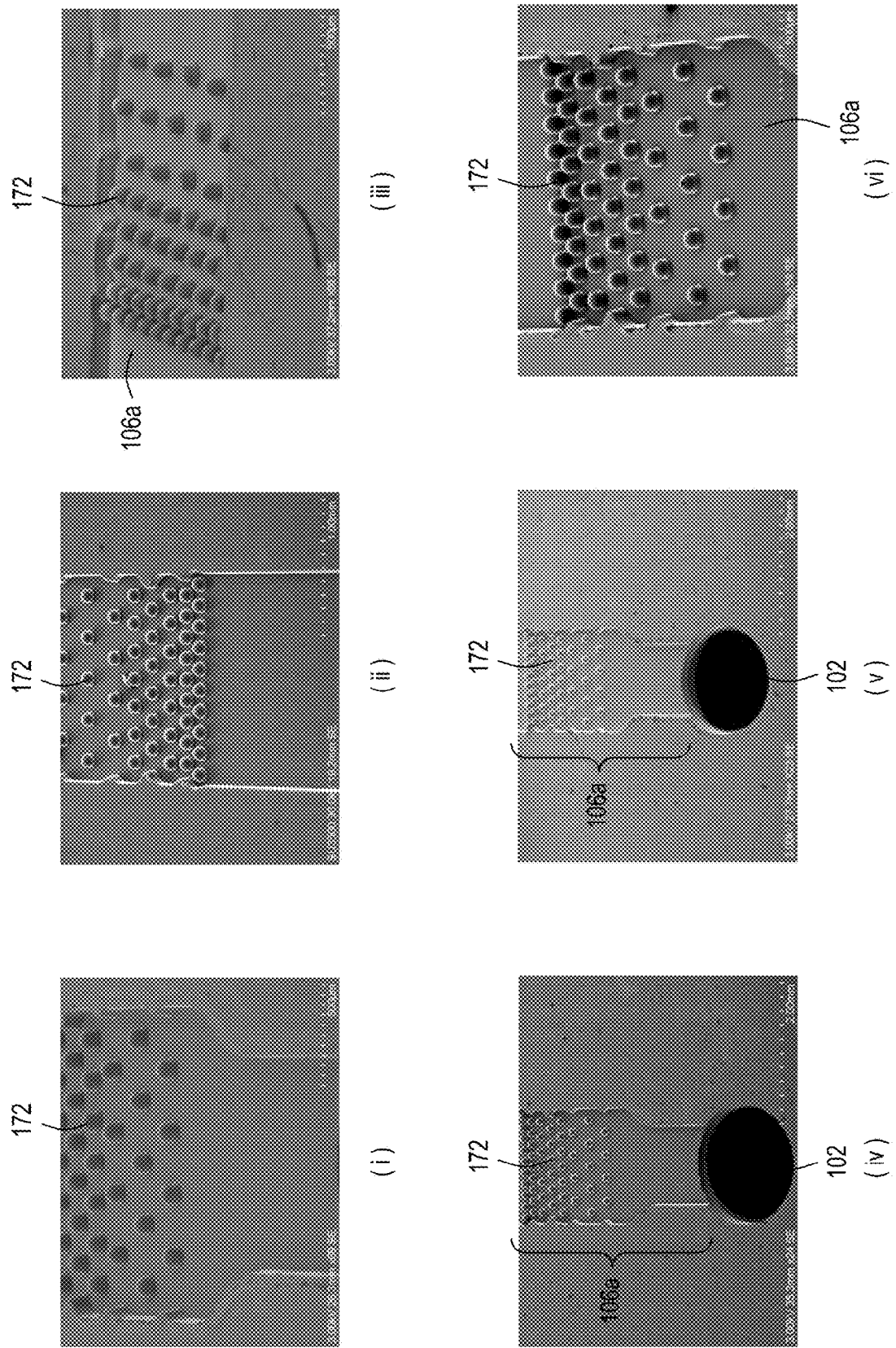
FIG. 1P shows scanning electromicrographs of an inlet-filter region of a flow channel comprising a filter, as well as an inlet.

FIG. 1P shows scanning electron micrographs of filter 172. Note in this embodiment, the porosity of filter 172 varies from large flow paths near the inlet 102 to small flow paths near inlet proximal region 106b (not shown). When a second filter is present at the outlet-filter region 106e (not shown), the second filter may also vary in porosity. In the case of a second filter between the outlet and the outlet-proximal region 106d, the filter can vary from large flow paths near the outlet proximal region to small flow paths toward the outlet-proximal region 106d. Scale information is shown in each micrograph. Moreover, as with the configuration of the obstructions, though the scanning electron micrographs in FIG. 1P show the filter elements as rounded "pegs", it should be understood that the filter elements may be triangular-, square-, rectangular-, pentagonal-, hexagonal-, oval-, elliptical- or other faceted-shaped pegs, or a combination of differently-configured and differently-sized filter elements.

Reagent Cartridges Comprising FTEPs

Figures 2A, 2B:
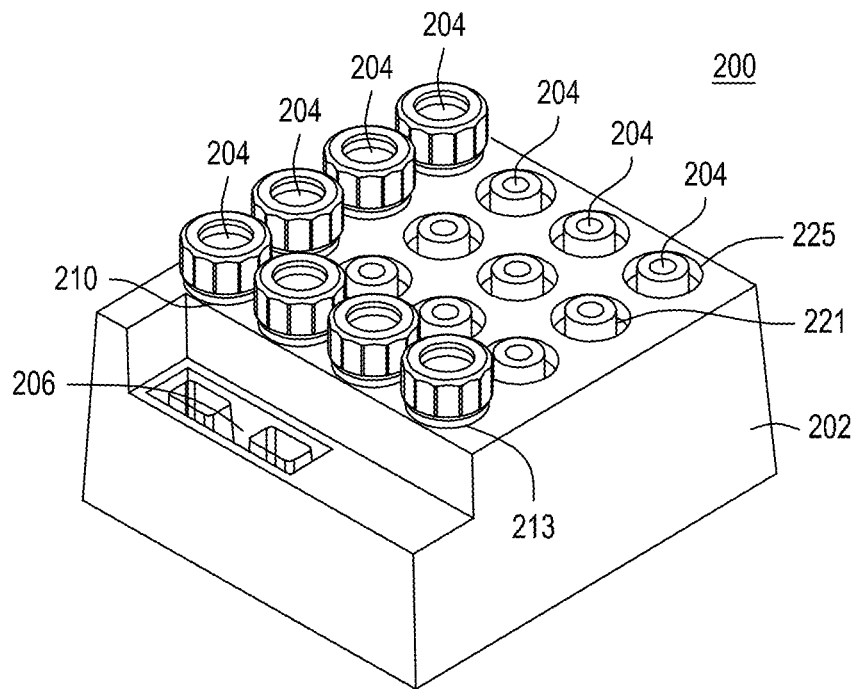
FIGS. 2A and 2B depict the structure and components of an exemplary embodiment of a reagent cartridge comprising an FTEP device.

FIG. 2A depicts an exemplary combination reagent cartridge 200 comprising an FTEP device 206 ("cartridge" or "reagent cartridge") that may be used in an automated multi-module cell processing instrument. Cartridge 200 comprises a body 202, and reagent receptacles or reservoirs 204 along with an FTEP device 206 (exemplary embodiments of which are described in detail in relation to FIGS. 1A-1P). Cartridge 200 may be disposable or may be configured to be reused. Cartridge 200 may be made from any suitable material, including stainless steel, aluminum, paper or other fiber, or plastics including polyvinyl chloride, cyclic olefin copolymer (COC), polyethylene, polyamide, polypropylene, acrylonitrile butadiene, polycarbonate, polyetheretheketone (PEEK), poly(methyl methylacrylate) (PMMA), polysulfone, and polyurethane, and co-polymers of these and other polymers. If the cartridge is disposable, preferably it is made of plastic or paper. Preferably the material used to fabricate the cartridge is thermally-conductive, as in certain embodiments the cartridge 200 contacts a thermal device (not shown) that heats or cools reagents in the reagent receptacles or reservoirs 204. In some embodiments, the thermal device is a Peltier device or thermoelectric cooler. Reagent receptacles or reservoirs 204 may be receptacles into which individual tubes of reagents are inserted as shown in FIG. 2A, receptacles into which one or more multiple co-joined tubes are inserted (e.g., a row of four tubes that are co-joined are inserted into the reagent receptacles), or the reagent receptacles may hold the reagents without inserted tubes with the reagents dispensed directly into the receptacles or reservoirs. Additionally, the receptacles 204 in a reagent cartridge 200 may be configured for any combination of tubes, co-joined tubes, and direct-fill of reagents.

In one embodiment, the reagent receptacles or reservoirs 204 of reagent cartridge 200 are configured to hold various size tubes, including, e.g., 250 ml tubes, 25 ml tubes, 10 ml tubes, 5 ml tubes, and Eppendorf (e.g., microcentrifuge) tubes. In yet another embodiment, all receptacles may be configured to hold the same size tube, e.g., 5 ml tubes, and reservoir inserts may be used to accommodate smaller tubes in the reagent reservoir. In yet another embodiment-particularly in an embodiment where the reagent cartridge 200 is disposable—the reagent reservoirs 204 hold reagents without inserted tubes. In this disposable embodiment, the reagent cartridge may be part of a kit, where the reagent cartridge is pre-filled with reagents and the receptacles or reservoirs sealed with, e.g., foil, film, heat seal acrylic or the like and presented to a consumer where the reagent cartridge can then be used in an automated multi-module cell processing instrument. The reagents contained in the reagent cartridge 200 will vary depending on work flow; that is, the reagents will vary depending on the processes to which the cells are subjected in the automated multi-module cell processing instrument. For various embodiments of reagent cartridges of particular use in automated multi-module cell processing instruments, see U.S. Pat. No. 10,376,889, issued 13 Aug. 2019; U.S. Pat. No. 10,406,525, issued 10 Sep. 2019; and U.S. Pat. No. 10,478,822, issued 19 Nov. 2019.

FIG. 2B depicts an exemplary matrix configuration 240 for the reagents contained in the reagent cartridges of FIG. 2A, where this matrix embodiment is a 4×4 reagent matrix. Through a matrix configuration, a user (or programmed processor) can locate the proper reagent for a given process. That is, reagents such as cell samples, enzymes, buffers, nucleic acid vectors, expression cassettes, reaction components (such as, e.g., $MgCl_2$, dNTPs, isothermal nucleic acid assembly reagents, Gap Repair reagents, and the like), wash solutions, ethanol, and magnetic beads for nucleic acid purification and isolation, etc., are positioned in the matrix 240 at a known position. For example, reagents are located at positions A1 (210), A2 (211), A3 (212), A4 (213), B1 (214), B2 (215) and so on through, in this embodiment, to position D4 (225). FIG. 2A is labeled to show where several reservoirs 204 correspond to matrix 240; see receptacles 210, 211, 212, 213, 221 and 225. Although the reagent cartridge 200 of FIG. 2A and the matrix configuration 240 of FIG. 2B shows a 4×4 matrix, matrices of the reagent cartridge and electroporation devices can be any configuration, such as, e.g., 2×2, 2×3, 2×4, 2×5, 2×6, 3×3, 3×5, 4×6, 6×7, or any other configuration, including asymmetric configurations, or two or more different matrices depending on the reagents needed for the intended workflow.

In preferred embodiments of reagent cartridge 200 shown in FIG. 2A, the reagent cartridge comprises a script (not shown) readable by a processor (not shown) for dispensing the reagents via a liquid handling device (ADP head shown at 432 of FIG. 4A) and controlling the electroporation device contained within reagent cartridge 200. Also, the reagent cartridge 200 as one component in an automated multi-module cell processing instrument may comprise a script specifying two, three, four, five, ten or more processes performed by the automated multi-module cell processing instrument, or even specify all processes performed by the automated multi-module cell processing instrument. In certain embodiments, the reagent cartridge is disposable and is pre-packaged with reagents tailored to performing specific cell processing protocols, e.g., genome editing or protein production. Because the reagent cartridge contents vary while components of the automated multi-module cell processing instrument may not, the script associated with a particular reagent cartridge matches the reagents used and cell processes performed. Thus, e.g., reagent cartridges may be pre-packaged with reagents for genome editing and a script that specifies the process steps (or a script that modifies the steps of a pre-programmed script based on, e.g., an updated reagent in the reagent cartridge) for performing genome editing in an automated multi-module cell processing instrument such as described in relation to FIGS. 4A-4C.

Figure 4A:
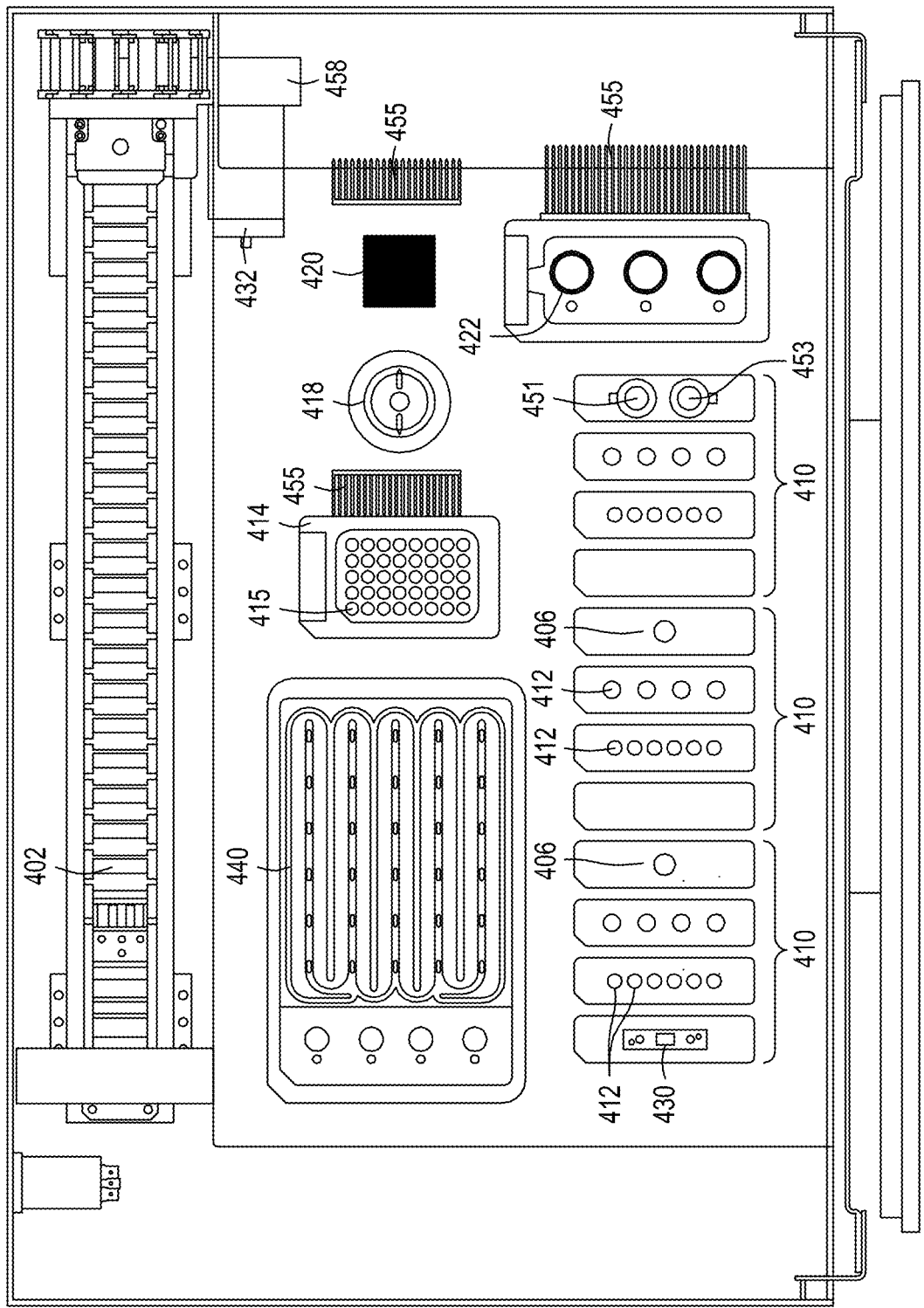
FIGS. 4A-4C depict an automated multi-module instrument and modules and components thereof with which to generate the edited cells.

For example, the reagent cartridge 200 of FIG. 2A may comprise a script to pipette electrocompetent cells from reservoir A2 (211), transfer the cells to the electroporation device 206, pipette a nucleic acid solution comprising an editing vector from reservoir C3 (220), transfer the nucleic acid solution to the electroporation device, initiate the electroporation process for a specified time, then move the porated cells to a reservoir D4 (225) in the reagent cassette or to another module such as the rotating growth vial (see, e.g., 418 of FIG. 4A) in the automated multi-module cell processing instrument in FIG. 4A. In another example, the reagent cartridge may comprise a script to pipette transfer of a nucleic acid solution comprising a vector from reservoir C3 (220), nucleic acid solution comprising editing oligonucleotide cassettes in reservoir C4 (221), and isothermal nucleic acid assembly reaction mix from A1 (210) to an isothermal nucleic acid assembly/desalting reservoir. The script may also specify process steps performed by other modules in the automated multi-module cell processing instrument. For example, the script may specify that the isothermal nucleic acid assembly/desalting module be heated to 50° C. for 30 min to generate an assembled isothermal nucleic acid product; and desalting of the assembled isothermal nucleic acid product via magnetic bead-based nucleic acid purification involving a series of pipette transfers and mixing of magnetic beads in reservoir B2 (215), ethanol wash in reservoir B3 (216), and water in reservoir C1 (218) to the isothermal nucleic acid assembly/desalting reservoir (not seen in FIG. 4A).

Figure 3A:
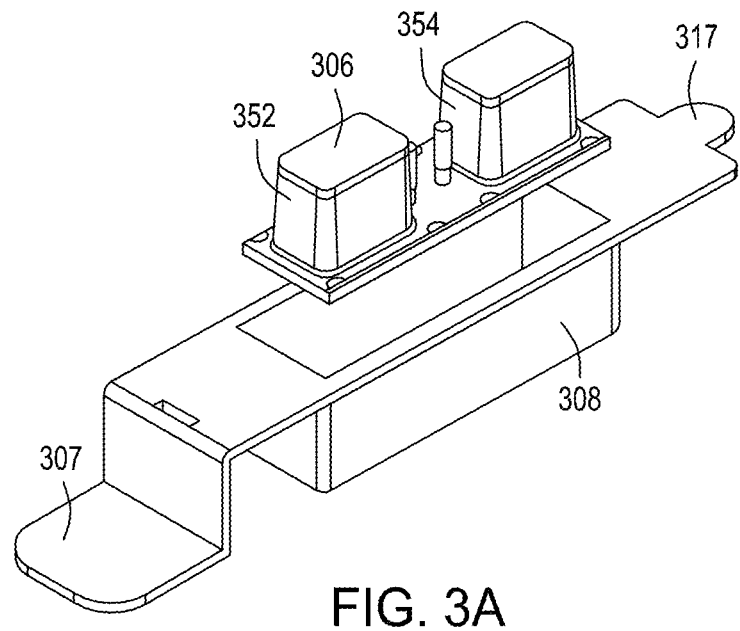
FIGS. 3A-3F depict the structure and components of an exemplary FTEP device that is configured to reside within, e.g., the exemplary reagent cartridge shown in FIG. 2A.
Figure 3B:
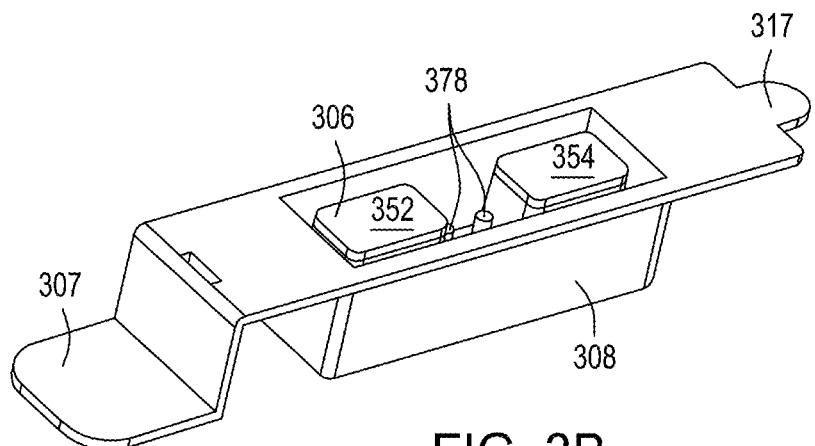
Figure 3C:
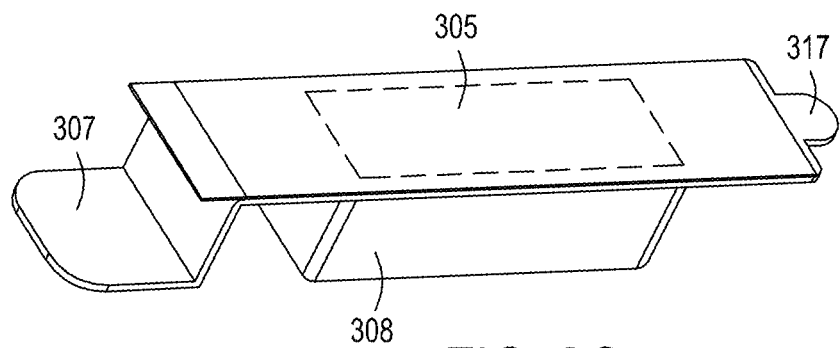

FIGS. 3A-3C depict three side perspective views of a flow-through electroporation device insert 308 configured to be inserted into, e.g., a reagent cartridge. In the embodiment of reagent cartridge 200 depicted in FIG. 2A, the flow-through electroporation device 206 (in FIGS. 3A-3F, FTEP 306) is located in the reagent cartridge 200 (also see reagent cartridge 410 with flow-through electroporation device 430 as one component of an automated multi-module cell processing instrument 400 in FIG. 4A); although in alternative embodiments, the FTEP module may be separate from the reagent cartridge. The FTEP comprises an inlet well 352 (covered in FIGS. 3A and 3B), and outlet well 354 (also covered in FIGS. 3A and 3B), and the exterior of the electrode channels 378. The FTEP device insert 308 comprises both a tab 317, and an outer flange 307. FIG. 3C depicts the FTEP device insert 308 with a cover 305 for, e.g., shipping and to keep the FTEP device 306 sterile until use. The FTEP inserts may be made of any appropriate material; however, the inserts are in most embodiments disposable, so typically are fabricated from biocompatible plastics, including polyvinyl chloride, cyclic olefin copolymer (COC), polyethylene, polyamide, polypropylene, acrylonitrile butadiene, polycarbonate, polyetheretheketone (PEEK), poly(methyl methylacrylate) (PMMA), polysulfone, and polyurethane, and co-polymers of these and other polymers.

Figure 3D:
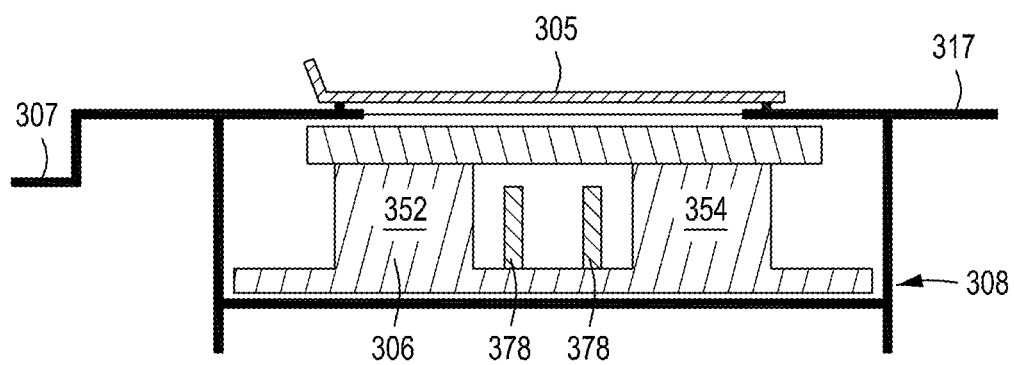
Figure 3E:
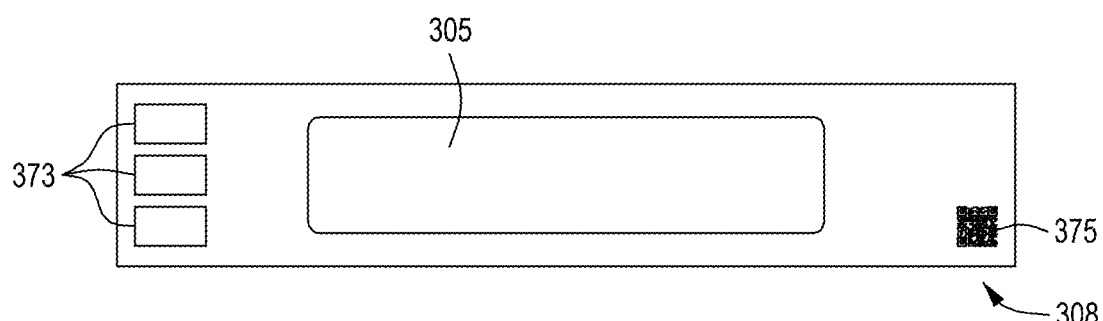
Figure 3F:
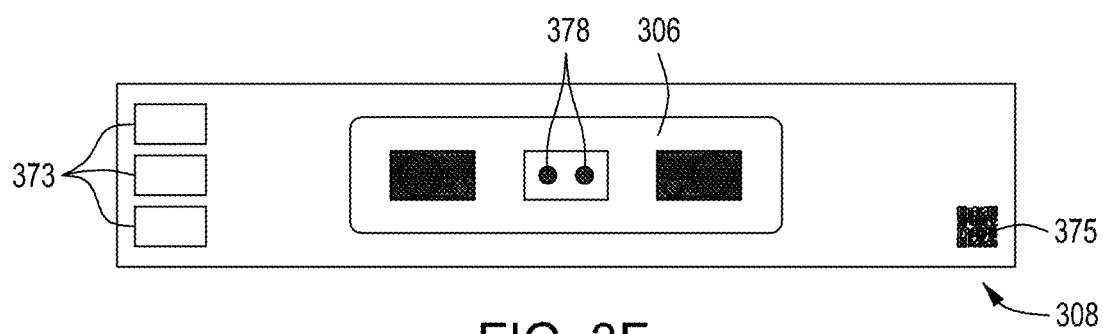

FIGS. 3D-3F offer additional views of an FTEP insert 308. FIG. 3D is a cross section of the FTEP insert 308, housing FTEP 306 with inlet well 352, outlet well 354, and electrode channels 378. FTEP insert 308 comprises an outer flange 307, an FTEP cover 305, and tab 317, which is configured to engage with, e.g., a tab engagement member (not shown) in a reagent cartridge when inserted into a reagent cartridge. Also shown is FTEP cover 305, which in this embodiment is a tear-off foil, film or other type seal that is used to maintain the sterility of the FTEP until ready for use. FIG. 3E is a top view of the FTEP insert 308 shown in FIG. 3D. Seen are FTEP insert cover or seal 305, which protects and keeps sterile the FTEP device before use and is removable by a user, data 373, and machine-readable indicia 375. Data 373 may include information such as a lot number, a serial number, a product number, an expiration date, or other data pertinent to FTEP insert 308. Machine-readable indicia 375 may be a barcode, QR code, a Data Matrix code (error correction-type barcode), RFID or other type of machine-readable indicia, detected by one or more imaging sensors (e.g., barcode scanners, cameras, etc.) (not shown) located in an automated multi-module cell processing instrument to, e.g., confirm the contents of and optionally to control the operation of FTEP insert 308. FIG. 3F is a top view of FTEP insert 308 with FTEP insert cover 305 (seen in FIG. 3E) removed. Again, data 373, machine-readable indicia 375, and FTEP 306 can be seen. Also, electrodes channels 378 of FTEP 306 are seen.

Nucleic Acid-Directed Nuclease Genome Editing Generally

The FTEP device of the present invention may be a stand-alone device or module or may be one module in an automated multi-module cell processing instrument. In one embodiment, the FTEP device is used in an automated cell processing instrument designed for creating genome edits in live cells. A recent discovery for editing live cells involves nucleic acid-guided nuclease (e.g., RNA-guided nuclease) editing. A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby. In certain aspects, the nucleic acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects, the guide nucleic acid may be a single guide nucleic acid that includes both the crRNA and tracrRNA sequences.

In general, a guide nucleic acid (e.g., gRNA) complexes with a compatible nucleic acid-guided nuclease and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may reside within an editing cassette. The sequence for the gRNA may be under the control of a constitutive promoter, or, in some embodiments and preferably, an inducible promoter as described below.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the guide nucleic acid is provided as a sequence to be expressed from a plasmid or vector and comprises both the guide sequence and the scaffold sequence as a single transcript under the control of a promoter, and in some embodiments, an inducible promoter. The guide nucleic acid can be engineered to target a desired target sequence by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. The target sequence can be a sequence encoding a gene product (e.g., a protein) or a non-coding sequence (e.g., a regulatory polynucleotide, an intron, a PAM, or "junk" DNA).

The guide nucleic acid may be part of an editing cassette that encodes the donor nucleic acid. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid in, e.g., the editing cassette. In other cases, the donor nucleic acid in, e.g., an editing cassette can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments, the sequence encoding the guide nucleic acid and the sequence encoding the donor nucleic acid are both included in the editing cassette.

The target sequence is associated with a proto-spacer mutation (PAM), which is a short nucleotide sequence recognized by the gRNA/nuclease complex. The precise preferred PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, decrease target site recognition fidelity, or increase the versatility of a nucleic acid-guided nuclease. In certain embodiments, the genome editing of a target sequence both introduces a desired DNA change to a target sequence, e.g., the genomic DNA of a cell, and removes, mutates, or renders inactive a proto-spacer mutation (PAM) region in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. The genome of the cells that did not undergo the first editing event will be cut rendering a double-stranded DNA break, and thus these cells will not continue to be viable. The genome of the cells containing the desired target sequence edit and PAM alteration will not be cut, as these edited cells no longer contain the necessary PAM site and will thus continue to grow and propagate.

The range of target sequences that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs). Because certain of the methods disclosed herein allow for identification of edited cells in a background of unedited cells (see, e.g., FIGS. 7A-7E and the descriptions thereof), the methods allow for identification of edited cells where the PAM is less than optimal; that is, the methods for identifying edited cells herein allow for identification of edited cells even if editing efficiency is very low. Additionally, the present methods expand the scope of target sequences that may be edited since edits are more readily identified, including cells where the genome edits are associated with less functional PAMs.

As for the nuclease component of the nucleic acid-guided nuclease editing system, a polynucleotide sequence encoding the nucleic acid-guided nuclease can be codon optimized for expression in particular cell types, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of nucleic acid-guided nuclease to be employed depends on many factors, such as what type of edit is to be made in the target sequence and whether an appropriate PAM is located close to the desired target sequence. Nucleases of use in the methods described herein include but are not limited to Cas 9, Cas 12/CpfI, MAD2, or MAD7 or other MADzymes. As with the guide nucleic acid, the nuclease may be encoded by a DNA sequence on a vector (e.g., the engine vector) and be under the control of a constitutive or inducible promoter. In some embodiments, the sequence encoding the nuclease is under the control of an inducible promoter, and the inducible promoter may be separate from but the same as the inducible promoter controlling transcription of the guide nucleic acid; that is, a separate inducible promoter drives the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

Another component of the nucleic acid-guided nuclease system is the donor nucleic acid. In some embodiments, the donor nucleic acid is on the same polynucleotide (e.g., editing vector or editing cassette) as the guide nucleic acid and may be (but not necessarily) under the control of the same promoter as the guide nucleic acid (e.g., a single promoter driving the transcription of both the guide nucleic acid and the donor nucleic acid). The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an editing vector, where each guide nucleic acid is under the control of separate different promoters, separate like promoters, or where all guide nucleic acid/donor nucleic acid pairs are under the control of a single promoter. In some embodiments, the promoter driving transcription of the gRNA and the donor nucleic acid (or driving more than one gRNA/donor nucleic acid pair) is an inducible promoter and the promoter driving transcription of the nuclease is an inducible promoter as well. For additional information regarding editing cassettes, see U.S. Pat. Nos. 9,982,278; 10,240,167; 10,266,849; 10,351,877; 10,364,442; and 10,435,715; and U.S. Ser. Nos. 16/275,465 and 16/551,517.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

Also, as described above, the donor nucleic acid may optionally comprise—in addition to the at least one mutation relative to a target sequence-one or more PAM sequence alterations that mutate, delete or render inactive the PAM site in the target sequence. The PAM sequence alteration in the target sequence renders the PAM site "immune" to the nucleic acid-guided nuclease and protects the target sequence from further editing in subsequent rounds of editing if the same nuclease is used.

In addition, the editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid is associated with a different barcode.

Additionally, in some embodiments, an expression vector or cassette encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs. In some embodiments, the engineered nuclease comprises NLSs at or near the amino-terminus, NLSs at or near the carboxy-terminus, or a combination thereof.

The engine and editing vectors comprise control sequences operably linked to the component sequences to be transcribed. As stated above, the promoters driving transcription of one or more components of the nucleic acid-guided nuclease editing system may be inducible such as one or both of the gRNA and the nuclease. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12): 5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8):3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others. In the present methods used in the modules and instruments described herein, it is preferred that at least one of the nucleic acid-guided nuclease editing components (e.g., the nuclease and/or the gRNA) is under the control of a promoter that is activated by a rise in temperature, as such a promoter allows for the promoter to be activated by an increase in temperature, and de-activated by a decrease in temperature, thereby "turning off" the editing process. Thus, in the scenario of a promoter that is de-activated by a decrease in temperature, editing in the cell can be turned off without having to change media; to remove, e.g., an inducible biochemical in the medium that is used to induce editing.

Automated Multi-Module Cell Processing Instruments Comprising FTEPs

The present disclosure relates to flow-through electroporation devices or modules that can be used alone, or as one module in automated multi-module cell processing instruments. In some embodiments, the FTEP may be included as part of a reagent cartridge, wherein the reagent cartridge may further include sample receptacles, reagent receptacles, and/or waste receptacles, etc.; additionally, in certain embodiments, the reagent cartridge will comprise a script readable by a processor for dispensing the reagents and controlling the electroporation device contained within the reagent cartridge. An automated multi-module cell processing instrument with an FTEP can be used to process many different types of cells in a controlled, contained, and reproducible manner, including bacterial cells, mammalian cells, non-mammalian eukaryotic cells, yeast cells, fungi, archaea, and the like.

Automated Cell Editing Instruments

FIG. 4A depicts an exemplary automated multi-module cell processing instrument 400 to, e.g., perform one of the exemplary workflows comprising a split protein reporter system as described herein. The instrument 400, for example, may be and preferably is designed as a stand-alone desktop instrument for use within a laboratory environment. The instrument 400 may incorporate a mixture of reusable and disposable components for performing the various integrated processes in conducting automated genome cleavage and/or editing in cells without human intervention. Illustrated is a gantry 402, providing an automated mechanical motion system (actuator) (not shown) that supplies XYZ axis motion control to, e.g., an automated (i.e., robotic) liquid handling system 458 including, e.g., an air displacement pipettor 432 which allows for cell processing among multiple modules without human intervention. In some automated multi-module cell processing instruments, the air displacement pipettor 432 is moved by gantry 402 and the various modules and reagent cartridges remain stationary; however, in other embodiments, the liquid handling system 458 may stay stationary while the various modules and reagent cartridges are moved. Also included in the automated multi-module cell processing instrument 400 are reagent cartridges 410 comprising reservoirs 412 and transformation module 430 (e.g., a flow-through electroporation device as described in detail in relation to FIGS. 1A-1P), as well as wash reservoirs 406, cell input reservoir 451 and cell output reservoir 453. The wash reservoirs 406 may be configured to accommodate large tubes, for example, wash solutions, or solutions that are used often throughout an iterative process. Although two of the reagent cartridges 410 comprise a wash reservoir 406 in FIG. 4A, the wash reservoirs instead could be included in a wash cartridge where the reagent and wash cartridges are separate cartridges. In such a case, the reagent cartridge 410 and wash cartridge 404 may be identical except for the consumables (reagents or other components contained within the various inserts) inserted therein. (See, e.g., FIGS. 2A and 2B.)

In some implementations, the reagent cartridges 410 are disposable kits comprising reagents and cells for use in the automated multi-module cell processing/editing instrument 400. For example, a user may open and position each of the reagent cartridges 410 comprising various desired inserts and reagents within the chassis of the automated multi-module cell editing instrument 400 prior to activating cell processing. Further, each of the reagent cartridges 410 may be inserted into receptacles in the chassis having different temperature zones appropriate for the reagents contained therein.

Also illustrated in FIG. 4A is the robotic liquid handling system 458 including the gantry 402 and air displacement pipettor 432. In some examples, the robotic handling system 458 may include an automated liquid handling system such as those manufactured by Tecan Group Ltd. of Mannedorf, Switzerland, Hamilton Company of Reno, Nev. (see, e.g., WO2018015544A1), or Beckman Coulter, Inc. of Fort Collins, Colo. (see, e.g., US20160018427A1). Pipette tips may be provided in a pipette transfer tip supply (not shown) for use with the air displacement pipettor 432.

Inserts or components of the reagent cartridges 410, in some implementations, are marked with machine-readable indicia (not shown), such as bar codes, for recognition by the robotic handling system 458. For example, the robotic liquid handling system 458 may scan one or more inserts within each of the reagent cartridges 410 to confirm contents. In other implementations, machine-readable indicia may be marked upon each reagent cartridge 410, and a processing system (not shown, but see element 437 of FIG. 4B) of the automated multi-module cell editing instrument 400 may identify a stored materials map based upon the machine-readable indicia. In the embodiment illustrated in FIG. 4A, a cell growth module comprises a cell growth vial 418 (described in greater detail below in relation to FIGS. 5A-5D). Additionally seen is the TFF module 422 (described above in detail in relation to FIGS. 6A-6E) and selection module 420. Also illustrated as part of the automated multi-module cell processing instrument 400 of FIG. 4A is a singulation module 440 (e.g., a solid wall isolation, incubation and normalization device (SWIIN device) is shown here) described herein in relation to FIGS. 7A-7E, served by, e.g., robotic liquid handing system 458 and air displacement pipettor 432. Additionally seen is a selection module 420. Also note the placement of three heatsinks 455.

Figure 4B:
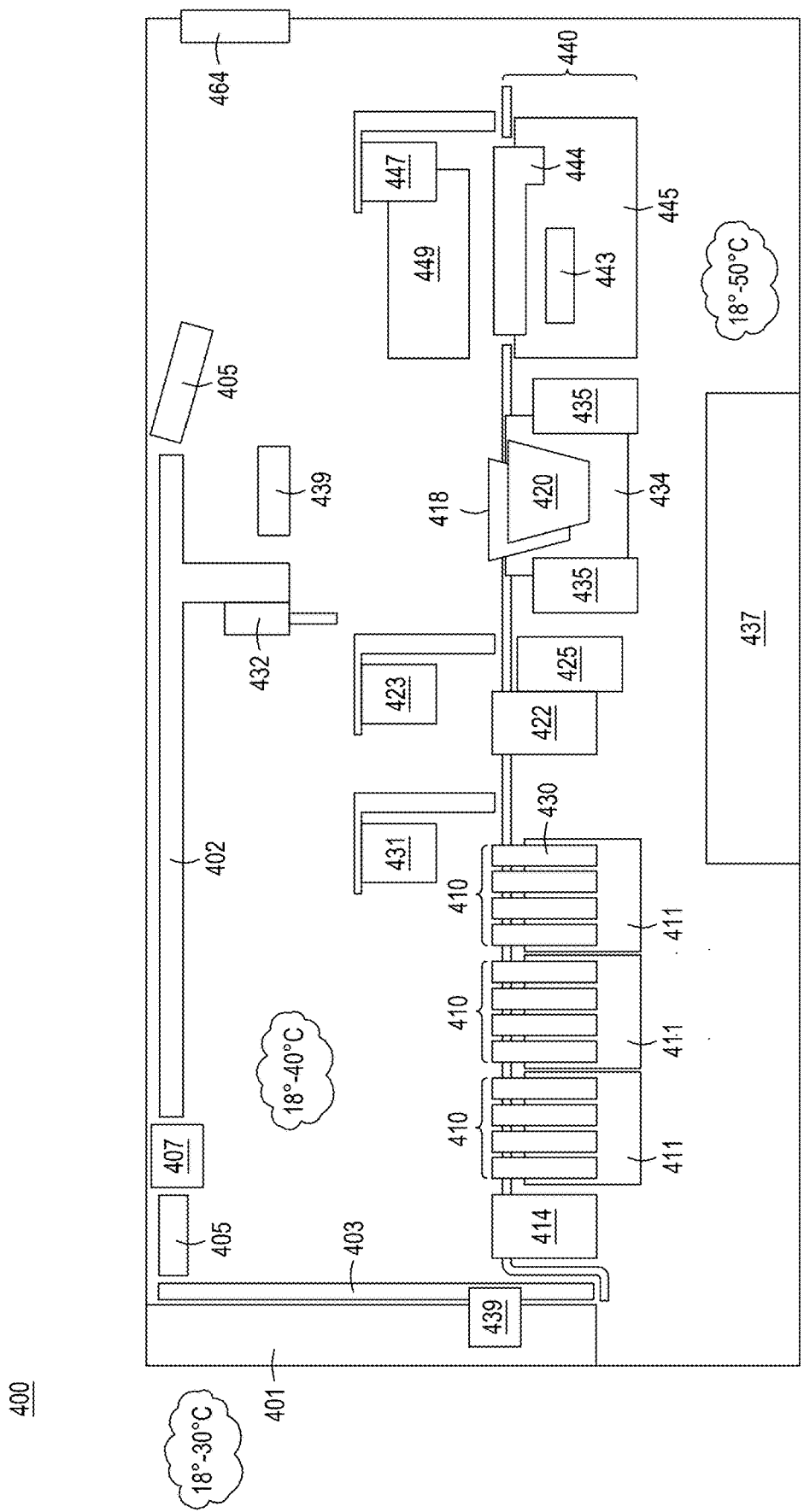

FIG. 4B is a simplified representation of the contents of the exemplary multi-module cell processing instrument 400 depicted in FIG. 4A. Cartridge-based source materials (such as in reagent cartridges 410), for example, may be positioned in designated areas on a deck of the instrument 400 for access by an air displacement pipettor 432. The deck of the multi-module cell processing instrument 400 may include a protection sink such that contaminants spilling, dripping, or overflowing from any of the modules of the instrument 400 are contained within a lip of the protection sink. Also seen are reagent cartridges 410, which are shown disposed with thermal assemblies 411 which can create temperature zones appropriate for different regions. Note that one of the reagent cartridges also comprises a flow-through electroporation device 430 (FTEP), served by FTEP interface (e.g., manifold arm) and actuator 431. Also seen is TFF module 422 with adjacent thermal assembly 425, where the TFF module is served by TFF interface (e.g., manifold arm) and actuator 433. Thermal assemblies 425, 435, and 445 encompass thermal electric devices such as Peltier devices, as well as heatsinks, fans and coolers. The rotating growth vial 418 is within a growth module 434, where the growth module is served by two thermal assemblies 435. A selection module is seen at 420. Also seen is the SWIIN module 440, comprising a SWIIN cartridge 441, where the SWIIN module also comprises a thermal assembly 445, illumination 443 (in this embodiment, backlighting), evaporation and condensation control 449, and where the SWIIN module is served by SWIIN interface (e.g., manifold arm) and actuator 447. Also seen in this view is touch screen display 401, display actuator 403, illumination 405 (one on either side of multi-module cell processing instrument 400), and cameras 439 (one illumination device on either side of multi-module cell processing instrument 400). Finally, element 437 comprises electronics, such as circuit control boards, high-voltage amplifiers, power supplies, and power entry; as well as pneumatics, such as pumps, valves and sensors.

Figure 4C:
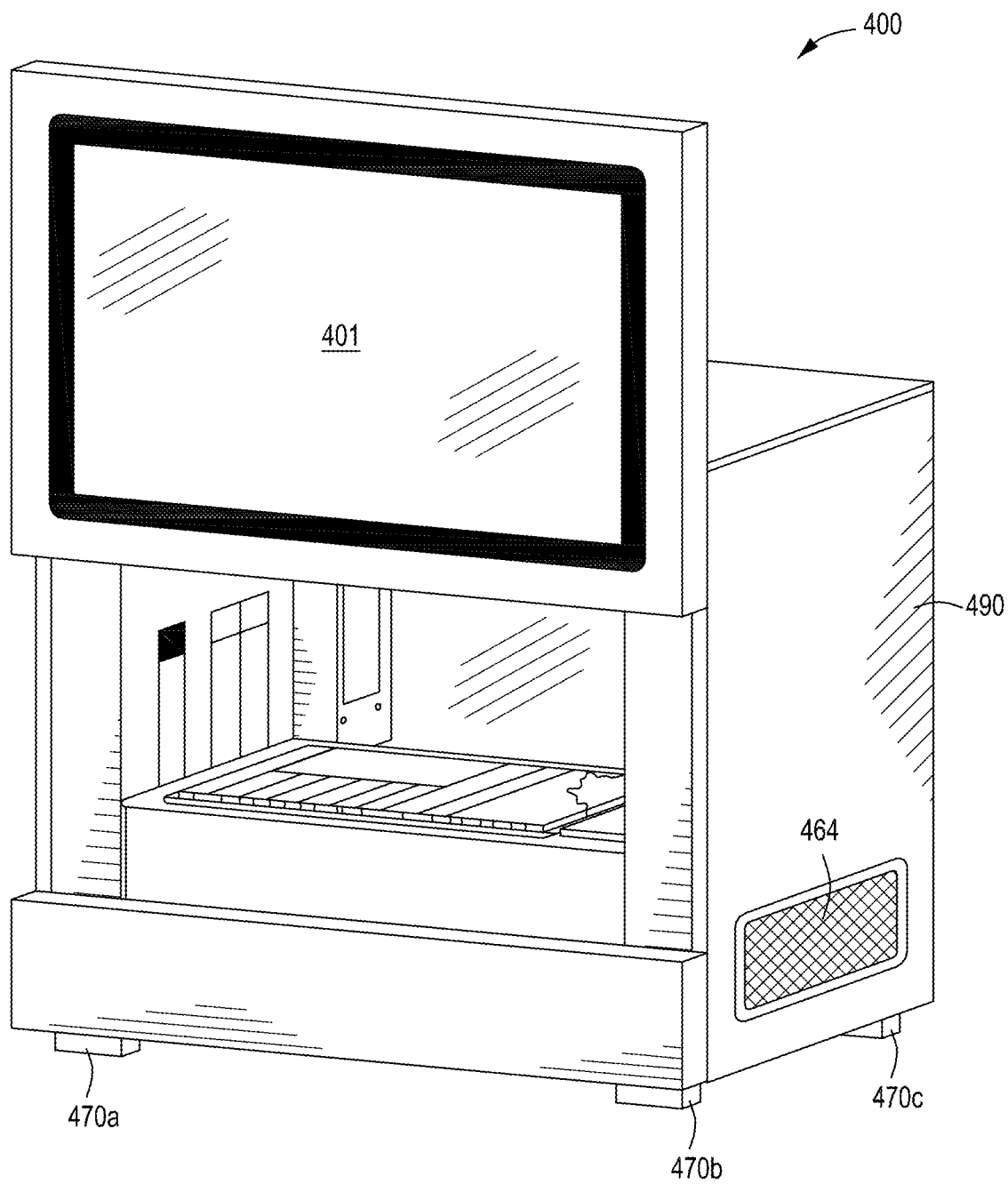

FIG. 4C illustrates a front perspective view of multi-module cell processing instrument 400 for use in as a desktop version of the automated multi-module cell editing instrument 400. For example, a chassis 490 may have a width of about 24-48 inches, a height of about 24-48 inches and a depth of about 24-48 inches. Chassis 490 may be and preferably is designed to hold all modules and disposable supplies used in automated cell processing and to perform all processes required without human intervention; that is, chassis 490 is configured to provide an integrated, stand-alone automated multi-module cell processing instrument. As illustrated in FIG. 4C, chassis 490 includes touch screen display 401, cooling grate 464, which allows for air flow via an internal fan (not shown). The touch screen display provides information to a user regarding the processing status of the automated multi-module cell editing instrument 400 and accepts inputs from the user for conducting the cell processing. In this embodiment, the chassis 490 is lifted by adjustable feet 470a, 470b, 470c and 470d (feet 470a-470c are shown in this FIG. 4C). Adjustable feet 470a-470d, for example, allow for additional air flow beneath the chassis 490.

Inside the chassis 490, in some implementations, will be most or all of the components described in relation to FIGS. 4A and 4B, including the robotic liquid handling system disposed along a gantry, reagent cartridges 410 including a flow-through electroporation device, a rotating growth vial 418 in a cell growth module 434, a tangential flow filtration module 422, a SWIIN module 440 as well as interfaces and actuators for the various modules. In addition, chassis 490 houses control circuitry, liquid handling tubes, air pump controls, valves, sensors, thermal assemblies (e.g., heating and cooling units) and other control mechanisms. For examples of multi-module cell editing instruments, see U.S. Pat. No. 10,253,316, issued 9 Apr. 2019; U.S. Pat. No.

10,329,559, issued 25 Jun. 2019; U.S. Pat. No. 10,323,242, issued 18 Jun. 2019; U.S. Pat. No. 10,421,959, issued 24 Sep. 2019; U.S. Pat. No. 10,465,185, issued 5 Nov. 2019; and U.S. Pat. No. 10,519,437, issued 31 Dec. 2019; and U.S. Ser. No. 16/666,964, filed 29 Oct. 2019; and Ser. No. 16/680,643, filed 12 Nov. 2019 all of which are herein incorporated by reference in their entirety.

Rotating Cell Growth Module

Figure 5A:
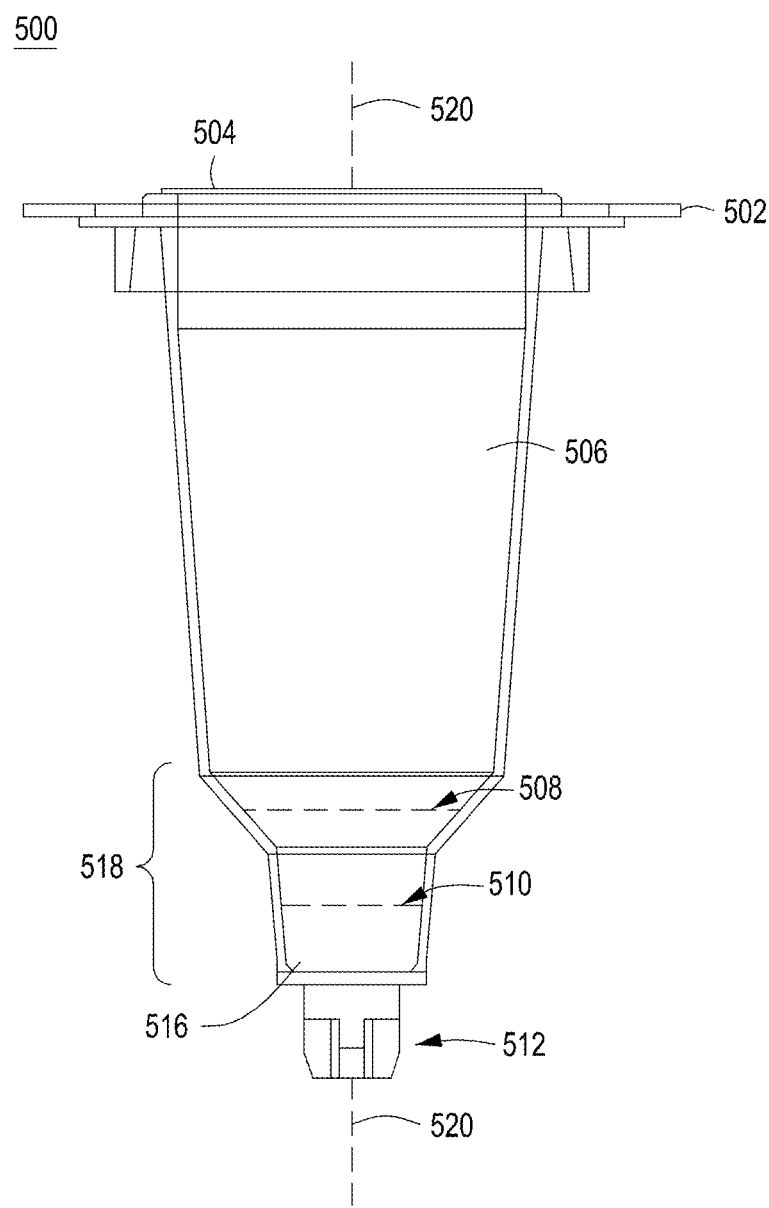
FIG. 5A depicts one embodiment of a rotating growth vial for use with a cell growth module.

FIG. 5A shows one embodiment of a rotating growth vial 500 for use with the cell growth device described herein. The rotating growth vial is an optically-transparent container having an open end 504 for receiving liquid media and cells, a central vial region 506 that defines the primary container for growing cells, a tapered-to-constricted region 518 defining at least one light path 510, a closed end 516, and a drive engagement mechanism 512. The rotating growth vial has a central longitudinal axis 520 around which the vial rotates, and the light path 510 is generally perpendicular to the longitudinal axis of the vial. The first light path 510 is positioned in the lower constricted portion of the tapered-to-constricted region 518. Optionally, some embodiments of the rotating growth vial 500 have a second light path 508 in the tapered region of the tapered-to-constricted region 518. Both light paths in this embodiment are positioned in a region of the rotating growth vial that is constantly filled with the cell culture (cells+growth media) and is not affected by the rotational speed of the growth vial. The first light path 510 is shorter than the second light path 508 allowing for sensitive measurement of OD values when the OD values of the cell culture in the vial are at a high level (e.g., later in the cell growth process), whereas the second light path 508 allows for sensitive measurement of OD values when the OD values of the cell culture in the vial are at a lower level (e.g., earlier in the cell growth process). Also shown is lip 502, which allows the rotating growth vial to be seated in a growth module (not shown) and further allows for easy handling by the user.

In some configurations of the rotating growth vial, the rotating growth vial has two or more "paddles" or interior features disposed within the rotating growth vial, extending from the inner wall of the rotating growth vial toward the center of the central vial region 506. In some aspects, the width of the paddles or features varies with the size or volume of the rotating growth vial, and may range from $1/20$ to just over $1/3$ the diameter of the rotating growth vial, or from $1/15$ to $1/4$ the diameter of the rotating growth vial, or from $1/10$ to $1/5$ the diameter of the rotating growth vial. In some aspects, the length of the paddles varies with the size or volume of the rotating growth vial, and may range from $4/5$ to $1/4$ the length of the main body of the rotating growth vial 500, or from $3/4$ to $1/3$ the length of the central body region 506 of the rotating growth vial, or from $1/2$ to $1/3$ the length of the central body region 506 of the rotating growth vial 500. In other aspects, there may be concentric rows of raised features disposed on the inner surface of the main body of the rotating growth vial arranged horizontally or vertically; and in other aspects, there may be a spiral configuration of raised features disposed on the inner surface of the main body of the rotating growth vial. In alternative aspects, the concentric rows of raised features or spiral configuration may be disposed upon a post or center structure of the rotating growth vial. Though described above as having two paddles, the rotating growth vial 500 may comprise 3, 4, 5, 6 or more paddles, and up to 20 paddles. The number of paddles will depend upon, e.g., the size or volume of the rotating growth vial 500. The paddles may be arranged symmetrically as single paddles extending from the inner wall of the vial into the interior of the vial, or the paddles may be symmetrically arranged in groups of 2, 3, 4 or more paddles in a group (for example, a pair of paddles opposite another pair of paddles) extending from the inner wall of the vial into the interior of the vial. In another embodiment, the paddles may extend from the middle of the rotating growth vial out toward the wall of the rotating growth vial, from, e.g., a post or other support structure in the interior of the rotating growth vial.

The drive engagement mechanism 512 engages with a motor (not shown) to rotate the vial. In some embodiments, the motor drives the drive engagement mechanism 512 such that the rotating growth vial is rotated in one direction only, and in other embodiments, the rotating growth vial is rotated in a first direction for a first amount of time or periodicity, rotated in a second direction (i.e., the opposite direction) for a second amount of time or periodicity, and this process may be repeated so that the rotating growth vial (and the cell culture contents) are subjected to an oscillating motion. Further, the choice of whether the culture is subject to oscillation and the periodicity therefor may be selected by the user. The first amount of time and the second amount of time may be the same or may be different. The amount of time may be 1, 2, 3, 4, 5, or more seconds, or may be 1, 2, 3, 4 or more minutes. In another embodiment, in an early stage of cell growth, the rotating growth vial may be oscillated at a first periodicity (e.g., every 60 seconds), and then at a later stage of cell growth, the rotating growth vial may be oscillated at a second periodicity (e.g., every one second) different from the first periodicity.

The rotating growth vial 500 may be reusable or, preferably, the rotating growth vial is consumable. In some embodiments, the rotating growth vial is consumable and is presented to the user pre-filled with growth medium, where the vial is hermetically sealed at the open end 504 with a foil or film seal. A medium-filled rotating growth vial packaged in such a manner may be part of a kit for use with a stand-alone cell growth device or with a cell growth module that is part of an automated multi-module cell processing instrument. To introduce cells into the vial, a user need only pipette up a desired volume of cells and use the pipette tip to punch through the foil or film seal of the vial. Open end 504 may optionally include an extended lip 502 to overlap and engage with the cell growth device (not shown). In automated systems, the rotating growth vial 500 may be tagged with a barcode or other identifying means that can be read by a scanner or camera that is part of the automated instrument (not shown).

The volume of the rotating growth vial 500 and the volume of the cell culture (including growth medium) may vary greatly, but the volume of the rotating growth vial 500 must be large enough for the cell culture in the growth vial to get proper aeration while the vial is rotating and to generate an adequate number of cells. In practice, the volume of the rotating growth vial 500 may range from 1-250 ml, 2-100 ml, from 5-80 ml, 10-50 ml, or from 12-35 ml. Likewise, the volume of the cell culture (cells+growth media) should be appropriate to allow proper aeration in the rotating growth vial. Thus, the volume of the cell culture should be approximately 5-85% of the volume of the growth vial or from 20-60% of the volume of the growth vial. For example, for a 35 ml growth vial, the volume of the cell culture would be from about 1.8 ml to about 27 ml, or from 5 ml to about 21 ml.

The rotating growth vial 500 preferably is fabricated from a bio-compatible optically transparent material or at least the portion of the vial comprising the light path(s) is transparent.

Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include glass, cyclic olefin copolymer (COC), polyvinyl chloride, polyethylene, polyamide, polypropylene, polycarbonate, poly(methyl methacrylate (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 5B:
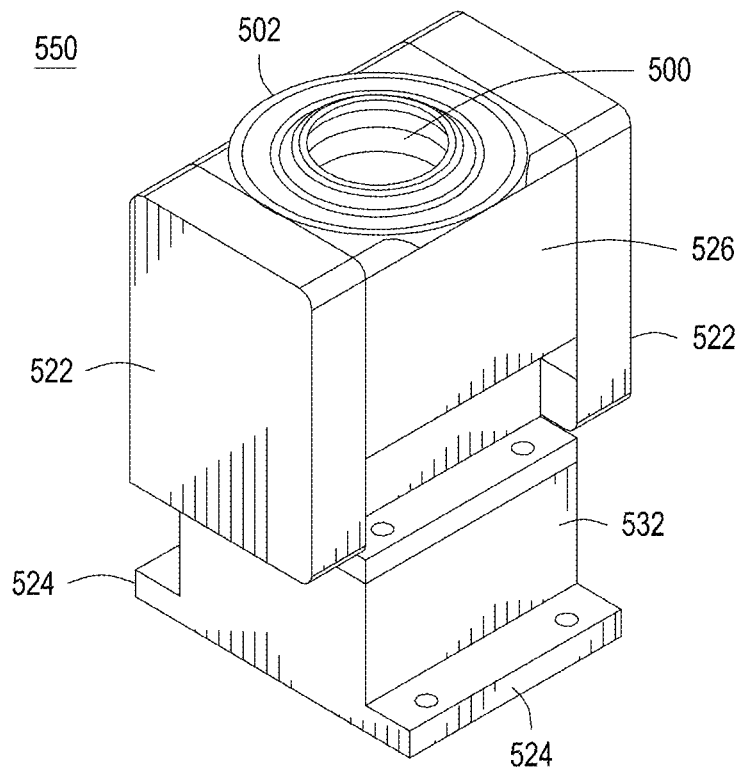
FIG. 5B illustrates a perspective view of one embodiment of a rotating growth vial in a cell growth module.
Figure 5C:
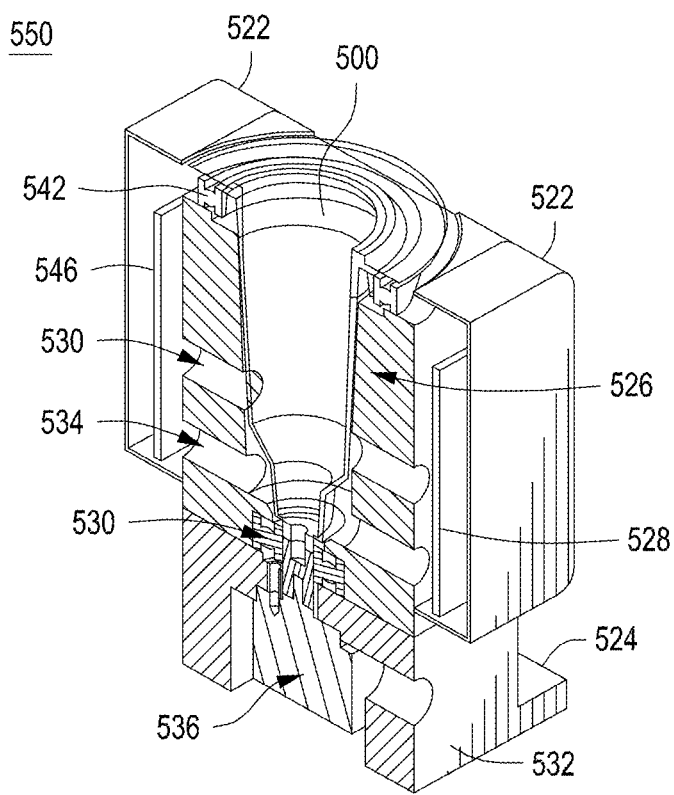
FIG. 5C depicts a cut-away view of the cell growth module from FIG. 5B.
Figure 5D:
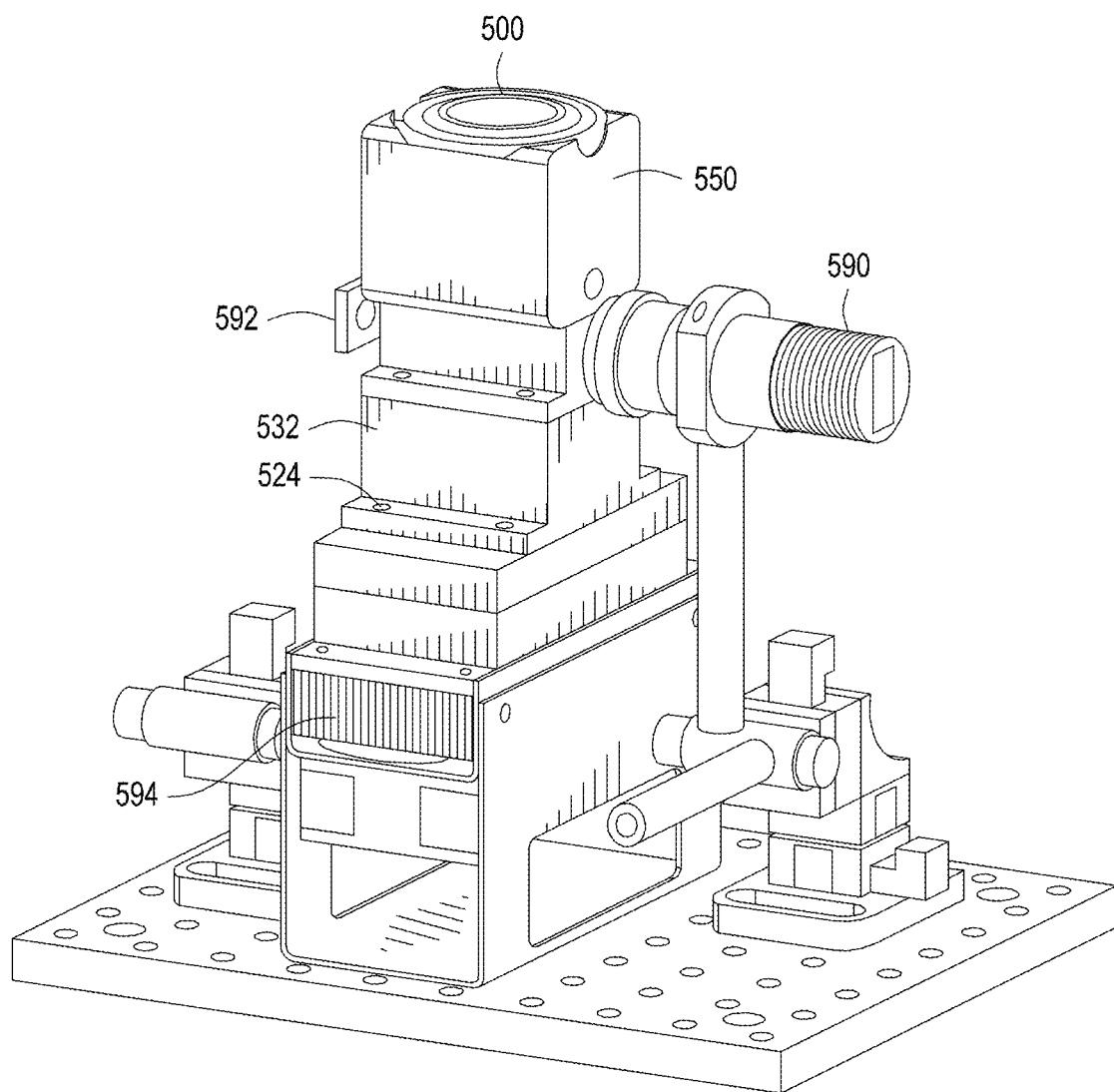
FIG. 5D illustrates the cell growth module of FIG. 5B coupled to LED, detector, and temperature regulating components.

FIGS. 5B-5D show an embodiment of a cell growth module 550 comprising a rotating growth vial 500. FIG. 5B is a perspective view of one embodiment of a cell growth module 550. FIG. 5C depicts a cut-away view of the cell growth module 550 from FIG. 5B. In both figures, the rotating growth vial 500 is seen positioned inside a main housing 526 with the extended lip 502 of the rotating growth vial 500 extending above the main housing 526. Additionally, end housings 522, a lower housing 532, and flanges 524 are indicated in both figures. Flanges 524 are used to attach the cell growth device/module to heating/cooling means or to another structure (not shown). FIG. 5C depicts additional detail. In FIG. 5C, upper bearing 542 and lower bearing 530 are shown positioned in main housing 526. Upper bearing 542 and lower bearing 530 support the vertical load of rotating growth vial 500. Lower housing 532 contains the drive motor 536. The cell growth device 550 of FIG. 5C comprises two light paths: a primary light path 534, and a secondary light path 530. Light path 534 corresponds to light path 510 positioned in the constricted portion of the tapered-to-constricted portion of the rotating growth vial, and light path 530 corresponds to light path 508 in the tapered portion of the tapered-to-constricted portion of the rotating growth vial. Light paths 510 and 508 are not shown in FIG. 5C but may be seen in, e.g., FIG. 5A. In addition to light paths 534 and 530, there is an emission board 528 to illuminate the light path(s), and detector board 546 to detect the light after the light travels through the cell culture liquid in the rotating growth vial 500.

The drive motor 536 used to rotate the rotating growth vial 500 in some embodiments is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the drive motor 506 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 526, end housings 522 and lower housing 532 of the cell growth device/module 550 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial 500 is envisioned in some embodiments to be reusable but preferably is consumable, the other components of the cell growth device 550 are preferably reusable and can function as a stand-alone benchtop device or, as here, as a module in a multi-module cell processing instrument.

The processor (not shown) of the cell growth system may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor of the cell growth system may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth system, where the second spectrophotometer is used to read a blank at designated intervals.

FIG. 5D illustrates a cell growth device/module 550 as part of an assembly comprising the cell growth device 550 of FIG. 5B coupled to light source 590, detector 592, and thermoelectric components 594. The rotating growth vial 500 is inserted into the cell growth device 550. Components of the light source 590 and detector 592 (e.g., such as a photodiode with gain control to cover 5-log) are coupled to the main housing of the cell growth device 550. The lower housing 532 that houses the motor that rotates the rotating growth vial is illustrated, as is one of the flanges 524 that secures the cell growth device to the assembly. Also illustrated is a Peltier device or thermoelectric component 594. In this embodiment, thermal control is accomplished by attachment and electrical integration of the cell growth device 500 to the thermoelectric component 594 via the flange 504 on the base of the lower housing 532. Thermoelectric coolers/devices 594 are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 500 is controlled to approximately +/−0.5° C.

In certain embodiments, a rear-mounted power entry module contains the safety fuses and the on-off switch, which when switched on powers the internal AC and DC power supplies (not shown) activating the processor. Measurements of optical densities (OD) at programmed time intervals are accomplished using a 600 nm Light Emitting Diode (LED) (not shown) that has been columnated through an optic into the lower constricted portion of the rotating growth vial which contains the cells of interest. The light continues through a collection optic to the detection system which consists of a (digital) gain-controlled silicone photodiode. Generally, optical density is normally shown as the absolute value of the logarithm with base 10 of the power transmission factors of an optical attenuator: OD=−log 10 (Power out/Power in). Since OD is the measure of optical attenuation—that is, the sum of absorption, scattering, and reflection—the cell growth device OD measurement records the overall power transmission, so as the cells grow and become denser in population, the OD (the loss of signal) increases. The OD system is pre-calibrated against OD standards with these values stored in an on-board memory accessible by the measurement program.

In use, cells are inoculated (cells can be pipetted, e.g., from an automated liquid handling system or by a user) into pre-filled growth media of a rotating growth vial 500 by piercing though the foil or film seal. The programmed software of the cell growth device 550 sets the control temperature for growth, typically 30° C., then slowly starts the rotation of the rotating growth vial. The cell/growth media mixture slowly moves vertically up the wall due to centrifugal force allowing the rotating growth vial to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 550 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 minutes. While the cell growth device has been described in the context of measuring the optical density (OD) of a growing cell culture, it should, however, be understood by a skilled artisan given the teachings of the present specification that other cell growth parameters can be measured in addition to or instead of cell culture OD. For example, spectroscopy using visible, UV, or near infrared (NIR) light allows monitoring the concentration of nutrients and/or wastes in the cell culture. Additionally, spectroscopic measurements may be used to quantify multiple chemical species simultaneously. Nonsymmetric chemical species may be quantified by identification of characteristic absorbance features in the NIR. Conversely, symmetric chemical species can be readily quantified using Raman spectroscopy. Many critical metabolites, such as glucose, glutamine, ammonia, and lactate have distinct spectral features in the IR, such that they may be easily quantified. The amount and frequencies of light absorbed by the sample can be correlated to the type and concentration of chemical species present in the sample. Each of these measurement types provides specific advantages. FT-NIR provides the greatest light penetration depth and can be used for thicker samples. FT-mid-IR (MIR) provides information that is more easily discernible as being specific for certain analytes as these wavelengths are closer to the fundamental IR absorptions. FT-Raman is advantageous when interference due to water is to be minimized. Other spectral properties can be measured via, e.g., dielectric impedence spectroscopy, visible fluorescence, fluorescence polarization, or luminescence. Additionally, the cell growth device may include additional sensors for measuring, e.g., dissolved oxygen, carbon dioxide, pH, conductivity, and the like.

Cell Concentration Module

As described above in relation to the rotating growth vial and cell growth module, in order to obtain an adequate number of cells for transformation or transfection, cells typically are grown to a specific optical density in medium appropriate for the growth of the cells of interest; however, for effective transformation or transfection, it is desirable to decrease the volume of the cells as well as render the cells competent via buffer or medium exchange. Thus, one subcomponent or module that is desired in cell processing systems for the processes listed above is a module or component that can grow, perform buffer exchange, and/or concentrate cells and render them competent so that they may be transformed or transfected with the nucleic acids needed for engineering or editing the cell's genome.

Figure 6A:
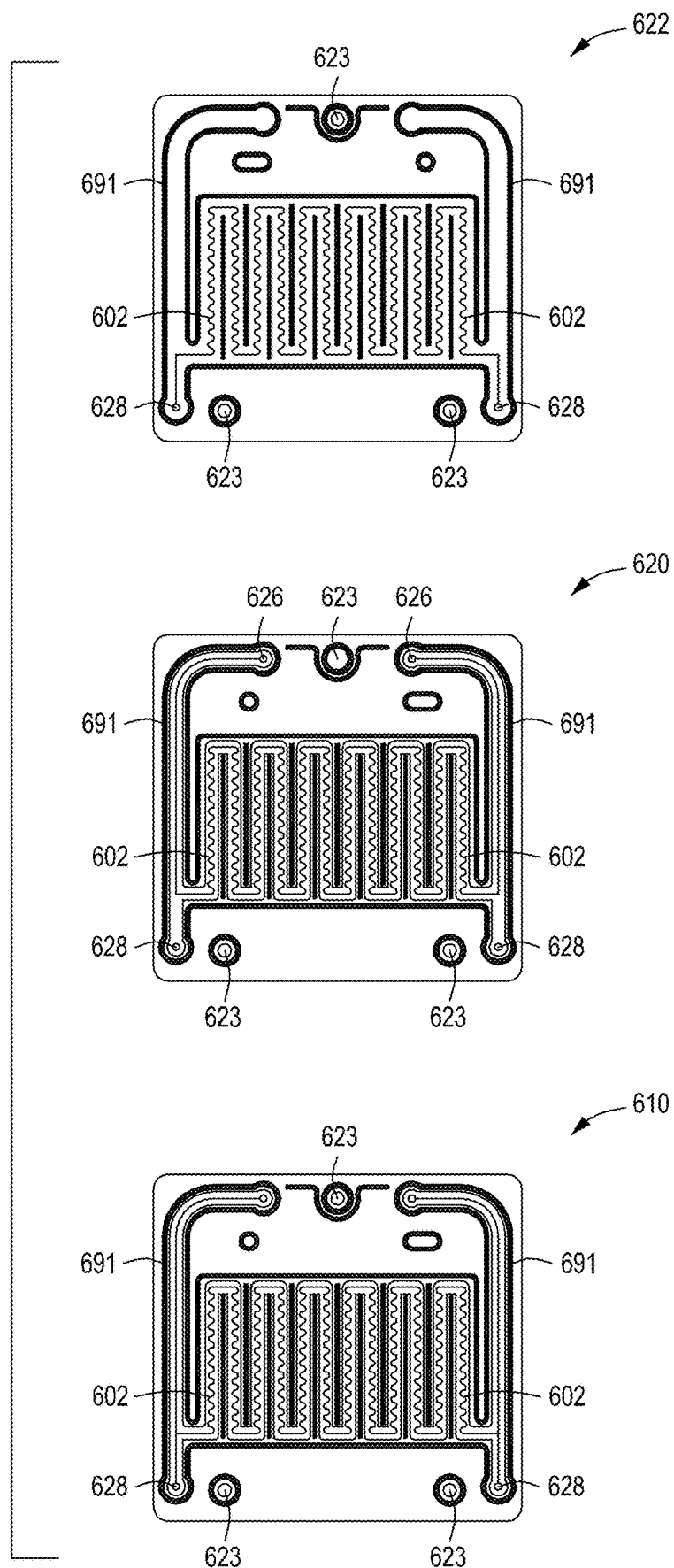
FIG. 6A depicts retentate (top) and permeate (bottom) members for use in a tangential flow filtration module (e.g., cell growth and/or concentration module), as well as the retentate and permeate members assembled into a tangential flow assembly (bottom).

FIG. 6A shows a retentate member 622 (*top*), permeate member 620 (middle) and a tangential flow assembly 610 (bottom) comprising the retentate member 622, membrane 624 (not seen in FIG. 6A), and permeate member 620 (also not seen). In FIG. 6A, retentate member 622 comprises a tangential flow channel 602, which has a serpentine configuration that initiates at one lower corner of retentate member 622 specifically at retentate port 628—traverses across and up then down and across retentate member 622, ending in the other lower corner of retentate member 622 at a second retentate port 628. Also seen on retentate member 622 are energy directors 691, which circumscribe the region where a membrane or filter (not seen in this FIG. 6A) is seated, as well as interdigitate between areas of channel 602. Energy directors 691 in this embodiment mate with and serve to facilitate ultrasonic welding or bonding of retentate member 622 with permeate/filtrate member 620 via the energy director component 691 on permeate/filtrate member 620 (at right). Additionally, countersinks 623 can be seen, two on the bottom one at the top middle of retentate member 622. Countersinks 623 are used to couple and tangential flow assembly 610 to a reservoir assembly (not seen in this FIG. 6A but see FIG. 6B).

Permeate/filtrate member 620 is seen in the middle of FIG. 6A and comprises, in addition to energy director 691, through-holes for retentate ports 628 at each bottom corner (which mate with the through-holes for retentate ports 628 at the bottom corners of retentate member 622), as well as a tangential flow channel 602 and two permeate/filtrate ports 626 positioned at the top and center of permeate member 620. The tangential flow channel 602 structure in this embodiment has a serpentine configuration and an undulating geometry, although other geometries may be used. Permeate member 620 also comprises countersinks 623, coincident with the countersinks 623 on retentate member 620.

At bottom of FIG. 6A is a tangential flow assembly 610 comprising the retentate member 622 positioned on top of an assembled with permeate member 620. In this view, retentate member 622 is "on top" of the view, a membrane (not seen in this view of the assembly) would be adjacent and under retentate member 622 and permeate member 620 (also not seen in this view of the assembly) is adjacent to and beneath the membrane. Again countersinks 623 are seen, where the countersinks in the retentate member 622 and the permeate member 620 are coincident and configured to mate with threads or mating elements for the countersinks disposed on a reservoir assembly (not seen in FIG. 6A but see FIG. 6B).

A membrane or filter is disposed between the retentate and permeate members, where fluids can flow through the membrane but cells cannot and are thus retained in the flow channel disposed in the retentate member. Filters or membranes appropriate for use in the TFF device/module are those that are solvent resistant, are contamination free during filtration, and are able to retain the types and sizes of cells of interest. For example, in order to retain small cell types such as bacterial cells, pore sizes can be as low as 0.2 µm, however for other cell types, the pore sizes can be as high as 20 m. Indeed, the pore sizes useful in the TFF device/module include filters with sizes from 0.20 μm, 0.21 μm, 0.22 μm, 0.23 μm, 0.24 μm, 0.25 μm, 0.26 μm, 0.27 μm, 0.28 m, 0.29 μm, 0.30 μm, 0.31 μm, 0.32 μm, 0.33 μm, 0.34 μm, 0.35 μm, 0.36 μm, 0.37 μm, 0.38 μm, 0.39 μm, 0.40 μm, 0.41 μm, 0.42 μm, 0.43 μm, 0.44 μm, 0.45 μm, 0.46 μm, 0.47 μm, 0.48 μm, 0.49 μm, 0.50 μm and larger. The filters may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching.

The length of the channel structure 602 may vary depending on the volume of the cell culture to be grown and the optical density of the cell culture to be concentrated. The length of the channel structure typically is from 60 mm to 300 mm, or from 70 mm to 200 mm, or from 80 mm to 100 mm. The cross-section configuration of the flow channel 402 may be round, elliptical, oval, square, rectangular, trapezoidal, or irregular. If square, rectangular, or another shape with generally straight sides, the cross section may be from about 10 μm to 1000 μm wide, or from 200 μm to 800 μm wide, or from 300 μm to 700 μm wide, or from 400 μm to 600 μm wide; and from about 10 μm to 1000 m high, or from 200 μm to 800 μm high, or from 300 μm to 700 μm high, or from 400 m to 600 μm high. If the cross section of the flow channel 102 is generally round, oval or elliptical, the radius of the channel may be from about 50 μm to 1000 μm in hydraulic radius, or from 5 μm to 800 μm in hydraulic radius, or from 200 μm to 700 μm in hydraulic radius, or from 300 μm to 600 μm wide in hydraulic radius, or from about 200 to 500 μm in hydraulic radius. Moreover, the volume of the channel in the retentate 422 and permeate 620 members may be different depending on the depth of the channel in each member.

Figure 6B:
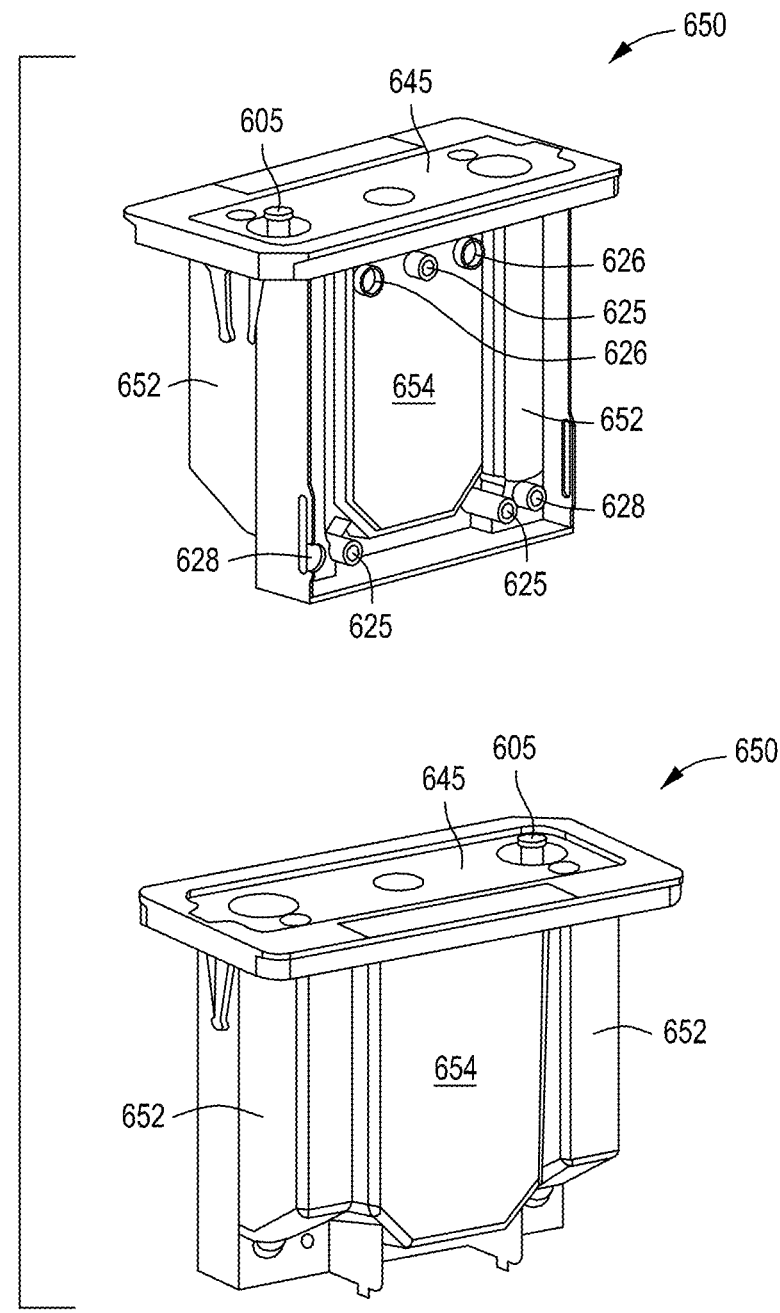
FIG. 6B depicts two side perspective views of a reservoir assembly of a tangential flow filtration module.

FIG. 6B shows front perspective (upper figure) and rear perspective (lower figure) views of a reservoir assembly 650 configured to be used with the tangential flow assembly 610 seen in FIG. 6A. Seen in the front perspective view (e.g., "front" being the side of reservoir assembly 650 that is coupled to the tangential flow assembly 610 seen in FIG. 6A) are retentate reservoirs 652 on either side of permeate reservoir 654. Also seen are permeate ports 626, retentate ports 628, and three threads or mating elements 625 for countersinks 623 (countersinks 623 not seen in this FIG. 6B). Threads or mating elements 625 for countersinks 623 are configured to mate or couple the tangential flow assembly 610 (seen in FIG. 6A) to reservoir assembly 650. Alternatively or in addition, fasteners, sonic welding or heat stakes may be used to mate or couple the tangential flow assembly 610 to reservoir assembly 650. In addition is seen gasket 645 covering the top of reservoir assembly 650. Gasket 645 is described in detail in relation to FIG. 6E. At left in FIG. 6B is a rear perspective view of reservoir assembly 650, where "rear" is the side of reservoir assembly 650 that is not coupled to the tangential flow assembly. Seen are retentate reservoirs 652, permeate reservoir 654, and gasket 645.

The TFF device may be fabricated from any robust material in which channels (and channel branches) may be milled including stainless steel, silicon, glass, aluminum, or plastics including cyclic-olefin copolymer (COC), cyclo-olefin polymer (COP), polystyrene, polyvinyl chloride, polyethylene, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF device/module is disposable, preferably it is made of plastic. In some embodiments, the material used to fabricate the TFF device/module is thermally-conductive so that the cell culture may be heated or cooled to a desired temperature. In certain embodiments, the TFF device is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to this mass production techniques.

Figure 6C:
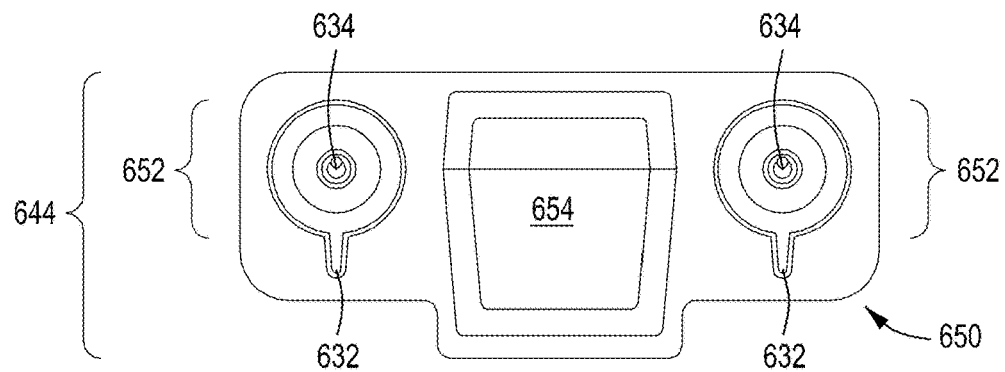
FIGS. 6C-6E depict an exemplary top, with fluidic and pneumatic ports and gasket suitable for the reservoir assemblies shown in FIG. 6B.
Figure 6D:
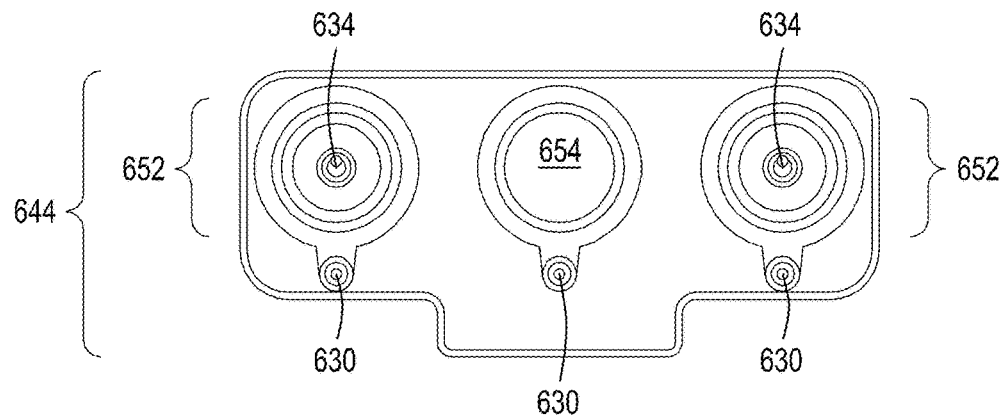
Figure 6E:
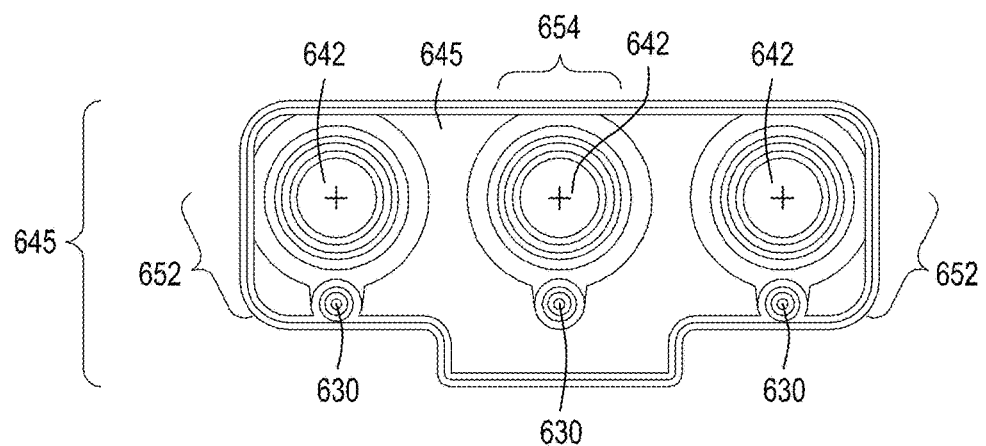

FIG. 6C depicts a top-down view of the reservoir assemblies 650 shown in FIG. 6B. FIG. 6D depicts a cover 644 for reservoir assembly 650 shown in FIGS. 6B and 6E depicts a gasket 645 that in operation is disposed on cover 644 of reservoir assemblies 650 shown in FIG. 6B. FIG. 6C is a top-down view of reservoir assembly 650, showing the tops of the two retentate reservoirs 652, one on either side of permeate reservoir 654. Also seen are grooves 632 that will mate with a pneumatic port (not shown), and fluid channels 634 that reside at the bottom of retentate reservoirs 652, which fluidically couple the retentate reservoirs 652 with the retentate ports 628 (not shown), via the through-holes for the retentate ports in permeate member 620 and membrane 624 (also not shown). FIG. 6D depicts a cover 644 that is configured to be disposed upon the top of reservoir assembly 650. Cover 644 has round cut-outs at the top of retentate reservoirs 652 and permeate/filtrate reservoir 654. Again at the bottom of retentate reservoirs 652 fluid channels 634 can be seen, where fluid channels 634 fluidically couple retentate reservoirs 652 with the retentate ports 628 (not shown). Also shown are three pneumatic ports 630 for each retentate reservoir 652 and permeate/filtrate reservoir 654. FIG. 6E depicts a gasket 645 that is configures to be disposed upon the cover 644 of reservoir assembly 650. Seen are three fluid transfer ports 642 for each retentate reservoir 652 and for permeate/filtrate reservoir 654. Again, three pneumatic ports 630, for each retentate reservoir 652 and for permeate/filtrate reservoir 654, are shown.

The overall work flow for cell growth comprises loading a cell culture to be grown into a first retentate reservoir, optionally bubbling air or an appropriate gas through the cell culture, passing or flowing the cell culture through the first retentate port then tangentially through the TFF channel structure while collecting medium or buffer through one or both of the permeate ports 606, collecting the cell culture through a second retentate port 604 into a second retentate reservoir, optionally adding additional or different medium to the cell culture and optionally bubbling air or gas through the cell culture, then repeating the process, all while measuring, e.g., the optical density of the cell culture in the retentate reservoirs continuously or at desired intervals. Measurements of optical densities (OD) at programmed time intervals are accomplished using a 600 nm Light Emitting Diode (LED) that has been columnated through an optic into the retentate reservoir(s) containing the growing cells. The light continues through a collection optic to the detection system which consists of a (digital) gain-controlled silicone photodiode. Generally, optical density is shown as the absolute value of the logarithm with base 10 of the power transmission factors of an optical attenuator: OD=−log 10 (Power out/Power in). Since OD is the measure of optical attenuation—that is, the sum of absorption, scattering, and reflection—the TFF device OD measurement records the overall power transmission, so as the cells grow and become denser in population, the OD (the loss of signal) increases. The OD system is pre-calibrated against OD standards with these values stored in an on-board memory accessible by the measurement program.

In the channel structure, the membrane bifurcating the flow channels retains the cells on one side of the membrane (the retentate side 622) and allows unwanted medium or buffer to flow across the membrane into a filtrate or permeate side (e.g., permeate member 620) of the device. Bubbling air or other appropriate gas through the cell culture both aerates and mixes the culture to enhance cell growth. During the process, medium that is removed during the flow through the channel structure is removed through the permeate/filtrate ports 606. Alternatively, cells can be grown in one reservoir with bubbling or agitation without passing the cells through the TFF channel from one reservoir to the other.

The overall workflow for cell concentration using the TFF device/module involves flowing a cell culture or cell sample tangentially through the channel structure. As with the cell growth process, the membrane bifurcating the flow channels retains the cells on one side of the membrane and allows unwanted medium or buffer to flow across the membrane into a permeate/filtrate side (e.g., permeate member 620) of the device. In this process, a fixed volume of cells in medium or buffer is driven through the device until the cell sample is collected into one of the retentate ports 604, and the medium/buffer that has passed through the membrane is collected through one or both of the permeate/filtrate ports 606. All types of prokaryotic and eukaryotic cells-both adherent and non-adherent cells—can be grown in the TFF device. Adherent cells may be grown on beads or other cell scaffolds suspended in medium that flow through the TFF device.

The medium or buffer used to suspend the cells in the cell concentration device/module may be any suitable medium or buffer for the type of cells being transformed or transfected, such as LB, SOC, TPD, YPG, YPAD, MEM, DMEM, IMDM, RPMI, Hanks', PBS and Ringer's solution, where the media may be provided in a reagent cartridge as part of a kit. For culture of adherent cells, cells may be disposed on beads, microcarriers, or other type of scaffold suspended in medium. Most normal mammalian tissue-derived cells—except those derived from the hematopoietic system—are anchorage dependent and need a surface or cell culture support for normal proliferation. In the rotating growth vial described herein, microcarrier technology is leveraged. Microcarriers of particular use typically have a diameter of 100-300 μm and have a density slightly greater than that of the culture medium (thus facilitating an easy separation of cells and medium for, e.g., medium exchange) yet the density must also be sufficiently low to allow complete suspension of the carriers at a minimum stirring rate in order to avoid hydrodynamic damage to the cells. Many different types of microcarriers are available, and different microcarriers are optimized for different types of cells. There are positively charged carriers, such as Cytodex 1 (dextran-based, GE Healthcare), DE-52 (cellulose-based, Sigma-Aldrich Labware), DE-53 (cellulose-based, Sigma-Aldrich Labware), and HLX 11-170 (polystyrene-based); collagen- or ECM—(extracellular matrix) coated carriers, such as Cytodex 3 (dextran-based, GE Healthcare) or HyQ-sphere Pro-F 102-4 (polystyrene-based, Thermo Scientific); non-charged carriers, like HyQ-sphere P 102-4 (Thermo Scientific); or macroporous carriers based on gelatin (Cultisphere, Percell Biolytica) or cellulose (Cytopore, GE Healthcare).

In both the cell growth and concentration processes, passing the cell sample through the TFF device and collecting the cells in one of the retentate ports 604 while collecting the medium in one of the permeate/filtrate ports 606 is considered "one pass" of the cell sample. The transfer between retentate reservoirs "flips" the culture. The retentate and permeatee ports collecting the cells and medium, respectively, for a given pass reside on the same end of TFF device/module with fluidic connections arranged so that there are two distinct flow layers for the retentate and permeate/filtrate sides, but if the retentate port 604 resides on the retentate member of device/module (that is, the cells are driven through the channel above the membrane and the filtrate (medium) passes to the portion of the channel below the membrane), the permeate/filtrate port 606 will reside on the permeate member of device/module and vice versa (that is, if the cell sample is driven through the channel below the membrane, the filtrate (medium) passes to the portion of the channel above the membrane). Due to the high pressures used to transfer the cell culture and fluids through the flow channel of the TFF device, the effect of gravity is negligible.

At the conclusion of a "pass" in either of the growth and concentration processes, the cell sample is collected by passing through the retentate port 604 and into the retentate reservoir (not shown). To initiate another "pass", the cell sample is passed again through the TFF device, this time in a flow direction that is reversed from the first pass. The cell sample is collected by passing through the retentate port 604 and into retentate reservoir (not shown) on the opposite end of the device/module from the retentate port 604 that was used to collect cells during the first pass. Likewise, the medium/buffer that passes through the membrane on the second pass is collected through the permeate port 606 on the opposite end of the device/module from the permeate port 606 that was used to collect the filtrate during the first pass, or through both ports. This alternating process of passing the retentate (the concentrated cell sample) through the device/module is repeated until the cells have been grown to a desired optical density, and/or concentrated to a desired volume, and both permeate ports (i.e., if there are more than one) can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell growth may (and typically do) take place simultaneously, and buffer exchange and cell concentration may (and typically do) take place simultaneously. For further information and alternative embodiments on TFFs see, e.g., U.S. Ser. No. 16/516, 701, filed 5 Sep. 2019.

As an alternative to the TFF module described above, a cell concentration module comprising a hollow filter may be employed. Examples of filters suitable for use in the present disclosure include membrane filters, ceramic filters and metal filters. The filter may be used in any shape; the filter may, for example, be cylindrical or essentially flat. Preferably, the filter used is a membrane filter, most preferably a hollow fiber filter. The term "hollow fiber" is meant to include a tubular membrane. The internal diameter of the tube is at least 0.1 mm, more preferably at least 0.5 mm, most preferably at least 0.75 mm and preferably the internal diameter of the tube is at most 10 mm, more preferably at most 6 mm, most preferably at most 1 mm. Filter modules comprising hollow fibers are commercially available from various companies, including G.E. Life Sciences (Marlborough, Mass.) and InnovaPrep (Drexel, Mo.). Specific examples of hollow fiber filter systems that can be used, modified or adapted for use in the present methods and systems include, but are not limited to, U.S. Pat. Nos. 9,738,918; 9,593,359; 9,574,977; 9,534,989; 9,446,354; 9,295,824; 8,956,880; 8,758,623; 8,726,744; 8,677,839; 8,677,840; 8,584,536; 8,584,535; and 8,110,112.

Nucleic Acid Assembly Module

Certain embodiments of the automated multi-module cell editing instruments comprising FTEPs of the present disclosure optionally include a nucleic acid assembly module. The nucleic acid assembly module is configured to accept and assemble the nucleic acids necessary to be porated into desired cells using the FTEP and to facilitate the desired genome editing events. In general, the term "vector" refers to a nucleic acid molecule capable of transporting a desired nucleic acid to which it has been linked into a cell. Vectors include, but are not limited to, nucleic acid molecules that are single-stranded, double-stranded, or partially double-stranded; nucleic acid molecules that include one or more free ends, no free ends (e.g., circular); nucleic acid molecules that include DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, where virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors" or "editing vectors." Common expression vectors of utility in recombinant DNA techniques are often in the form of plasmids. Additional vectors include fosmids, phagemids, BACs, YACs, and other synthetic chromosomes.

Recombinant expression vectors can include a nucleic acid in a form suitable for transcription, and for some nucleic acid sequences, translation and expression of the nucleic acid in a host cell, which means that the recombinant expression vectors include one or more regulatory elements-which may be selected on the basis of the host cells to be used for expression—that are operatively-linked to the nucleic acid sequence to be expressed. Within a recombinant expression vector, "operably linked" is intended to mean that the nucleotide sequence of interest is linked to the regulatory element(s) in a manner that allows for transcription, and for some nucleic acid sequences, translation and expression of the nucleotide sequence (e.g., in an in vitro transcription/translation system or in a host cell when the vector is introduced into the host cell). Appropriate recombination and cloning methods are disclosed in US Pub. No. 2004/0171156, the contents of which are herein incorporated by reference in their entirety for all purposes.

In some embodiments, a regulatory element is operably linked to one or more elements of a targetable nuclease system so as to drive transcription, and for some nucleic acid sequences, translation and expression of the one or more components of the targetable nuclease system.

In addition, the polynucleotide sequence encoding the nucleic acid-guided nuclease can be codon optimized for expression in particular cells, such as prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammal including non-human primate. In addition or alternatively, a vector may include a regulatory element operably linked to a polynucleotide sequence, which, when transcribed, forms a guide RNA.

The nucleic acid assembly module can be configured to perform a wide variety of different nucleic acid assembly techniques in an automated fashion. Nucleic acid assembly techniques that can be performed in the nucleic acid assembly module of the disclosed automated multi-module cell editing instruments include, but are not limited to, those assembly methods that use restriction endonucleases, including PCR, BioBrick assembly (U.S. Pat. No. 9,361,427), Type IIS cloning (e.g., GoldenGate assembly, European Patent Application Publication EP 2 395 087 A1), and Ligase Cycling Reaction (de Kok, ACS Synth Biol., 3(2): 97-106 (2014); Engler, et al., PLoS One, 3(11):e3647 (2008); and U.S. Pat. No. 6,143,527). In other embodiments, the nucleic acid assembly techniques performed by the disclosed automated multi-module cell editing instruments are based on overlaps between adjacent parts of the nucleic acids, such as Gibson Assembly®, CPEC, SLIC, Ligase Cycling etc. Additional assembly methods include gap repair in yeast (Bessa, Yeast, 29(10):419-23 (2012)), gateway cloning (Ohtsuka, Curr Pharm Biotechnol, 10(2):244-51 (2009)); U.S. Pat. No. 5,888,732; and 6,277,608), and topoisomerase-mediated cloning (Udo, PLoS One, 10(9): e0139349 (2015); and U.S. Pat. No. 6,916,632). These and other nucleic acid assembly techniques are described, e.g., in Sands and Brent, Curr Protoc Mol Biol., 113:3.26.1-3.26.20 (2016).

The nucleic acid assembly module is temperature controlled depending upon the type of nucleic acid assembly used in the automated multi-module cell editing instrument. For example, when PCR is utilized in the nucleic acid assembly module, the module includes a thermocycling capability allowing the temperatures to cycle between denaturation, annealing and extension steps. When single temperature assembly methods (e.g., isothermal assembly methods) are utilized in the nucleic acid assembly module, the module provides the ability to reach and hold at the temperature that optimizes the specific assembly process being performed. These temperatures and the duration for maintaining these temperatures can be determined by a preprogrammed set of parameters executed by a script, or manually controlled by the user using the processing system of the automated multi-module cell editing instrument.

In one embodiment, the nucleic acid assembly module is a module to perform assembly using a single, isothermal reaction. Certain isothermal assembly methods can combine simultaneously up to 15 nucleic acid fragments based on sequence identity. The assembly method provides, in some embodiments, nucleic acids to be assembled which include an approximate 20-40 base overlap with adjacent nucleic acid fragments. The fragments are mixed with a cocktail of three enzymes—an exonuclease, a polymerase, and a ligase— along with buffer components. Because the process is isothermal and can be performed in a 1-step or 2-step method using a single reaction vessel, isothermal assembly reactions are ideal for use in an automated multi-module cell editing instrument. The 1-step method allows for the assembly of up to five different fragments using a single step isothermal process. The fragments and the master mix of enzymes are combined and incubated at 50° C. for up to one hour. For the creation of more complex constructs with up to fifteen fragments or for incorporating fragments from 100 bp up to 10 kb, typically the 2-step is used, where the 2-step reaction requires two separate additions of master mix; one for the exonuclease and annealing step and a second for the polymerase and ligation steps.

Cell Enrichment Module

One optional aspect of the present disclosure provides automated modules and instruments for nucleic acid-guided nuclease genome editing that implement enrichment techniques for cells whose genomes have been properly edited. The enrichment module performs methods that use cell singulation and normalization to reduce growth competition between edited and unedited cells or utilizes methods that take advantage of inducing editing at a specific time during cell growth. Singulation overcomes growth bias from unedited cells or cells containing edits conferring growth advantages or disadvantages. The methods, modules and instruments may be applied to all cell types including, archaeal, prokaryotic, and eukaryotic (e.g., yeast, fungal, plant and animal) cells.

Singulating or substantially singulating, induction of editing, and normalization of cell colonies leads to 2-250×, 10-225×, 25-200×, 40-175×, 50-150×, 60-100×, or 5-100× gains in identifying edited cells over prior art methods and generates arrayed or pooled edited cells comprising genome libraries. Additionally, the methods, modules, and instruments may be leveraged to create iterative editing systems to generate combinatorial libraries, identify rare cell edits, and enable high-throughput enrichment applications to identify editing activity.

Figure 7A:
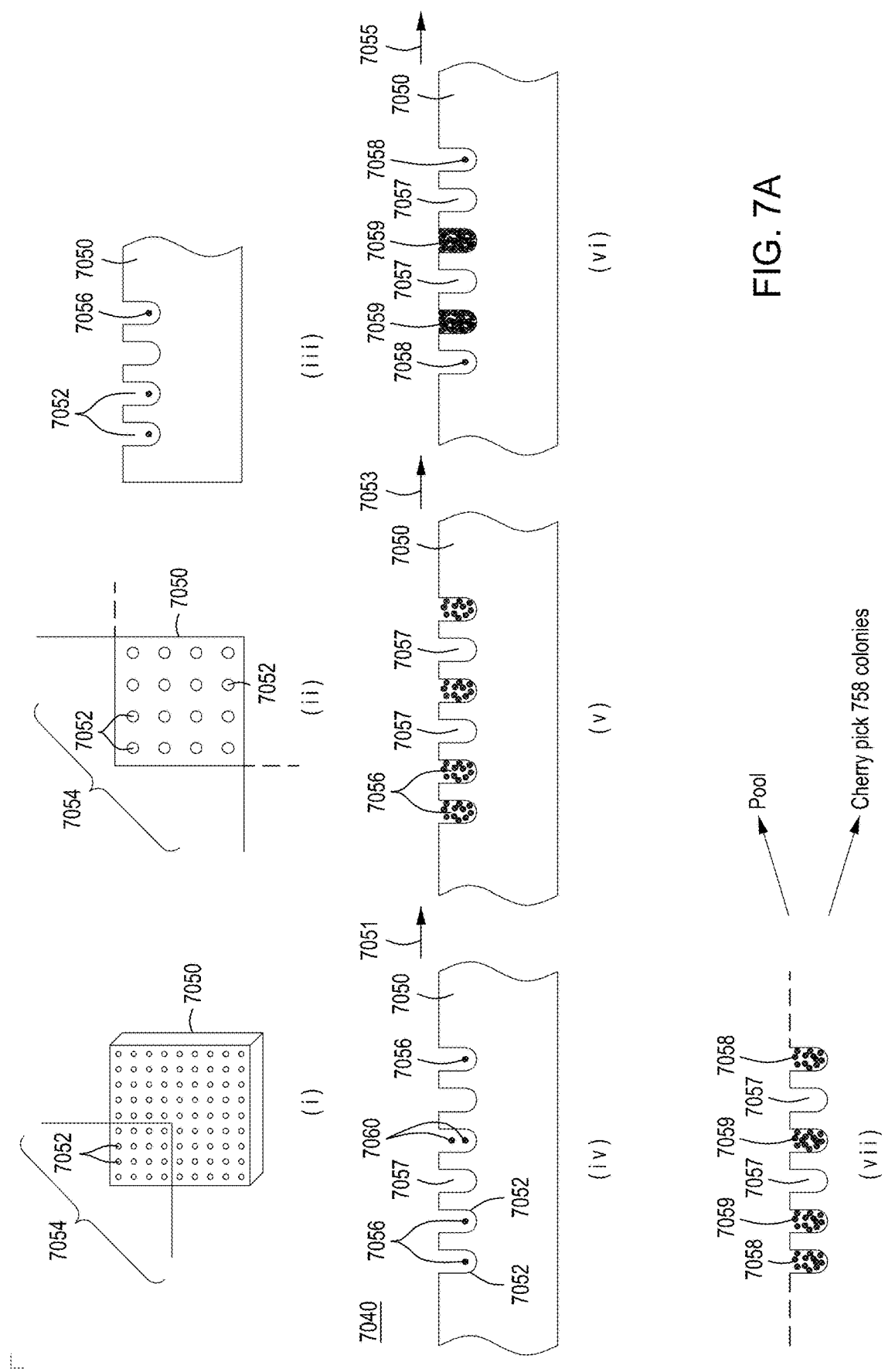
FIG. 7A depicts a simplified graphic of a workflow for singulating, editing and normalizing cells.

The compositions and methods described herein improve nucleic acid-guided nuclease editing systems in which nucleic acid-guided nucleases (e.g., RNA-guided nucleases) are used to edit specific target regions in an organism's genome. FIG. 7A depicts a solid wall device 7050 and a workflow for singulating cells in microwells in the solid wall device, where in this workflow one or both of the gRNA and nuclease are under the control of an inducible promoter. At the top left of the figure (i), there is depicted solid wall device 7050 with microwells 7052. A section 7054 of solid wall device 7050 is shown at (ii), also depicting microwells 7052. At (iii), a side cross-section of solid wall device 7050 is shown, and microwells 7052 have been loaded, where, in this embodiment, Poisson loading has taken place; that is, each microwell has one (e.g., microwells 7052, 7056) or no cells, and the likelihood that any one microwell has more than one cell is low. Note, however, that in alternative embodiments substantial singulation-partitioning cells into small "groups" of less than 20 cells per partition, and more preferably less than 10 cells per partition—may be performed depending on the plexity of the library. At (iv), workflow 7040 is illustrated where substrate 7050 having microwells 7052 shows microwells 7056 with one cell per microwell, microwells 7057 with no cells in the microwells, and one microwell 7060 with two cells in the microwell. In step 7051, the cells in the microwells are allowed to double approximately 2-50 times to form clonal colonies (v), then editing is induced 7053 by heating the substrate (e.g., for temperature-induced editing) or flowing chemicals under or over the substrate (e.g., sugars, antibiotics for chemical-induced editing) or by moving the solid wall device to a different medium, which is particularly facile if the solid wall device is placed on a fluid permeable membrane which forms the bottom of microwells 7052. After induction of editing 7053, many cells in the colonies of cells that have been edited die as a result of the double-strand cuts caused by active editing, and there is possibly a lag in growth for the edited cells that do survive but must repair and recover following editing (microwells 7058), where cells that do not undergo editing thrive (microwells 7059) (vi). All cells are allowed to grow to continue to establish colonies and normalize, where the colonies of edited cells in microwells 7058 catch up in size and/or cell number with the cells in microwells 7059 that do not undergo editing (vii) due to cell senescence as the unedited cells reach stationary phase. Once the cell colonies are normalized, either pooling of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 7058) are identified and selected (e.g., "cherry picked") resulting in even greater enrichment of edited cells.

In growing the cells, the medium used will depend, of course, on the type of cells being edited—e.g., bacterial, yeast or mammalian. For example, medium for bacterial growth includes LB, SOC, M9 Minimal medium, and Magic medium; medium for yeast cell growth includes TPD, YPG, YPAD, and synthetic minimal medium; and medium for mammalian cell growth includes MEM, DMEM, IMDM, RPMI, and Hanks.

Figure 7B:
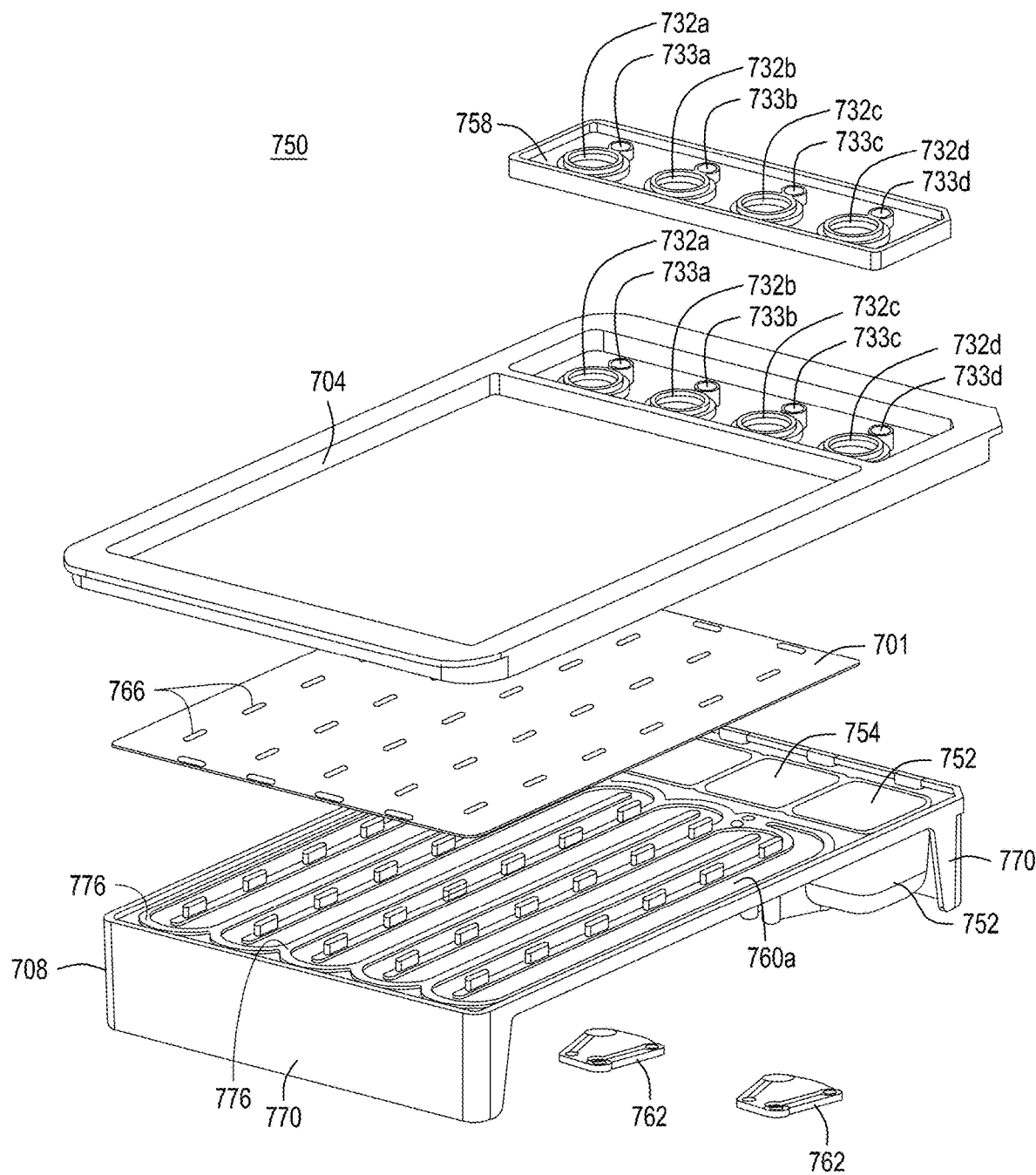
FIGS. 7B-7D depict an embodiment of a solid wall isolation incubation and normalization (SWIIN) module.

A module useful for performing the method depicted in FIG. 7A is a solid wall isolation, incubation, and normalization (SWIIN) module. FIG. 7B depicts an embodiment of a SWIIN module 750 from an exploded top perspective view. In SWIIN module 750 the retentate member is formed on the bottom of a top of a SWIIN module component and the permeate member is formed on the top of the bottom of a SWIIN module component.

The SWIIN module 750 in FIG. 7B comprises from the top down, a reservoir gasket or cover 758, a retentate member 704 (where a retentate flow channel cannot be seen in this FIG. 7B), a perforated member 701 swaged with a filter (filter not seen in FIG. 7B), a permeate member 708 comprising integrated reservoirs (permeate reservoirs 752 and retentate reservoirs 754), and two reservoir seals 762, which seal the bottom of permeate reservoirs 752 and retentate reservoirs 754. A permeate channel 760a can be seen disposed on the top of permeate member 708, defined by a raised portion 776 of serpentine channel 760a, and ultrasonic tabs 764 can be seen disposed on the top of permeate member 708 as well. The perforations that form the wells on perforated member 701 are not seen in this FIG. 7B; however, through-holes 766 to accommodate the ultrasonic tabs 764 are seen. In addition, supports 770 are disposed at either end of SWIIN module 750 to support SWIIN module 750 and to elevate permeate member 708 and retentate member 704 above reservoirs 752 and 754 to minimize bubbles or air entering the fluid path from the permeate reservoir to serpentine channel 760a or the fluid path from the retentate reservoir to serpentine channel 760b (neither fluid path is seen in this FIG. 7B).

In this FIG. 7B, it can be seen that the serpentine channel 760a that is disposed on the top of permeate member 708 traverses permeate member 708 for most of the length of permeate member 708 except for the portion of permeate member 708 that comprises permeate reservoirs 752 and retentate reservoirs 754 and for most of the width of permeate member 708. As used herein with respect to the distribution channels in the retentate member or permeate member, "most of the length" means about 95% of the length of the retentate member or permeate member, or about 90%, 85%, 80%, 75%, or 70% of the length of the retentate member or permeate member. As used herein with respect to the distribution channels in the retentate member or permeate member, "most of the width" means about 95% of the width of the retentate member or permeate member, or about 90%, 85%, 80%, 75%, or 70% of the width of the retentate member or permeate member.

In this embodiment of a SWIIN module, the perforated member includes through-holes to accommodate ultrasonic tabs disposed on the permeate member. Thus, in this embodiment the perforated member is fabricated from 316 stainless steel, and the perforations form the walls of microwells while a filter or membrane is used to form the bottom of the microwells. Typically, the perforations (microwells) are approximately 150 µm-200 µm in diameter, and the perforated member is approximately 125 µm deep, resulting in microwells having a volume of approximately 2.5 nl, with a total of approximately 200,000 microwells. The distance between the microwells is approximately 279 µm center-to-center. Though here the microwells have a volume of approximately 2.5 nl, the volume of the microwells may be from 1 to 25 nl, or preferably from 2 to 10 nl, and even more preferably from 2 to 4 nl. As for the filter or membrane, like the filter described previously, filters appropriate for use are solvent resistant, contamination free during filtration, and are able to retain the types and sizes of cells of interest. For example, in order to retain small cell types such as bacterial cells, pore sizes can be as low as 0.10 µm, however for other cell types (e.g., such as for mammalian cells), the pore sizes can be as high as 10.0 µm-20.0 µm or more. Indeed, the pore sizes useful in the cell concentration device/module include filters with sizes from 0.10 µm, 0.11 µm, 0.12 µm, 0.13 µm, 0.14 µm, 0.15 µm, 0.16 µm, 0.17 µm, 0.18 µm, 0.19 µm, 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber.

The cross-section configuration of the mated serpentine channel may be round, elliptical, oval, square, rectangular, trapezoidal, or irregular. If square, rectangular, or another shape with generally straight sides, the cross section may be from about 2 mm to 15 mm wide, or from 3 mm to 12 mm wide, or from 5 mm to 10 mm wide. If the cross section of the mated serpentine channel is generally round, oval or elliptical, the radius of the channel may be from about 3 mm to 20 mm in hydraulic radius, or from 5 mm to 15 mm in hydraulic radius, or from 8 mm to 12 mm in hydraulic radius.

Serpentine channels 760a and 760b can have approximately the same volume or the serpentine channels 760a and 760b may have different volumes. For example, each "side" or portion 760a, 760b of the serpentine channel may have a volume of, e.g., 2 mL, or serpentine channel 760a of permeate member 708 may have a volume of 2 mL, and the serpentine channel 760b of retentate member 704 may have a volume of, e.g., 3 mL. The volume of fluid in the serpentine channel may range from about 2 mL to about 80 mL, or about 4 mL to 60 mL, or from 5 mL to 40 mL, or from 6 mL to 20 mL (note these volumes apply to a SWIIN module comprising a, e.g., 50-500K perforation member). The volume of the reservoirs may range from 5 mL to 50 mL, or from 7 mL to 40 mL, or from 8 mL to 30 mL or from 10 mL to 20 mL, and the volumes of all reservoirs may be the same or the volumes of the reservoirs may differ (e.g., the volume of the permeate reservoirs is greater than that of the retentate reservoirs).

The serpentine channel portions 760a and 760b of the permeate member 708 and retentate member 704, respectively, are approximately 200 mm long, 130 mm wide, and 4 mm thick, though in other embodiments, the retentate and permeate members can be from 75 mm to 400 mm in length, or from 100 mm to 300 mm in length, or from 150 mm to 250 mm in length; from 50 mm to 250 mm in width, or from 75 mm to 200 mm in width, or from 100 mm to 150 mm in width; and from 2 mm to 15 mm in thickness, or from 4 mm to 10 mm in thickness, or from 5 mm to 8 mm in thickness. Embodiments the retentate (and permeate) members may be fabricated from PMMA (poly(methyl methacrylate) or other materials may be used, including polycarbonate, cyclic olefin co-polymer (COC), glass, polyvinyl chloride, polyethylene, polyamide, polypropylene, polysulfone, polyurethane, and co-polymers of these and other polymers. Preferably at least the retentate member is fabricated from a transparent material so that the cells can be visualized (see, e.g., FIG. 7E and the description thereof). For example, a video camera may be used to monitor cell growth by, e.g., density change measurements based on an image of an empty well, with phase contrast, or if, e.g., a chromogenic marker, such as a chromogenic protein, is used to add a distinguishable color to the cells. Chromogenic markers such as blitzen blue, dreidel teal, virginia violet, vixen purple, prancer purple, tinsel purple, maccabee purple, donner magenta, cupid pink, seraphina pink, scrooge orange, and leor orange (the Chromogenic Protein Paintbox, all available from ATUM (Newark, Calif.)) obviate the need to use fluorescence, although fluorescent cell markers, fluorescent proteins, and chemiluminescent cell markers may also be used.

Because the retentate member preferably is transparent, colony growth in the SWIIN module can be monitored by automated devices such as those sold by JoVE (ScanLag™ system, Cambridge, Mass.) (also see Levin-Reisman, et al., Nature Methods, 7:737-39 (2010)). Cell growth for, e.g., mammalian cells may be monitored by, e.g., the growth monitor sold by IncuCyte (Ann Arbor, Mich.) (see also, Choudhry, PLos One, 11(2):e0148469 (2016)). Further, automated colony pickers may be employed, such as those sold by, e.g., TECAN (Pickolo™ system, Mannedorf, Switzerland); Hudson Inc. (RapidPick™, Springfield, N.J.); Molecular Devices (QPix 400 TMsystem, San Jose, Calif.); and Singer Instruments (PIXL™ system, Somerset, UK).

Due to the heating and cooling of the SWIIN module, condensation may accumulate on the retentate member which may interfere with accurate visualization of the growing cell colonies. Condensation of the SWIIN module 750 may be controlled by, e.g., moving heated air over the top of (e.g., retentate member) of the SWIIN module 750, or by applying a transparent heated lid over at least the serpentine channel portion 760b of the retentate member 704. See, e.g., FIG. 7E and the description thereof infra.

In SWIIN module 750 cells and medium at a dilution appropriate for Poisson or substantial Poisson distribution of the cells in the microwells of the perforated member—are flowed into serpentine channel 760b from ports in retentate member 704, and the cells settle in the microwells while the medium passes through the filter into serpentine channel 760a in permeate member 708. The cells are retained in the microwells of perforated member 701 as the cells cannot travel through filter 703. Appropriate medium may be introduced into permeate member 708 through permeate ports 711. The medium flows upward through filter 703 to nourish the cells in the microwells (perforations) of perforated member 701. Additionally, buffer exchange can be effected by cycling medium through the retentate and permeate members. In operation, the cells are deposited into the microwells, are grown for an initial, e.g., 2-100 doublings, editing is induced by, e.g., raising the temperature of the SWIIN to 42° C. to induce a temperature inducible promoter or by removing growth medium from the permeate member and replacing the growth medium with a medium comprising a chemical component that induces an inducible promoter.

Once editing has taken place, the temperature of the SWIIN may be decreased, or the inducing medium may be removed and replaced with fresh medium lacking the chemical component thereby de-activating the inducible promoter. The cells then continue to grow in the SWIIN module 750 until the growth of the cell colonies in the microwells is normalized. For the normalization protocol, once the colonies are normalized, the colonies are flushed from the microwells by applying fluid or air pressure (or both) to the permeate member serpentine channel 760a and thus to filter 703 and pooled. Alternatively, if cherry picking is desired, the growth of the cell colonies in the microwells is monitored, and slow-growing colonies are directly selected; or, fast-growing colonies are eliminated.

Figure 7C:
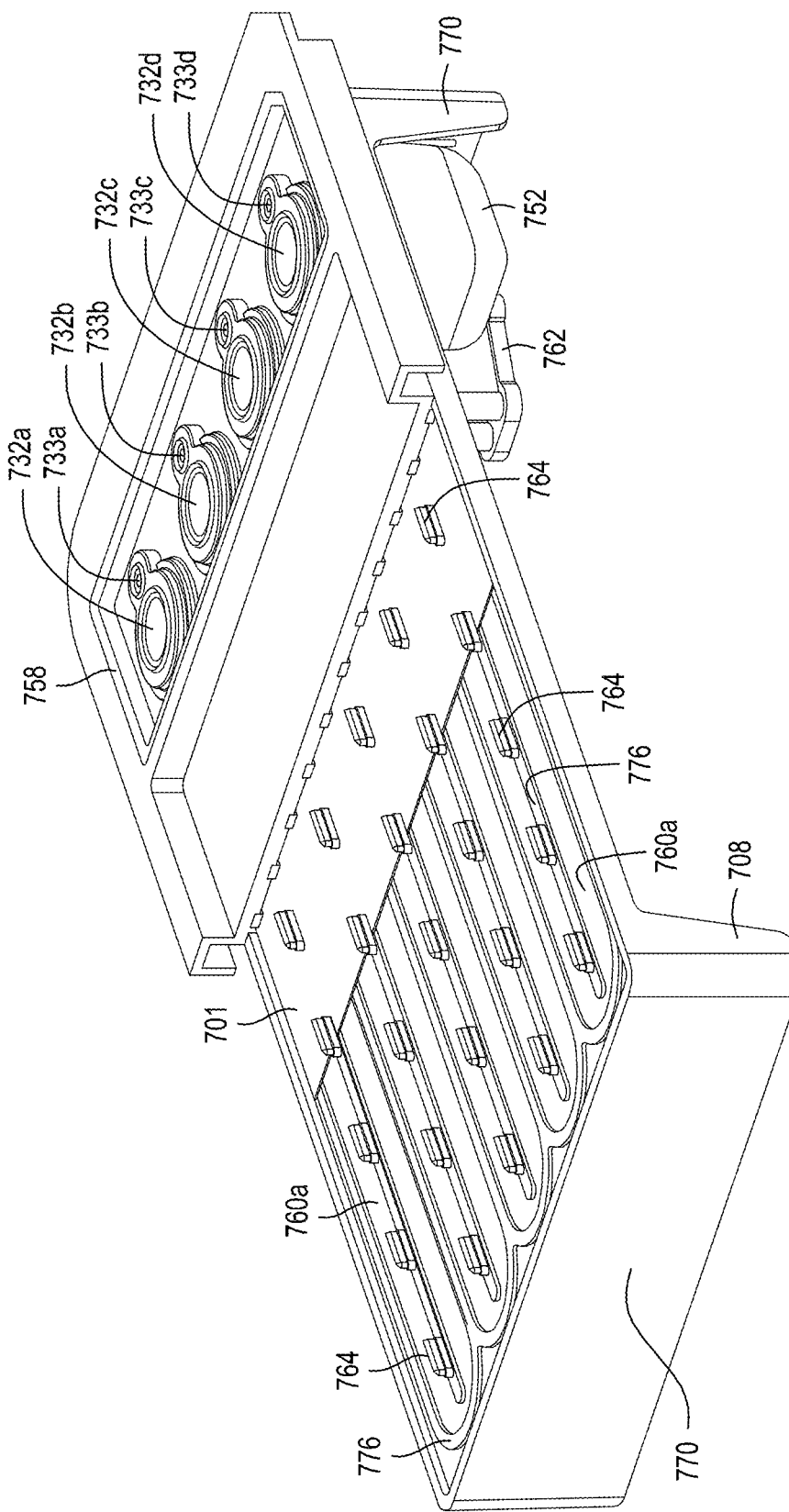

FIG. 7C is a top perspective view of a SWIIN module with the retentate and perforated members in partial cross section. In this FIG. 7C, it can be seen that serpentine channel 760a is disposed on the top of permeate member 708 is defined by raised portions 776 and traverses permeate member 708 for most of the length and width of permeate member 708 except for the portion of permeate member 708 that comprises the permeate and retentate reservoirs (note only one retentate reservoir 752 can be seen). Moving from left to right, reservoir gasket 758 is disposed upon the integrated reservoir cover 778 (cover not seen in this FIG. 7C) of retentate member 704. Gasket 758 comprises reservoir access apertures 732a, 732b, 732c, and 732d, as well as pneumatic ports 733a, 733b, 733c and 733d. Also at the far left end is support 770. Disposed under permeate reservoir 752 can be seen one of two reservoir seals 762. In addition to the retentate member being in cross section, the perforated member 701 and filter 703 (filter 703 is not seen in this FIG. 7C) are in cross section. Note that there are a number of ultrasonic tabs 764 disposed at the right end of SWIIN module 750 and on raised portion 776 which defines the channel turns of serpentine channel 760a, including ultrasonic tabs 764 extending through through-holes 766 of perforated member 701. There is also a support 770 at the end distal reservoirs 752, 754 of permeate member 708.

Figure 7D:
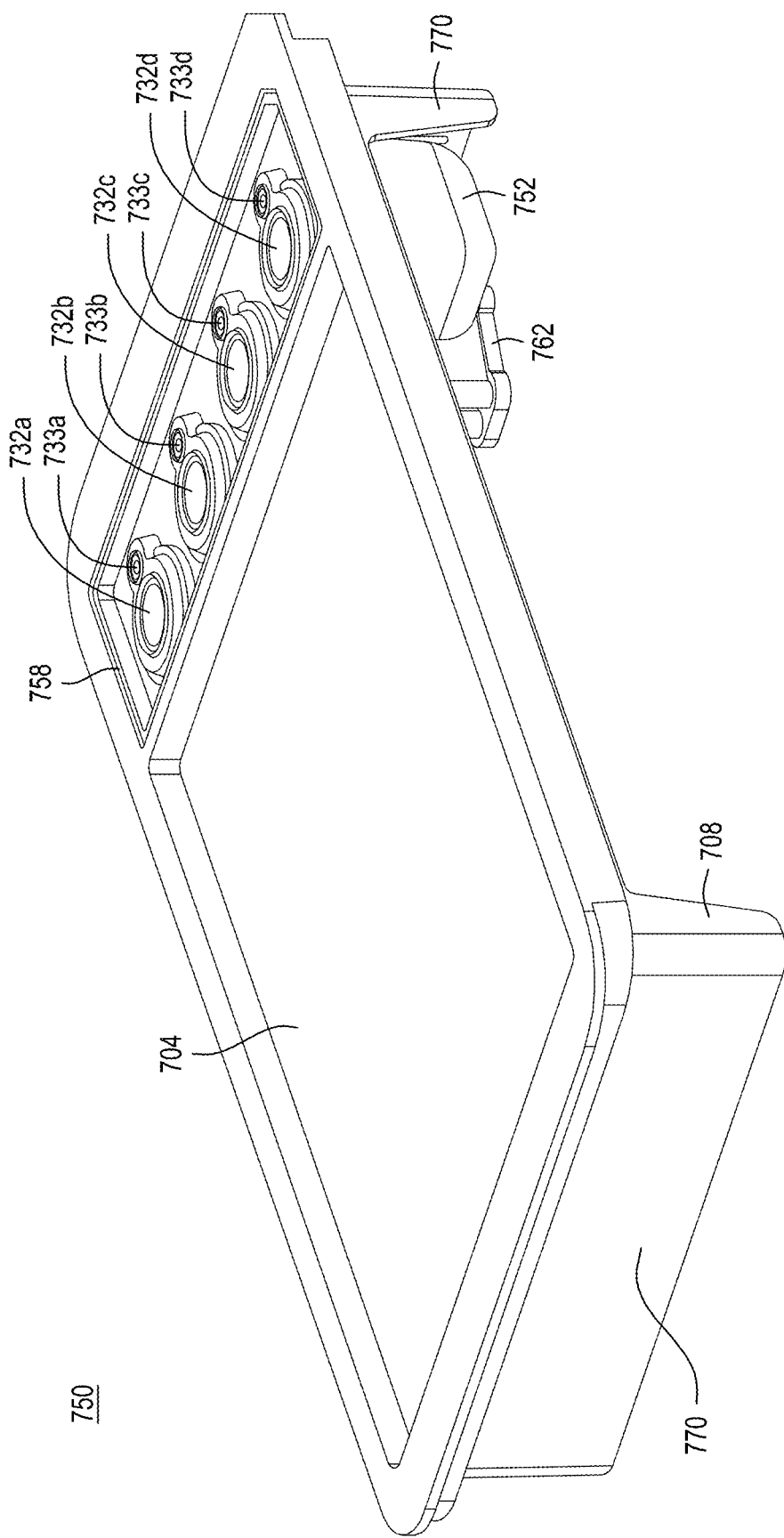

FIG. 7D is a side perspective view of an assembled SWIIN module 750, including, from right to left, reservoir gasket 758 disposed upon integrated reservoir cover 778 (not seen) of retentate member 704. Gasket 758 may be fabricated from rubber, silicone, nitrile rubber, polytetrafluoroethylene, a plastic polymer such as polychlorotrifluoroethylene, or other flexible, compressible material. Gasket 758 comprises reservoir access apertures 732a, 732b, 732c, and 732d, as well as pneumatic ports 733a, 733b, 733c and 733d. Also at the far-left end is support 770 of permeate member 708. In addition, permeate reservoir 752 can be seen, as well as one reservoir seal 762. At the far-right end is a second support 770.

Imaging of cell colonies growing in the wells of the SWIIN is desired in most implementations for, e.g., monitoring both cell growth and device performance and imaging is necessary for cherry-picking implementations. Real-time monitoring of cell growth in the SWIIN requires backlighting, retentate plate (top plate) condensation management and a system-level approach to temperature control, air flow, and thermal management. In some implementations, imaging employs a camera or CCD device with sufficient resolution to be able to image individual wells. For example, in some configurations a camera with a 9-pixel pitch is used (that is, there are 9 pixels center-to-center for each well). Processing the images may, in some implementations, utilize reading the images in grayscale, rating each pixel from low to high, where wells with no cells will be brightest (due to full or nearly-full light transmission from the backlight) and wells with cells will be dim (due to cells blocking light transmission from the backlight). After processing the images, thresholding is performed to determine which pixels will be called "bright" or "dim", spot finding is performed to find bright pixels and arrange them into blocks, and then the spots are arranged on a hexagonal grid of pixels that correspond to the spots. Once arranged, the measure of intensity of each well is extracted, by, e.g., looking at one or more pixels in the middle of the spot, looking at several to many pixels at random or pre-set positions, or averaging X number of pixels in the spot. In addition, background intensity may be subtracted. Thresholding is again used to call each well positive (e.g., containing cells) or negative (e.g., no cells in the well). The imaging information may be used in several ways, including taking images at time points for monitoring cell growth. Monitoring cell growth can be used to, e.g., remove the "muffin tops" of fast-growing cells followed by removal of all cells or removal of cells in "rounds" as described above, or recover cells from specific wells (e.g., slow-growing cell colonies); alternatively, wells containing fast-growing cells can be identified and areas of UV light covering the fast-growing cell colonies can be projected (or rastered with shutters) onto the SWIIN to irradiate or inhibit growth of those cells. Imaging may also be used to assure proper fluid flow in the serpentine channel 760.

Figure 7E:
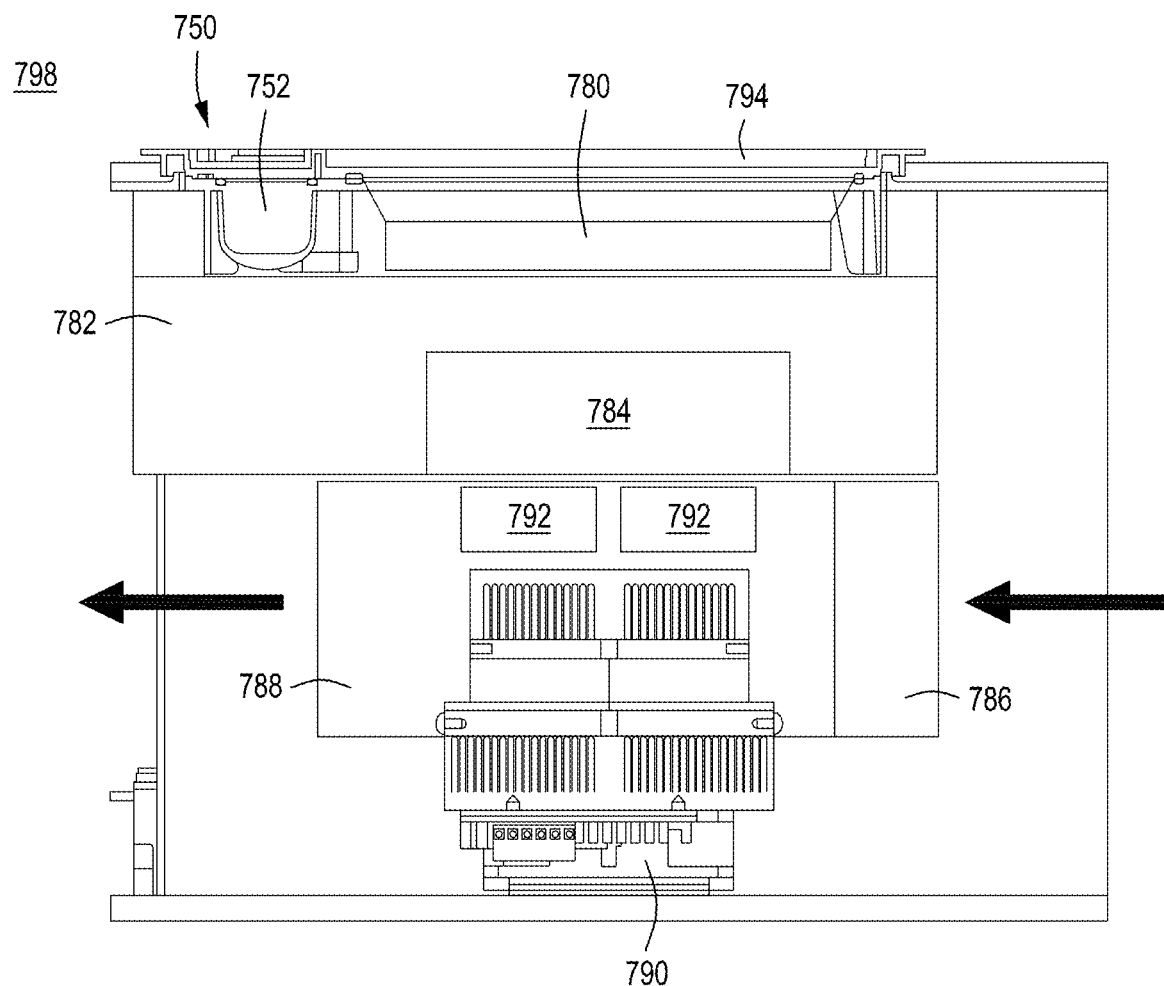
FIG. 7E depicts the embodiment of the SWIIN module in FIGS. 7B-7D further comprising a heater and a heated cover.

FIG. 7E depicts the embodiment of the SWIIN module in FIGS. 7B-7D further comprising a heat management system including a heater and a heated cover. The heater cover facilitates the condensation management that is required for imaging. Assembly 798 comprises a SWIIN module 750 seen lengthwise in cross section, where one permeate reservoir 752 is seen. Disposed immediately upon SWIIN module 750 is cover 794 and disposed immediately below SWIIN module 750 is backlight 780, which allows for imaging. Beneath and adjacent to the backlight and SWIIN module is insulation 782, which is disposed over a heatsink 784. In this FIG. 7E, the fins of the heatsink would be in-out of the page. In addition there is also axial fan 786 and heat sink 788, as well as two thermoelectric coolers 792, and a controller 790 to control the pneumatics, thermoelectric coolers, fan, solenoid valves, etc. The arrows denote cool air coming into the unit and hot air being removed from the unit. It should be noted that control of heating allows for growth of many different types of cells (prokaryotic and eukaryotic) as well as strains of cells that are, e.g., temperature sensitive, etc., and allows use of temperature-sensitive promoters. Temperature control allows for protocols to be adjusted to account for differences in transformation efficiency, cell growth and viability. For more details regarding solid wall isolation incubation and normalization devices see U.S. Ser. No. 16/399,988, filed 30 Apr. 2019; Ser. No. 16/454,865, filed 26 Jun. 2019; Ser. No. 16/540,606, filed 14 Aug. 2019; Ser. No. 16/597,826, filed 9 Oct. 2019; and Ser. No. 16/597, 831, filed 9 Oct. 2019. For alternative isolation, incubation and normalization modules, see U.S. Ser. No. 16/536,049, filed 8 Aug. 2019.

Use of the Cell Growth Device

Figure 8:
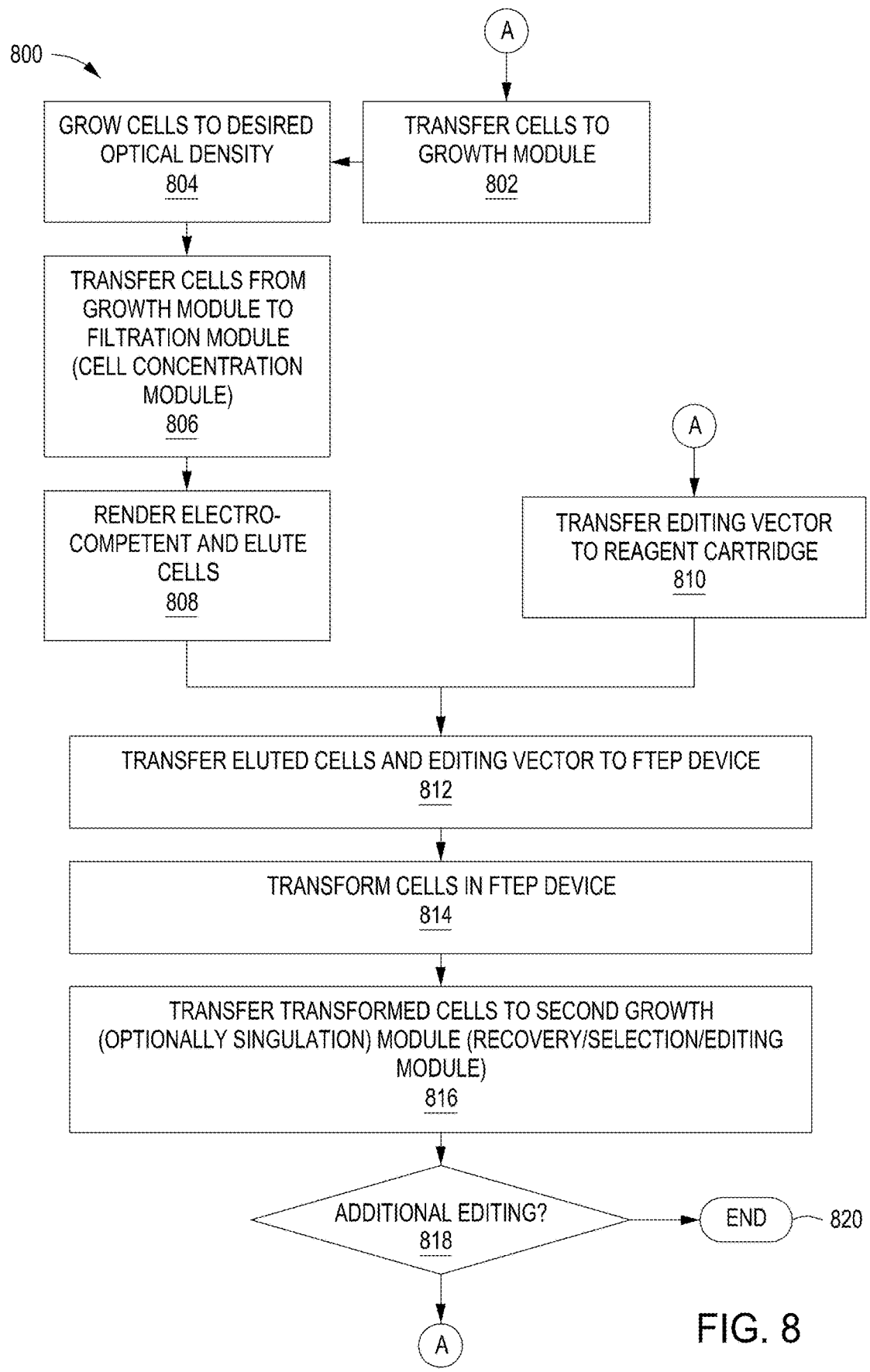
FIG. 8 is a flow chart of an exemplary method for automated multi-module cell editing to produce the cell libraries as described herein.

FIG. 8 is a flow chart of an example method 800 for using an automated multi-module cell editing instrument such as the systems illustrated in FIGS. 4A-4C which include the FTEP devices described in relation to FIGS. 1A-1P. A processing system, for example, directs the processing stage of the method 800. For example, a software script may identify settings for each processing stage and instructions for movement of a robotic handling system to perform the actions of the method 800. In some embodiments, a software instruction script may be identified by a reagent cartridge supplied to the automated multi-module cell editing instrument. For example, the reagent cartridge may include machine-readable indicia, such as a bar code or QR code, including identification of a script stored in a memory of the automated multi-module cell editing instrument. In another example, the reagent cartridge may contain a downloadable script embedded in machine-readable indicia such as a radio frequency (RF) tag. In other embodiments, the user may identify a script, for example through downloading the script via a wired or wireless connection to the processing system of the automated multi-module cell editing instrument or through selecting a stored script through a user interface of the automated multi-module cell editing instrument. In a particular example, the automated multi-module cell editing instrument may include a touch screen interface for submitting user settings and activating cell processing. Again, the automated multi-module cell processing instrument is a stand-alone instrument, and between the script, reagent reservoirs, and liquid handling system facilitates live cell editing in an entirely automated manner without human intervention.

In some implementations, the method 800 begins with transferring cells to a cell growth module (802). The growth module may be any growth module amendable to automation such as, for example, the cell growth module 550 described in relation to FIGS. 5B-5D. In a particular example, the processing system may direct the robotic handling system to transfer cells to the growth module. In another example, the cells may be transferred from a reagent cartridge to the growth module by the robotic handling system. In some embodiments, the growth vial may contain growth media and be supplied, e.g., as part of a kit. In other embodiments, the growth vial may be filled with medium transferred, e.g., via the liquid handling device, from a reagent container.

In some embodiments, prior to transferring the cells (e.g., from the reagent cartridge or from a vial added to the instrument), machine-readable indicia may be scanned upon the vial or other container situated in a position designated for cells to confirm that the vial or container is marked as containing cells. Further, the machine-readable indicia may indicate a type of cells provided to the instrument. The type of cells, in some embodiments, may cause the instrument to select a particular processing script (e.g., series of instructions for the robotic handling system and settings and activation of the various modules).

In some implementations, the cells are grown in the growth module to a desired optical density (804). For example, the processing system may manage a temperature setting of the growth module for incubating the cells during the growth cycle. The processing system may further receive sensor signals from the growth module indicative of optical density and analyze the sensor signals to monitor growth of the cells. In some embodiments, a user may set growth parameters for managing growth of the cells. For example, temperature, and the degree of agitation of the cells. Further, in some embodiments, the user may be updated regarding the growth process. The updates, in some examples, may include a message presented on a user interface of the automated multi-module cell editing instrument, a text message to a user's cell phone number, an email message to an email account, or a message transmitted to an app executing upon a portable electronic device (e.g., cell phone, tablet, etc.). Responsive to the messages, in some embodiments, the user may modify parameters, such as temperature, to adjust cell growth. For example, the user may submit updated parameters through a user interface of the automated multi-module cell editing instrument or through a portable computing device application in communication with the automated multi-module cell editing instrument, such as a user interface (see, e.g., touch screen display 401 of FIG. 4C).

Although described in relation to optical density, in other implementations cell growth within the growth module may be monitored using a different measure of cell density and physiological state such as, in some examples, pH, dissolved oxygen, released enzymes, acoustic properties, and electrical properties.

In some implementations, upon reaching the desired optical density (804), the cells are transferred from the growth module to a filtration module or cell wash and concentration module (806). The robotic handling system, for example, may transfer the cells from the growth module to the cell concentration module. The cell concentration module, for example, may be (and typically is) designed to render the cells electrocompetent. See FIGS. 6A-6D in relation to the TFF device, above. The cells are rendered electrocompetent and eluted in the filtration module or cell wash and concentration module (808). The cells may be eluted using a wash solution. For example, the cells may be eluted using reagents from a reagent supply.

Once the cells have been rendered electrocompetent and suspended in an appropriate volume such as 50 µL to 10 mL, or 100 µL to 9 mL, or 150 µL to 8 mL, or 250 µL to 7 mL, or 500 µL to 6 mL, or 750 µL to 5 mL for transformation (808), the cells are transferred to, e.g., an FTEP module (812). The robotic handling system, for example, may transfer the cells from the cell concentration device or module to the FTEP 812. The filtration module may be physically coupled to the FTEP device, or these modules may be separate.

In some implementations, nucleic acids are prepared outside of the automated multi-module cell editing instrument. For example, an assembled vector or other nucleic acid assembly may be included as a reagent in, e.g., a reagent cartridge 810 by a user prior to running the transformation process and other processes in the method 800. If provided in a reagent cartridge, the nucleic acid assembly (e.g., editing vector library) is transferred to the FTEP device as well.

The cells are transformed in the FTEP module with the editing vector provided in the reagent cartridge (814). A buffer or medium may be transferred to the transformation module and added to the cells so that the cells may be suspended in a buffer or medium that is favorable for cell survival during electroporation. Prior to transferring the buffer or medium, machine-readable indicia may be scanned upon the vial or other container or reservoir situated in the position designated for the buffer or medium to confirm the contents of the vial, container, or reservoir. Further, the machine-readable indicia may indicate a type of buffer or medium provided to the instrument. The type of buffer or medium, in some embodiments, may cause the instrument to select a particular processing script (e.g., settings and activation of the transformation module appropriate for the particular buffer or medium). For bacterial cell electroporation, low conductance mediums, such as water or glycerol solutions, may be used to reduce the heat production by transient high current. For yeast cells, a sorbitol solution may be used. For mammalian cell electroporation, cells may be suspended in a highly conductive medium or buffer, such as MEM, DMEM, IMDM, RPMI, Hanks', PBS, HBSS, HeBS and Ringer's solution. In a particular example, the robotic handling system may transfer a buffer solution to FTEP module from the reagent cartridge. As described in relation to FIGS. 1A-1P and 3A-3F, the FTEP device may be a disposable FTEP device and/or the FTEP device may be provided as part of the reagent cartridge. Alternatively, the FTEP device may a separate module.

Once transformed, the cells are transferred to, e.g., a second growth/recovery/editing module (816) such as the cell growth module described in relation to FIGS. 5A-5D. The robotic handling system, for example, may transfer the transformed cells to the second growth module through a sipper or pipettor interface. In another example, the robotic handling system may transfer a vial containing the transformed cells from a chamber of the transformation module to a chamber of the second growth module.

The second growth module, in some embodiments, acts as a recovery module, allowing the cells to recover from the transformation process. In other embodiments, the cells may be provided to a separate recovery module prior to being transported to the second growth module. During recovery, the second growth module allows the transformed cells to uptake and, in certain aspects, integrate the introduced nucleic acids into the genome of the cell. The second growth module may be configured to incubate the cells at any user-defined temperature optimal for cell growth, preferably 25°, 30°, or 37° C.

In some embodiments, the second growth module behaves as a selection module, selecting the transformed cells based on an antibiotic or other reagent. In one example, the RNA-guided nuclease (RGN) protein system is used for selection to cleave the genomes of cells that have not received the desired edit. In the example of an antibiotic selection agent, the antibiotic may be added to the second growth module to enact selection. Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, or chloramphenicol-resistance gene. The robotic handling system, for example, may transfer the antibiotic to the second growth module through a sipper or pipettor interface. In some embodiments, removing dead cell background is aided by using lytic enhancers such as detergents, osmotic stress by hyponic wash, temperature, enzymes, proteases, bacteriophage, reducing agents, or chaotropes. The processing system, for example, may alter environmental variables, such as temperature, to induce selection, while the robotic handling system may deliver additional materials (e.g., detergents, enzymes, reducing agents, etc.) to aid in selection. In other embodiments, cell removal and/or media exchange by filtration is used to reduce dead cell background.

In further embodiments, in addition to or as an alternative to applying selection, the second growth module serves as an editing module, allowing for genome editing in the transformed cells. Alternatively, in other embodiments, the cells post-recovery and post-selection (if performed) are transferred to a separate editing module. As an editing module, the second growth module induces editing of the cells' genomes, e.g., through facilitating expression of the introduced nucleic acids. Expression of the nuclease and/or editing cassette nucleic acids may involve one or more of chemical, light, viral, or temperature induction methods. The second growth module, for example, may be configured to heat or cool the cells during a temperature induction process. In a particular illustration, the cells may be induced by heating at 42° C.–50° C. Further to the illustration, the cells may then be cooled to 0-10° C. after induction. In the example of chemical or viral induction, an inducing agent may be transferred to the second growth module to induce editing. If an inducible nuclease and/or editing cassette was introduced to the cells during editing, it can be induced through introduction of an inducer molecule. The inducing agent or inducer molecule, in some implementations, is transferred to the second growth module by the robotic handling system, e.g., through a pipettor or sipper interface.

In some implementations, if no additional cell editing is desired (818), the cells may be transferred from the cell growth module to a storage unit for later removal from the automated multi-module cell editing instrument (820). The robotic handling system, for example, may transfer the cells to a storage unit through a sipper or pipettor interface. In another example, the robotic handling system may transfer a vial containing the cells from a chamber of the second growth module to a vial or tube within the storage unit.

In some implementations, if additional cell editing is desired (818), the cells may be transferred to a growth module (802), grown to a desired OD (804), transferred to a cell concentration module (806), then concentrated and rendered electrocompetent (808). Further, in some embodiments, a new assembled nucleic acid sample may be prepared by the nucleic acid assembly module at this time, or, alternatively, a second fully assembled nucleic acid may be directly introduced to the cells from, e.g., the reagent cartridge. Prior to recursive editing, in some embodiments, the automated multi-module cell editing instrument may require additional materials be supplied by the user, e.g., through the introduction of one or more separate reagents vials or cartridge.

The steps may be the same or different during the second round of editing. For example, in some embodiments, upon a subsequent execution of step 804, a selective growth medium is transferred to the growth module to enable selection of edited cells from the first round of editing. The robotic handling system may transfer the selective growth medium from a vial or container in a reagent cartridge situated in a position designated for selective growth medium. Prior to transferring the selective growth medium, machine-readable indicia may be scanned upon the vial or other container or reservoir situated in the position designated for the selective growth medium to confirm the contents of the vial, container, or reservoir. Further, the machine-readable indicia may indicate a type of selective growth medium provided to the instrument. The type of selective growth medium, in some embodiments, may cause the instrument to select a particular processing script (e.g., settings and activation of the growth module appropriate for the particular selective growth medium). Particular examples of recursive editing workflows are described in relation to FIG. 10.

In some implementations, the method 800 can be timed to introduce materials and/or complete the editing cycle or growth cycle in coordination with a user's schedule. For example, the automated multi-module cell editing instrument may provide the user the ability to schedule completion of one or more cell processing cycles (e.g., one or more recursive edits) such that the method 800 is enacted with a goal of completion at the user's preferred time. The time scheduling, for example, may be set through a user interface. For illustration only, a user may set completion of a first cycle to 4:00 PM so that the user can supply additional cartridges of materials to the automated multi-module cell editing instrument to enable overnight processing of another round of cell editing. Thus, a user may time the programs so that two or more cycles may be programmed in a specific time period, e.g., a 24-hour period.

In some implementations, throughout the method 800, the automated multi-module cell editing instrument may alert the user to its current status. For example, the user interface may present a graphical indication of the present stage of processing. In a particular example, a front face of the automated multi-module call processing instrument may be overlaid with a user interface (e.g., touch screen) that presents an animated graphic depicting present status of the cell processing. The user interface may further present any user and/or default settings associated with the current processing stage (e.g., temperature setting, time setting, etc.). In certain implementations, the status may be communicated to a user via a wireless communications controller.

Although illustrated as a particular series of operations, in other embodiments, more or fewer steps may be included in the method 800. For example, in some embodiments, prior to engaging in each round of editing, the contents of reservoirs, reagent cartridges, and/or vials may be screened to confirm appropriate materials are available to proceed with processing. For example, in some embodiments, one or more imaging sensors (e.g., barcode scanners, cameras, etc.) may confirm contents at various locations within the housing of the automated multi-module cell editing instrument. In one example, multiple imaging sensors may be disposed within the housing of the automated multi-module cell editing instrument, each imaging sensor configured to detect one or more materials (e.g., machine-readable indicia such as barcodes or QR codes, shapes/sizes of materials, etc.). In another example, at least one imaging sensor may be moved by the robotic handling system to multiple locations to detect one or more materials. In further embodiments, one or more weight sensors may detect presence or absence of disposable or replaceable materials. In an illustrative example, the transfer tip supply holder may include a weight sensor to detect whether or not tips have been loaded into the region. In another illustrative example, an optical sensor may detect that a level of liquid waste has reached a threshold level, requiring disposal prior to continuation of cell processing or addition of liquid if the minimum level has not been reached to proceed. Requests for additional materials, removal of waste supplies, or other user interventions (e.g., manual cleaning of one or more elements, etc.), in some implementations, are presented on a graphical user interface of the automated multi-module cell editing instrument. The automated multi-module cell editing instrument, in some implementations, contacts the user with requests for new materials or other manual interventions, for example, through a software app, email, or text message.

Figure 9:
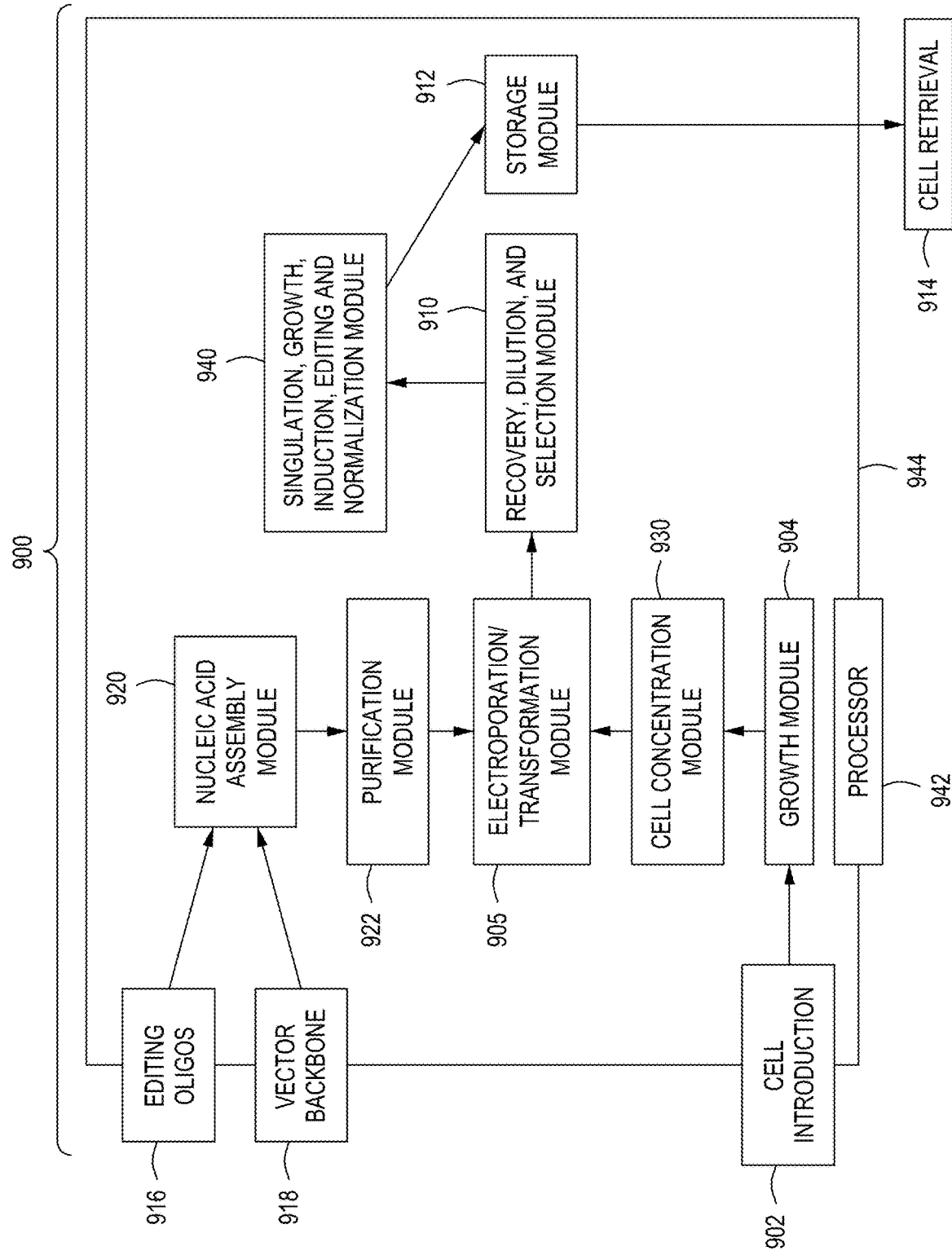
FIG. 9 is a simplified block diagram of an embodiment of an exemplary automated multi-module cell processing instrument comprising a solid wall singulation/growth/editing/normalization module.
Figure 10:
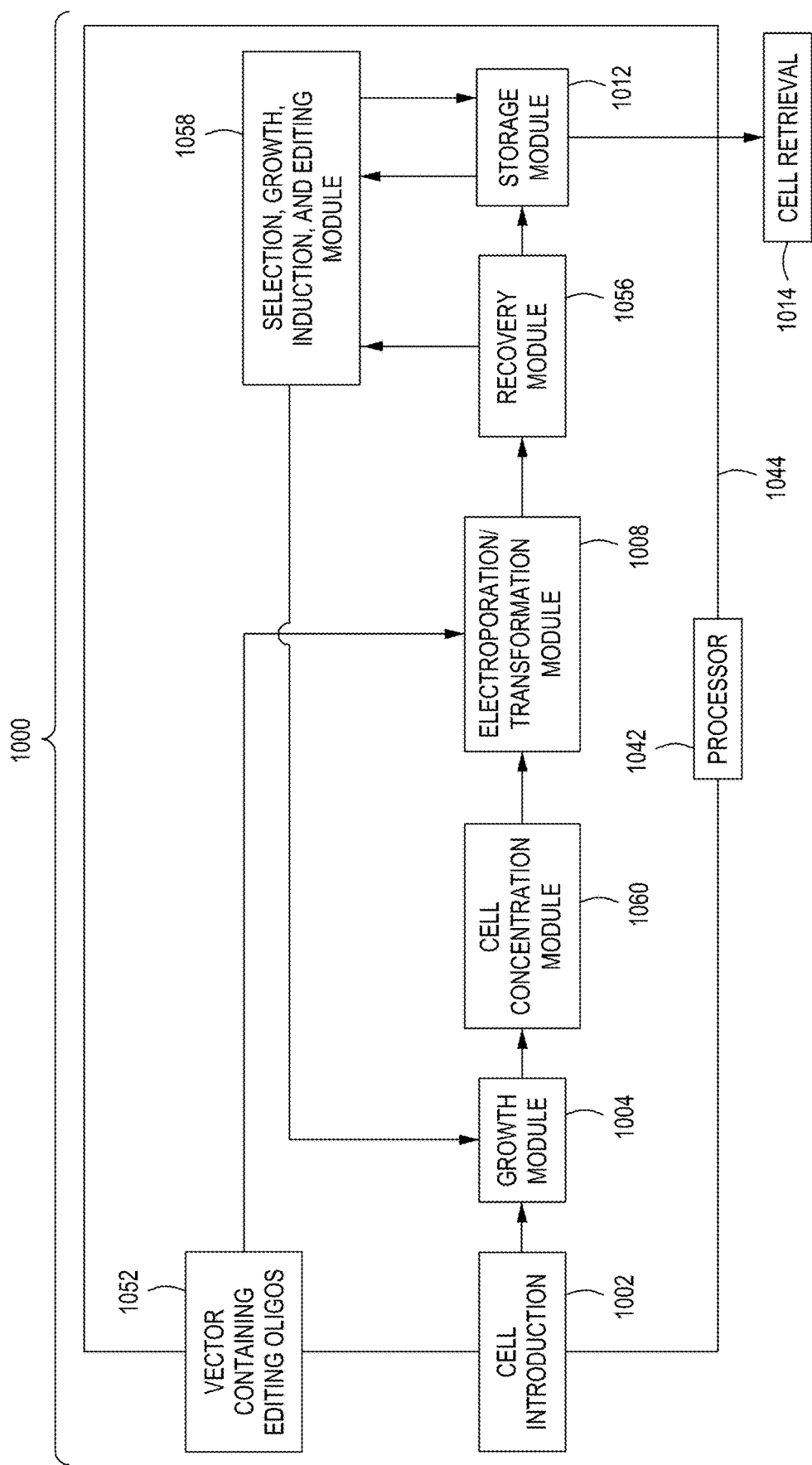

FIG. 9 is a simplified block diagram of an embodiment of an exemplary automated multi-module cell processing instrument 900 comprising a singulation/growth/editing/normalization module 940 for enrichment for edited cells. The cell processing instrument 900 may include a housing 944, a reservoir of cells to be transformed or transfected 902, and a growth module (a cell growth device) 904. The cells to be transformed are transferred from a reservoir 902 to the growth module 904 to be cultured until the cells hit a target OD. Once the cells hit the target OD, the growth module 904 may cool or freeze the cells for later processing, or the cells may be transferred to a cell concentration module 930 where the cells are rendered electrocompetent and concentrated to a volume optimal for cell transformation. Once concentrated, the cells are then transferred to the flow-through electroporation module 905 (e.g., transformation/transfection module).

In addition to the reservoir 902 for storing the cells, the automated multi-module cell processing instrument 900 may include a reservoir for storing editing oligonucleotide cassettes 916 and a reservoir for storing an expression vector backbone 918. Both the editing oligonucleotide cassettes and the expression vector backbone are transferred from the reagent cartridge to a nucleic acid assembly module 920, where the editing oligonucleotide cassettes are inserted into the expression vector backbone. The assembled nucleic acids may be transferred into an optional purification module 922 for desalting and/or other purification and/or concentration procedures needed to prepare the assembled nucleic acids for transformation. Alternatively, pre-assembled nucleic acids, e.g., an editing vector, may be stored within reservoir 916 or 918. Once the processes carried out by the purification module 922 are complete, the assembled nucleic acids are transferred to, e.g., an electroporation device 905, which already contains the cell culture grown to a target OD and rendered electrocompetent via cell concentration module 1130. In electroporation device 905, the assembled nucleic acids are introduced into the cells. Following electroporation, the cells are transferred into a combined recovery/dilution/selection module 910.

Following recovery, and, optionally, selection, the cells are transferred to a singulation, selection, growth, induction, editing, and normalization module 940, where the cells are diluted and compartmentalized such that there is an average of one cell per compartment. Once singulated, the cells grown in, e.g., selective medium, for a pre-determined number of doublings. Once these initial colonies are established, editing is induced and the edited cells are allowed to establish colonies, which are grown to terminal size (e.g., the colonies are normalized). In some embodiments, editing is induced by one or more of the editing components being under the control of an inducible promoter. In some embodiments, the inducible promoter is activated by a rise in temperature and "deactivated" by lowering the temperature. Alternatively, in embodiments where the singulation device is a solid wall device comprising a filter forming the bottom of the microwell, the solid wall device can be transferred to a plate (e.g., agar plate or even to liquid medium) comprising a medium with a component that activates induced editing, then transferred to a medium that deactivates editing. Once the colonies are grown to terminal size, the colonies are pooled. Again, singulation overcomes growth bias from unedited cells and growth bias resulting from fitness effects of different edits.

The recovery, dilution, selection, singulation, induction, editing and growth modules may all be separate, may be arranged and combined as shown in FIG. 9, or may be arranged or combined in other configurations. In certain embodiments, all of recovery, selection, singulation, growth, editing, and normalization are performed in a solid wall device. Alternatively, recovery, selection, and dilution, if necessary, are performed in liquid medium in a separate vessel (module), then transferred to the solid wall singulation/growth/induction/editing/normalization module.

Once the normalized cell colonies are pooled, the cells may be stored, e.g., in a storage module 912, where the cells can be kept at, e.g., 4° C. until the cells are retrieved 914 for further study. Alternatively, the cells may be used in another round of editing. The multi-module cell processing instrument 900 is controlled by a processor 942 configured to operate the instrument 900 based on user input, as directed by one or more scripts, or as a combination of user input or a script. The processor 942 may control the timing, duration, temperature, and operations of the various modules of the instrument 900 and the dispensing of reagents. For example, the processor 942 may cool the cells post-transformation until editing is desired, upon which time the temperature may be raised to a temperature conducive of genome editing and cell growth. The processor may be programmed with standard protocol parameters from which a user may select, a user may specify one or more parameters manually, or one or more scripts associated with the reagent cartridge may specify one or more operations and/or reaction parameters. In addition, the processor 942 may notify the user (e.g., via an application to a smart phone or other device) that the cells have reached the target OD as well as update the user as to the progress of the cells in the various modules in the multi-module cell processing instrument 900.

The automated multi-module cell processing instrument 900 is a nuclease-directed genome editing system and can be used in single editing systems (e.g., introducing one or more edits to a cellular genome in a single editing process). The system of FIG. 10, described below, is configured to perform sequential editing, e.g., using different nuclease-directed systems sequentially to provide two or more genome edits in a cell; and/or recursive editing, e.g. utilizing a single nuclease-directed system to introduce sequentially two or more genome edits in a cell.

Figure 10:
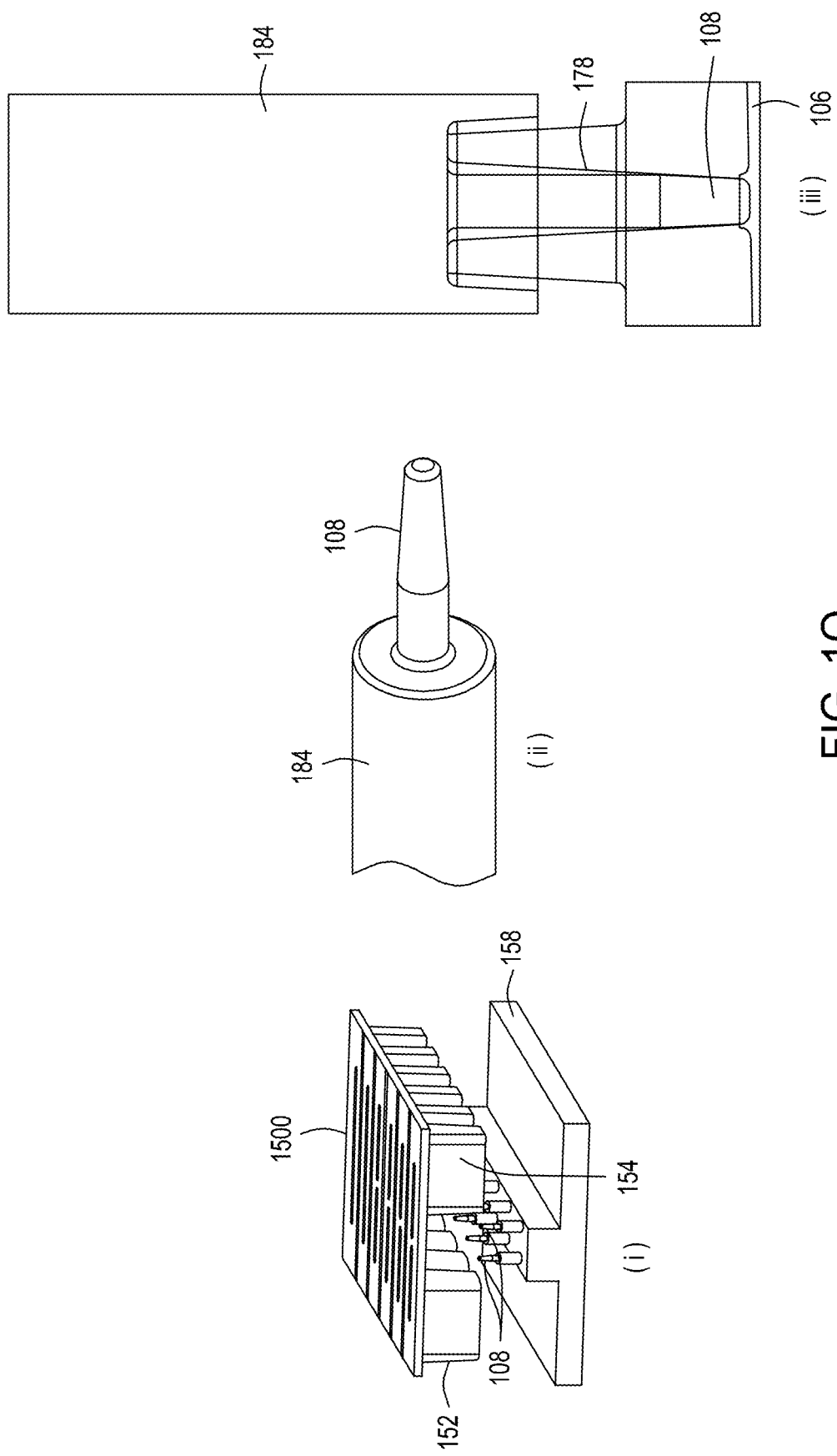
FIG. 10 is a simplified block diagram of an alternative embodiment of an exemplary automated multi-module cell processing instrument comprising a solid wall singulation/growth/editing/normalization module, in this case, used for recursive editing.

FIG. 10 illustrates another embodiment of a multi-module cell processing instrument 1000. This embodiment depicts an exemplary system that performs recursive gene editing on a cell population. As with the embodiment shown in FIG. 9, the cell processing instrument 1000 may include a housing 1044, a reservoir for storing cells to be transformed or transfected 1002, and a cell growth module (comprising, e.g., a rotating growth vial) 1004. The cells to be transformed are transferred from a reservoir to the cell growth module 1004 to be cultured until the cells hit a target OD. Once the cells hit the target OD, the growth module may cool or freeze the cells for later processing or transfer the cells to a cell concentration module 1060 where the cells are subjected to buffer exchange and rendered electrocompetent, and the volume of the cells may be reduced substantially. Once the cells have been concentrated to an appropriate volume, the cells are transferred to electroporation device or module 1008. In addition to the reservoir for storing cells, the multi-module cell processing instrument 1000 includes a reservoir for storing the vector pre-assembled with editing oligonucleotide cassettes 1052. The pre-assembled nucleic acid vectors are transferred to the electroporation device 1008, which already contains the cell culture grown to a target OD. In the electroporation device 1008, the nucleic acids are electroporated into the cells. Following electroporation, the cells are transferred into an optional recovery (and optionally, dilution) module 1056, where the cells are allowed to recover briefly post-transformation.

After recovery, the cells may be transferred to a storage module 1012, where the cells can be stored at, e.g., 4° C. for later processing, or the cells may be diluted and transferred to a selection/growth/induction/editing module/device 1058. The cells are allowed to grow and editing is then induced by providing conditions (e.g., temperature, addition of an inducing or repressing chemical) to induce editing. Note that the selection/growth/induction and editing modules may be the same module or device, where all processes are performed in, e.g., a solid wall singulation device, or selection and/or dilution may take place in a separate vessel before the cells are transferred to an induction/editing module. As an alternative to singulation in, e.g., a solid wall device, the transformed cells may be grown in—and editing can be induced in-bulk liquid (see, e.g., U.S. Ser. No. 16/545,097, filed 20 Aug. 2019. Once the putatively-edited cells are pooled, they may be subjected to another round of editing, beginning with growth, cell concentration and treatment to render electrocompetent, and transformation by yet another donor nucleic acid in another editing cassette via the electroporation device/module 1008.

In electroporation device 1008, the cells selected from the first round of editing are transformed by a second set of editing oligos (or other type of oligos) and the cycle is repeated until the cells have been transformed and edited by a desired number of, e.g., editing cassettes. The multi-module cell processing instrument 1000 exemplified in FIG. 10 is controlled by a processor 1042 configured to operate the instrument based on user input or is controlled by one or more scripts including at least one script associated with the reagent cartridge. The processor 1042 may control the timing, duration, and temperature of various processes, the dispensing of reagents, and other operations of the various modules of the instrument 1000. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing instrument.

It should be apparent to one of ordinary skill in the art given the present disclosure that the process described may be recursive and multiplexed; that is, cells may go through the workflow described in relation to FIG. 10, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries. In any recursive process, it is advantageous to "cure" the previous engine and editing vectors (or single engine+editing vector in a single vector system). "Curing" is a process in which one or more vectors used in the prior round of editing is eliminated from the transformed cells. Curing can be accomplished by, e.g., cleaving the vector(s) using a curing plasmid thereby rendering the editing and/or engine vector (or single, combined vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine+editing vector). The conditions for curing will depend on the mechanism used for curing; that is, in this example, how the curing plasmid cleaves the editing and/or engine plasmid.

Figure 11:
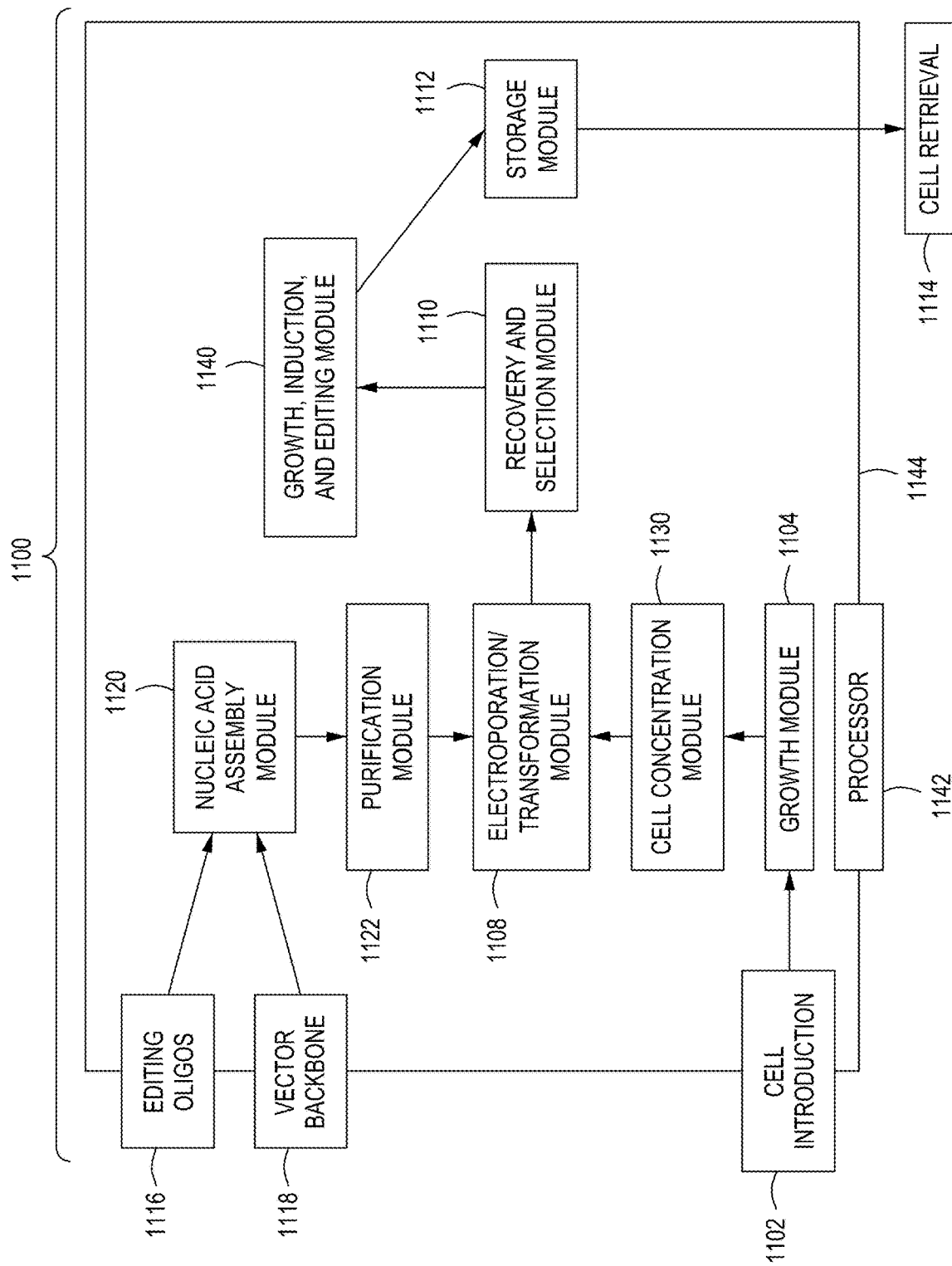
FIG. 11 is a simplified process diagram of yet another embodiment of an exemplary automated multi-module cell processing instrument, in this case without a singulation module.

FIG. 11 is a simplified block diagram of an embodiment of an exemplary automated multi-module cell processing instrument 1100 comprising, e.g., a bulk liquid growth module for induced editing and enrichment for edited cells. (See, e.g., U.S. Ser. No. 16/545,097, filed 20 Aug. 2019.) The cell processing instrument 1100 may include a housing 1144, a reservoir of cells to be transformed or transfected 1102, and a growth module (a cell growth device) 1104. The cells to be transformed are transferred from a reservoir 1102 to the growth module 1104 to be cultured until the cells hit a target OD. Once the cells hit the target OD, the growth module may cool or freeze the cells for later processing, or the cells may be transferred to a cell concentration module 1130 where the cells are rendered electrocompetent and concentrated to a volume optimal for cell transformation. Once concentrated, the cells are then transferred to an electroporation module 1108 (e.g., transformation/transfection module).

In addition to the reservoir 1102 for storing the cells, the instrument 1100 may include a reservoir for storing editing cassettes 1116 and a reservoir for storing an expression vector backbone 1118. Both the editing oligonucleotide cassettes and the expression vector backbone are transferred from the reagent cartridge to a nucleic acid assembly module 1120, where the editing oligonucleotide cassettes are inserted into the expression vector backbone. The assembled nucleic acids may be transferred into an optional purification module 1122 for desalting and/or other purification and/or concentration procedures needed to prepare the assembled nucleic acids for transformation. Alternatively, pre-assembled nucleic acids, e.g., an editing vector, may be stored within reservoir 1116 or 1118. Once the processes carried out by the purification module 1122 are complete, the assembled nucleic acids are transferred to, e.g., an electroporation device or module 1108, which already contains the cell culture grown to a target OD and rendered electrocompetent via cell concentration module 1130. In electroporation device 1108, the assembled nucleic acids are introduced into the cells. Following electroporation, the cells are transferred into a combined recovery/selection module 1110.

Following recovery, and, optionally, selection, the cells are transferred to a growth, induction, and editing module (bulk liquid culture) 1140. The cells are allowed to grow until the cells reach the stationary growth phase (or nearly so), then editing is induced by induction of transcription of one or both of the nuclease and gRNA. In some embodiments, editing is induced by transcription of one or both of the nuclease and the gRNA being under the control of an inducible promoter. In some embodiments, the inducible promoter is a pL promoter where the promoter is activated by a rise in temperature and "deactivated" by lowering the temperature.

The recovery, selection, growth, induction, editing and storage modules may all be separate, may be arranged and combined as shown in FIG. 11, or may be arranged or combined in other configurations. In certain embodiments, recovery and selection are performed in one module, and growth, editing, and re-growth are performed in a separate module. Alternatively, recovery, selection, growth, editing, and re-growth are performed in a single module.

Once the cells are edited and re-grown (e.g., recovered from editing), the cells may be stored, e.g., in a storage module 1112, where the cells can be kept at, e.g., 4° C. until the cells are retrieved for further study (e.g., cell retrieval 1114). Alternatively, the cells may be used in another round of editing. The multi-module cell processing instrument 1100 is controlled by a processor 1142 configured to operate the instrument based on user input, as directed by one or more scripts, or as a combination of user input or a script. The processor 1142 may control the timing, duration, temperature, and operations of the various modules of the instrument 1100 and the dispensing of reagents. For example, the processor 1142 may cool the cells post-transformation until editing is desired, upon which time the temperature may be raised to a temperature conducive of genome editing and cell growth. The processor may be programmed with standard protocol parameters from which a user may select, a user may specify one or more parameters manually, or one or more scripts associated with the reagent cartridge may specify one or more operations and/or reaction parameters. In addition, the processor may notify the user (e.g., via an application to a smart phone or other device) that the cells have reached the target OD, as well as update the user as to the progress of the cells in the various modules in the multi-module system.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: Growth in the Cell Growth Module

One embodiment of the cell growth device as described herein was tested against a conventional cell shaker shaking a 5 ml tube and an orbital shaker shaking a 125 ml baffled flask to evaluate cell growth in bacterial and yeast cells. Additionally, growth of a bacterial cell culture and a yeast cell culture was monitored in real time using an embodiment of the cell growth device described herein.

In a first example, 20 ml EC23 cells (*E. coli* cells) in LB were grown in a 35 ml rotating growth vial at 30° C. using the cell growth device as described herein. The rotating growth vial was spun at 600 rpm and oscillated (i.e., the rotation direction was changed) every 1 second. OD was measured in the cell growth device. In parallel, 5 ml EC23 cells in LB were grown in an orbital shaker in a 5 ml tube at 30° C. and were shaken at 750 rpm; the $OD_{600}$ was measured at intervals using a NanoDrop™ spectrophotometer (Thermo Fisher Scientific). The rotating growth vial/cell growth device performed better than the cell shaker in growing the cells to $OD_{600}$ 2.6 in slightly over 4 hours (data not shown).

Two additional experiments were performed, this time comparing the rotating growth vial/cell growth device with paddles to a baffled flask and an orbital shaker. In one experiment, 20 ml EC138 cells (*E. coli* cells) in LB were grown in a 35 ml rotating growth vial with a 4-paddle configuration at 30° C. The rotating growth vial was spun at 600 rpm and oscillated (i.e., the rotation direction was changed) every 1 second. In parallel, 20 ml EC138 cells in LB were grown in a 125 ml baffled flask at 30° C. using an orbital shaker. $OD_{600}$ was measured at intervals using a NanoDrop™ spetrophotometer (Thermo Fisher Scientific). The results demonstrated that the rotating growth vial/cell growth device performed as well as the orbital shaker in growing the cells to $OD_{600}$ 1.0. In a second experiment, 20 ml EC138 cells (*E. coli* cells) in LB were grown in a 35 ml rotating growth vial with a 2-paddle configuration at 30° C. using the cell growth device as described herein. The rotating growth vial was spun at 600 rpm and oscillated (i.e., the rotation direction was changed) every 1 second. In parallel, 20 ml EC138 cells in LB were grown in a 125 ml baffled flask at 30° C. using an orbital shaker. $OD_{600}$ was measured at intervals using a NanoDrop™ spectrophotometer (Thermo Fisher Scientific). The results demonstrated that the rotating growth vial/cell growth device performed as well—or better—as the orbital shaker in growing the cells to $OD_{600}$ 1.2.

In yet another experiment, the rotating growth vial/cell growth device was used to measure $OD_{600}$ in real time. The results of real time measurement of growth of an EC138 cell culture at 30° C. using oscillating rotation and employing a 2-paddle rotating growth vial were that $OD_{600}$ 2.6 was reached in 4.4 hours.

In another experiment, the rotating growth vial/cell growth device was used to measure $OD_{600}$ in real time of yeast s288c cells in YPAD. The cells were grown at 30° C. using oscillating rotation and employing a 2-paddle rotating growth vial. For the yeast cells, $OD_{600}$ 6.0 was reached in 14 hours.

Example II: Cell Concentration

The TFF module as described above in relation to FIGS. 6B-6F has been used successfully to process and perform buffer exchange on both *E. coli* and yeast cultures. In concentrating an *E. coli* culture, the following steps were performed:

First, a 20 ml culture of *E. coli* in LB grown to OD 0.5-0.62 was passed through the TFF device in one direction, then passed through the TFF device in the opposite direction. At this point, the cells were concentrated to a volume of approximately 5 ml. Next, 50 ml of 10% glycerol was added to the concentrated cells, and the cells were passed through the TFF device in one direction, in the opposite direction, and back in the first direction for a total of three passes. Again the cells were concentrated to a volume of approximately 5 ml. Again, 50 ml of 10% glycerol was added to the 5 ml of cells and the cells were passed through the TFF device for three passes. This process was repeated; that is, again 50 ml 10% glycerol was added to cells concentrated to 5 ml, and the cells were passed three times through the TFF device. At the end of the third pass of the three 50 ml 10% glycerol washes, the cells were again concentrated to approximately 5 ml of 10% glycerol. The cells were then passed in alternating directions through the TFF device three more times, wherein the cells were concentrated into a volume of approximately 400 µl.

Filtrate conductivity and filter processing time was measured for *E. coli*. Filter performance was quantified by measuring the time and number of filter passes required to obtain a target solution electrical conductivity. Cell retention was determined by comparing the optical density (OD600) of the cell culture both before and after filtration. Filter health was monitored by measuring the transmembrane flow rate during each filter pass. Target conductivity (~16 S/cm) was achieved in approximately 30 minutes utilizing three 50 ml 10% glycerol washes and three passes of the cells through the device for each wash. The volume of the cells was reduced from 20 ml to 400 µl, and recovery of approximately 90% of the cells has been achieved.

The same process was repeated with yeast cell cultures. A yeast culture was initially concentrated to approximately 5 ml using two passes through the TFF device in opposite directions. The cells were washed with 50 ml of 1M sorbitol three times, with three passes through the TFF device after each wash. After the third pass of the cells following the last wash with 1M sorbitol, the cells were passed through the TFF device two times, wherein the yeast cell culture was concentrated to approximately 525 µl. The filter buffer exchange performance for yeast cells was determined by measuring filtrate conductivity and filter processing time. Target conductivity (~10 S/cm) was achieved in approximately 23 minutes utilizing three 50 ml 1M sorbitol washes and three passes through the TFF device for each wash. The volume of the cells was reduced from 20 ml to 525 µl. Recovery of approximately 90% of the cells has been achieved.

Example III: Production and Transformation of Electrocompetent *E. coli* and *S. cerevisiae*

For testing transformation in the FTEP device, electrocompetent *E. coli* cells were created. To create a starter culture, 6 ml volumes of LB chlor-25 (LB with 25 µg/ml chloramphenicol) were transferred to 14 ml culture tubes. A 25 µl aliquot of *E. coli* was used to inoculate the LB chlor-25 tubes. Following inoculation, the tubes were placed at a 450 angle in the shaking incubator set to 250 RPM and 30° C. for overnight growth, between 12-16 hrs. The OD600 value should be between 2.0 and 4.0. A 1:100 inoculum volume of the 250 ml LB chlor-25 tubes were transferred to four sterile 500 ml baffled shake flasks, i.e., 2.5 ml per 250 ml volume shake flask. The flasks were placed in a shaking incubator set to 250 RPM and 30° C. The growth was monitored by measuring OD600 every 1 to 2 hr. When the OD600 of the culture was between 0.5-0.6 (approx. 3-4 hrs), the flasks were removed from the incubator. The cells were centrifuged at 4300 RPM, 10 min, 4° C. The supernatant was removed, and 100 ml of ice-cold 10% glycerol was transferred to each sample. The cells were gently resuspended, and the wash procedure performed three times, each time with the cells resuspended in 10% glycerol. After the fourth centrifugation, the cell resuspension was transferred to a 50 ml conical Falcon tube and additional ice-cold 10% glycerol added to bring the volume up to 30 ml. The cells were again centrifuged at 4300 RPM, 10 min, 4° C., the supernatant removed, and the cell pellet resuspended in 10 ml ice-cold glycerol. The cells are aliquoted in 1:100 dilutions of cell suspension and ice-cold glycerol.

For further testing transformation of the FTEP device, S. Cerevisiae cells were created using the methods as generally set forth in Bergkessel and Guthrie, Methods Enzymol., 529:311-20 (2013). Briefly, YPD or YPAD media was inoculated for overnight growth from colonies on a YP+glycerol agar plate to produce 150 mL of cells. The following morning, the overnight culture was diluted to an OD600 of approximately 0.3. Cells were incubated at 30° C. in a shaking incubator until they reached an OD600 of 1.5+/−0.1.

A conditioning buffer was prepared using 100 mM lithium acetate and 10 mM dithiothreitol. A total of 100 mL of buffer were prepared for every 100 mL of cells grown. Cells were harvested in 250 mL bottles by centrifugation at 4300 rpm for 6 minutes, and the supernatant removed. The cells were suspended in conditioning buffer, then the suspension transferred into an appropriate flask and shaken at 200 RPM and 30° C. for 30 minutes. The suspension was transferred to 250 mL bottles and spun at 4300 rpm for 6 minutes. The supernatant was removed and the pellets resuspended in cold 1 M sorbitol. These steps were repeated three times for a total of three wash-spin-decant steps. The pellet was suspended in sorbitol so that 20 mL of OD 1.5 culture were resuspended in 500 µL. For each 500 µL volume of resuspended cells, a 100 µL volume containing DNA and Tween80 was added to the cell suspension.

Figure 12A:
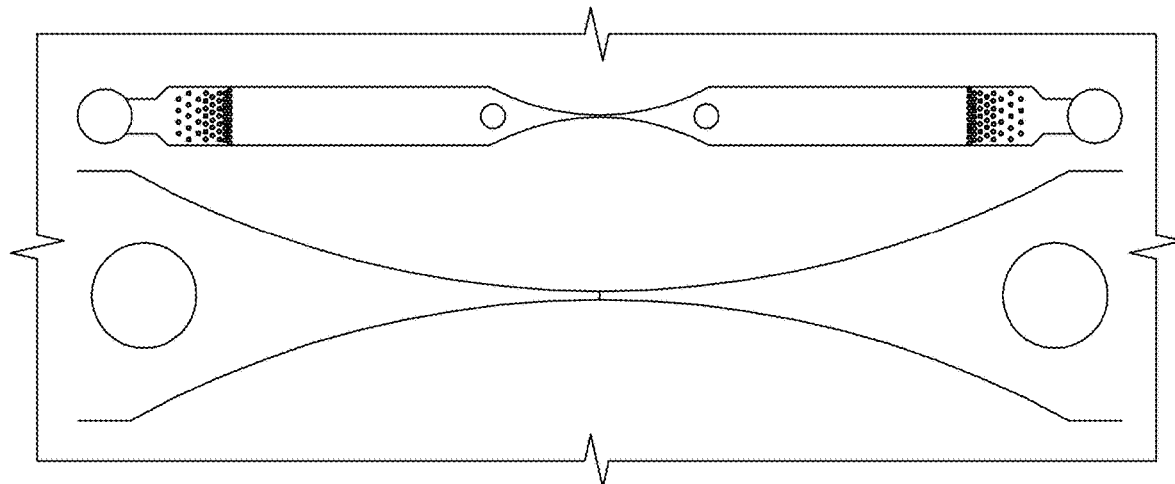
FIG. 12A depicts an FTEP with a constricted flow channel with obstructions at the ends of the flow channel proximate to the inlet and outlet (at right), and an obstruction array as described herein (at left).
Figure 12A:
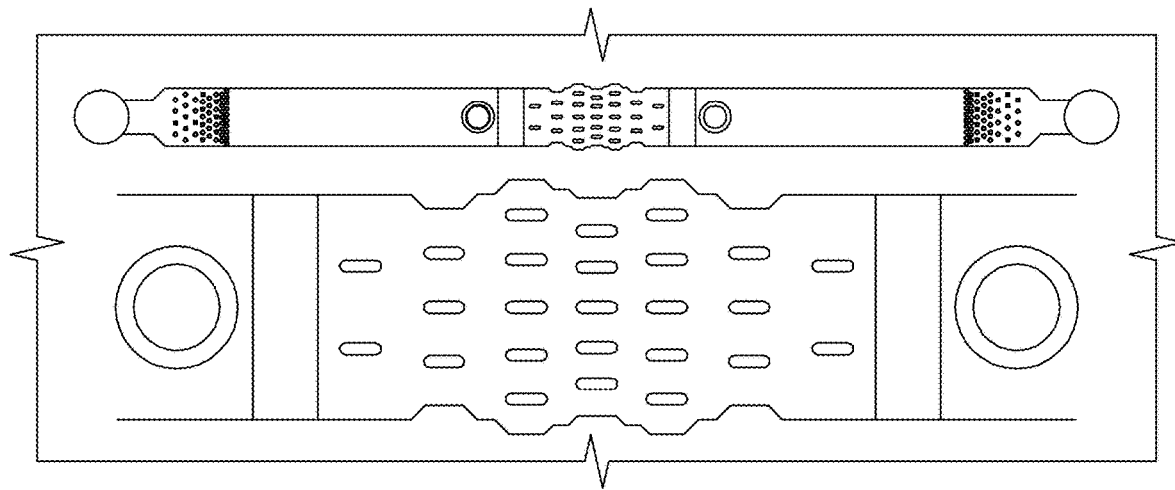

A comparative electroporation experiment was performed to determine the efficiency of transformation of electrocompetent S. cerevisiae and E. coli using the obstruction array FTEP device described, benchmarked against a NEPA electroporation device and a single constriction FTEP. See FIG. 12A for a comparison of the single constriction FTEP device and the obstruction array FTEP device. In the obstruction array FTEP device tested, ramps in the central region (one before and one after the array moving from the inlet proximal region of the flow channel toward the outlet proximal region of the flow channel) decreases the channel height from 100 µm near the electrode channels to 50 µm at the obstruction. The flow rate was controlled with a pressure control system, and the performance of the obstruction array FTEP device was tested at various voltages and pressures. The suspension of cells with DNA was loaded into the FTEP inlet reservoir. The transformed cells flowed directly from the inlet and inlet channel, through the flow channel, through the outlet channel, and into the outlet. The cells were transferred into a tube containing additional recovery medium and placed in an incubator shaker at 30° C. shaking at 250 rpm for 3 hours. The cells were plated to determine the colony forming units (CFUs) that survived electroporation and the CFUs that survived electroporation and took up a plasmid. Plates were incubated at 30° C.; E. coli colonies were counted after approximately 24 hrs.

Figure 12B:
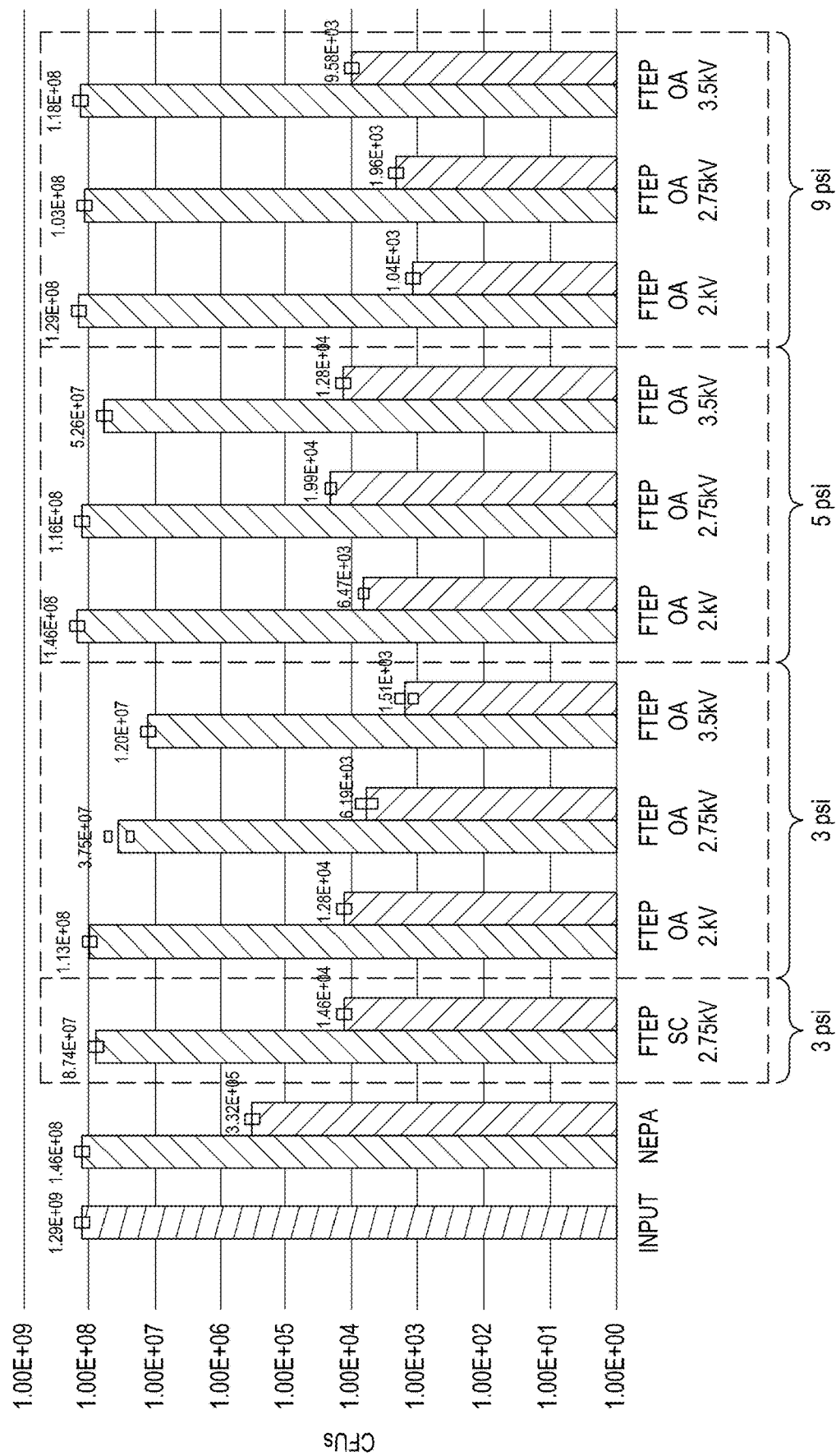
FIG. 12B-12D are bar graphs depicting the number of cells that were input (far left bar), the number of cells that survived electroporation (left bar for each datapoint), and the number of cells that were transformed (right bar for each datapoint) at varying kV and pressures. The obstruction arrays described herein were benchmarked against a NEPA device and a single constriction device.
Figure 12C:
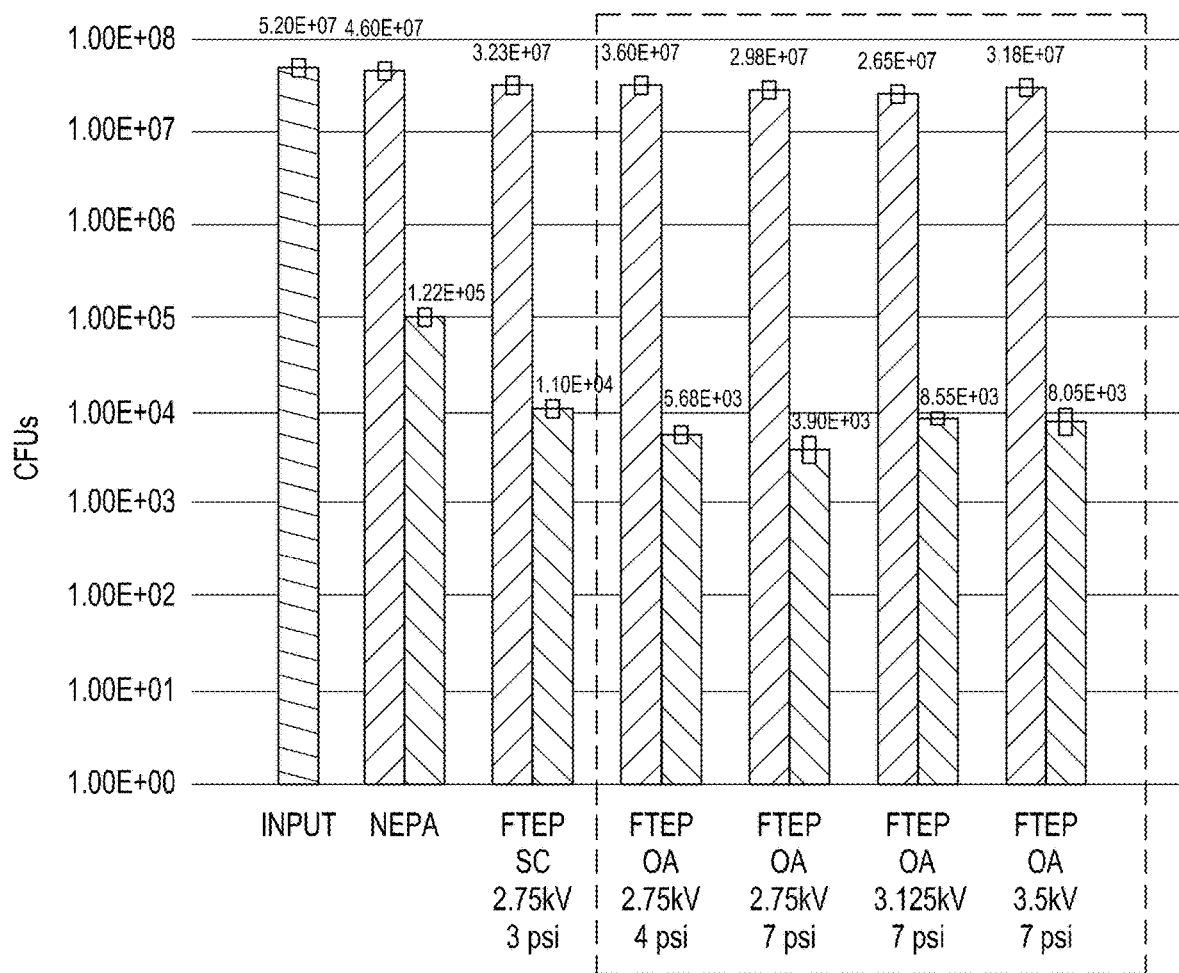
Figure 12D:
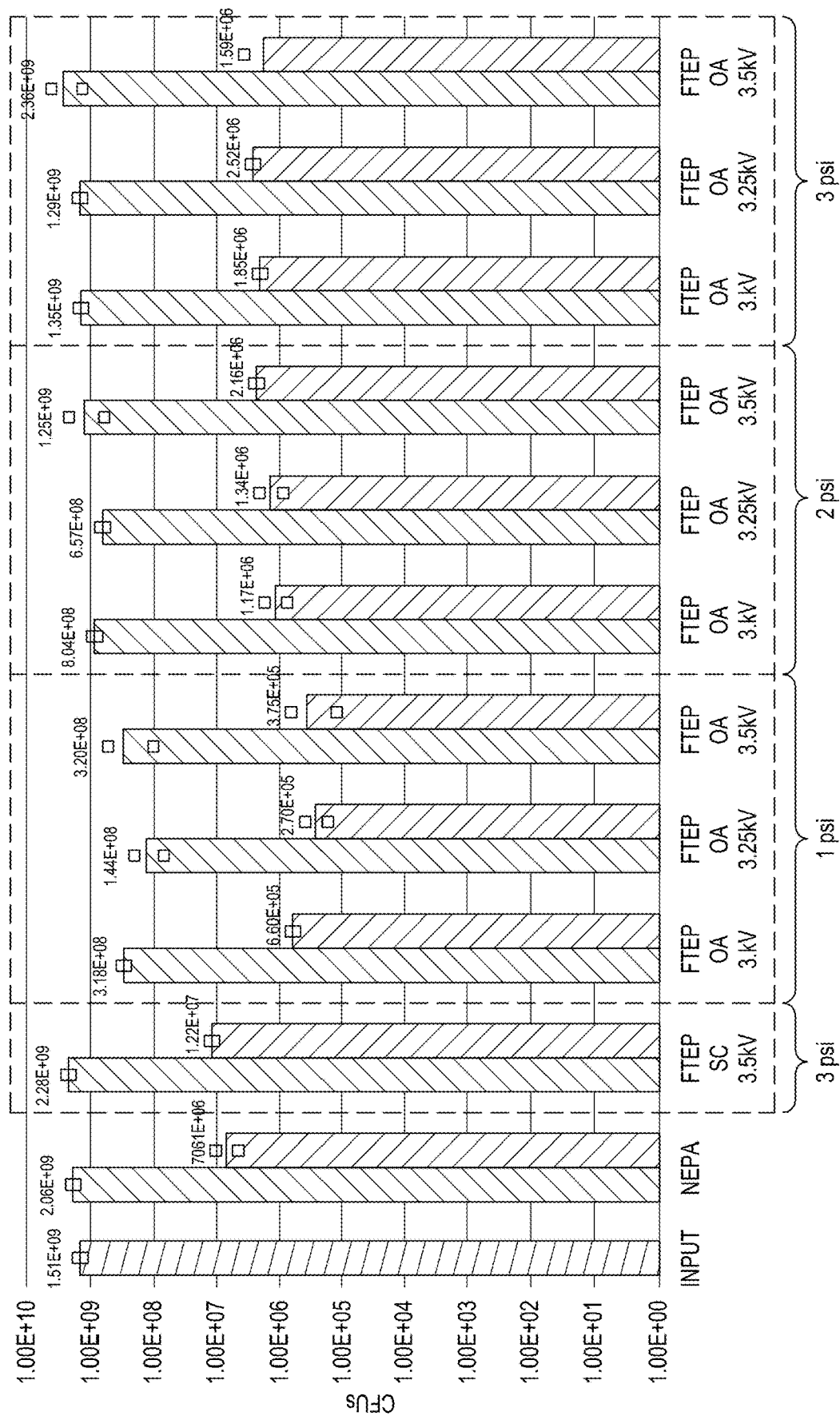

FIG. 12B shows data revealing that the obstruction array FTEP device demonstrated equivalent uptake of DNA by S. cerevisiae as compared to the single constriction FTEP device and a NEPA (cuvette) device. The single left-most bar indicates the cell input for each datapoint. For each datapoint, the left bar indicates the number of cells that survived electroporation, and the right bar indicates the number of cells that were transformed with the DNA. Replicates were performed for each datapoint and the bars are the means of the duplicates. FIG. 12C shows data revealing that a different obstruction array FTEP device with a minimum flow path width of 100 µm and minimum height of 50 µm demonstrated uptake of DNA by S. cerevisiae within a factor of 1.3 as compared to the single constriction FTEP device. The single left-most bar indicates the cell input for each datapoint. For each datapoint, the left bar indicates the number of cells that survived electroporation, and the right bar indicates the number of cells that were transformed with the DNA. Replicates were performed for each datapoint and the bars are the means of the duplicates. FIG. 12D shows data revealing that an obstruction array FTEP device with a minimum flow path width of 40 µm and a minimum height of 50 µm demonstrated uptake of DNA by E. coli within a factor of 5 as compared to the single constriction FTEP device and a NEPA (cuvette) device. The single left-most bar indicates the cell input for each datapoint. For each datapoint, the left bar indicates the number of cells that survived electroporation (bars with angled lines from bottom left to top right), and the right bar indicates the number of cells that were transformed with the editing plasmid (i.e., uptake) (bars with angled lines from top left to bottom right). Replicates were performed for each datapoint and the bars are the means of the duplicates.

Example IV: Optimization of FTEP Configuration

Figure 13:
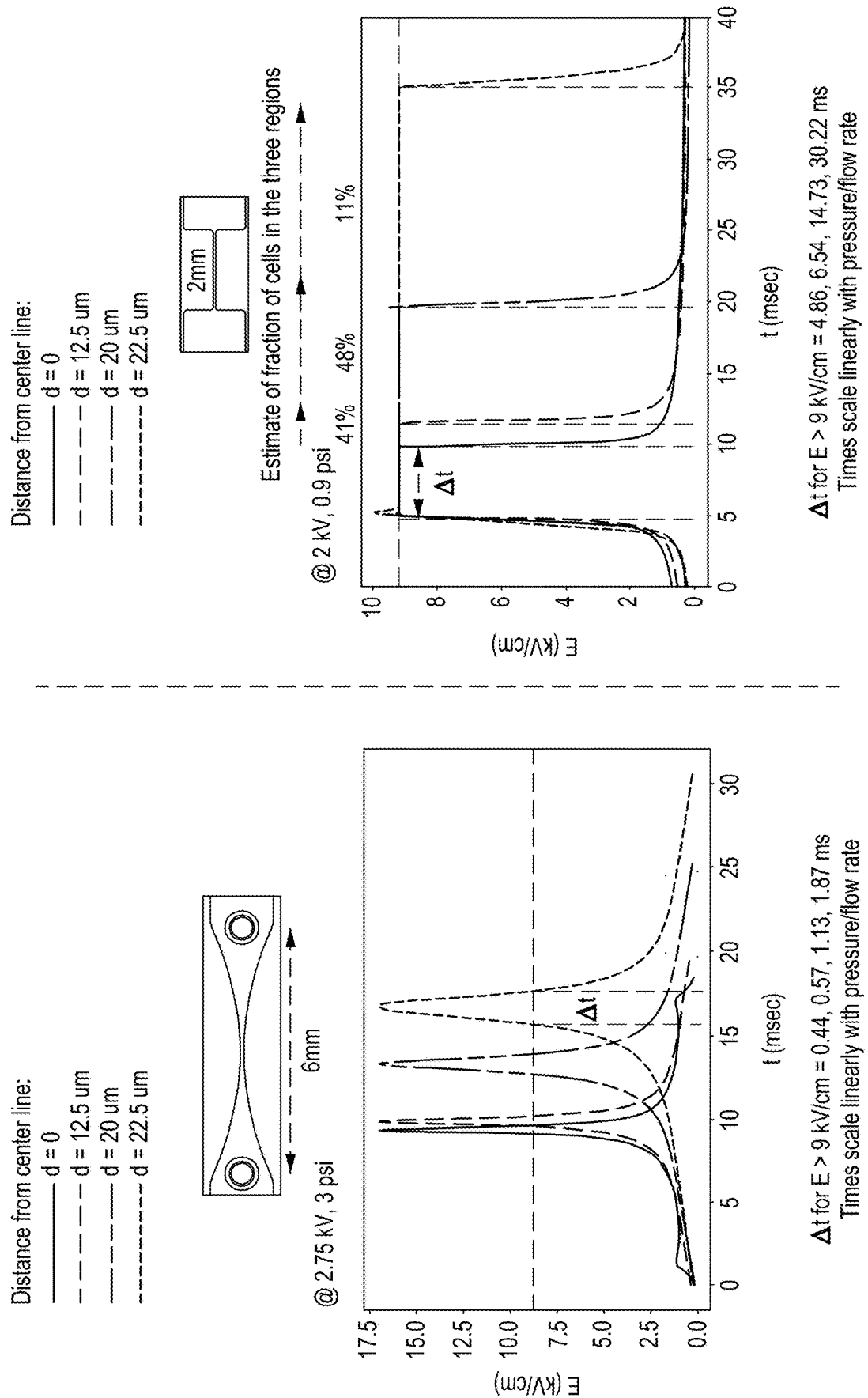
FIG. 13 shows two graphs, at left shows simulated electric field strength experienced by cells vs. time for cells passing through a single constriction FTEP (such as shown in FIG. 12A, top) and at right shows simulated electric field strength experienced by cells vs. time for cells passing through a parallel-constriction FTEP (such as shown in FIGS. 1M and 1N).

For optimizing transformation in the parallel-obstruction FTEP device embodiment shown in FIG. 1L-1N, electrocompetent S288c cells were created. FIG. 13 shows at left a plot of simulated electric field strength vs. residence time for the "hour glass"-shaped FTEP embodiment pictured above the plot (conducted at 2.75 kV, 3 psi). The plot shows the energy electric field strength (kV/cm) experienced by cells at d=0 (at the center of the FTEP device), d=12.5 µm (from the center), d=20 µm (from the center), and d=22.5 µm (from the center). The dotted line at approximately 9 kV/cm shows the electric field strength experienced by cells porated in a Nepa Gene cuvette. Note that in the "hour glass" FTEP configuration, the cells experience a spike in electric field strength significantly above that experienced in a cuvette. FIG. 13 at right shows a plot of simulated electric field strength vs. residence time for the "abrupt step" FTEP embodiment shown above the plot (conducted at 2.0 kV, 0.9 psi). Note that with this embodiment of an FTEP, it is possible to control the magnitude of a constant electric field strength experienced by the cells. Again, the plot shows the electric field strength E (kV/cm) experienced by cells at d=0 (at the center of the FTEP device), d=12.5 µm (from the center), d=20 µm (from the center), and d=22.5 µm (from the center). The dotted line at approximately 9 kV/cm shows the electric field strength experienced by cells porated in a NepaGene cuvette.

Figure 14:
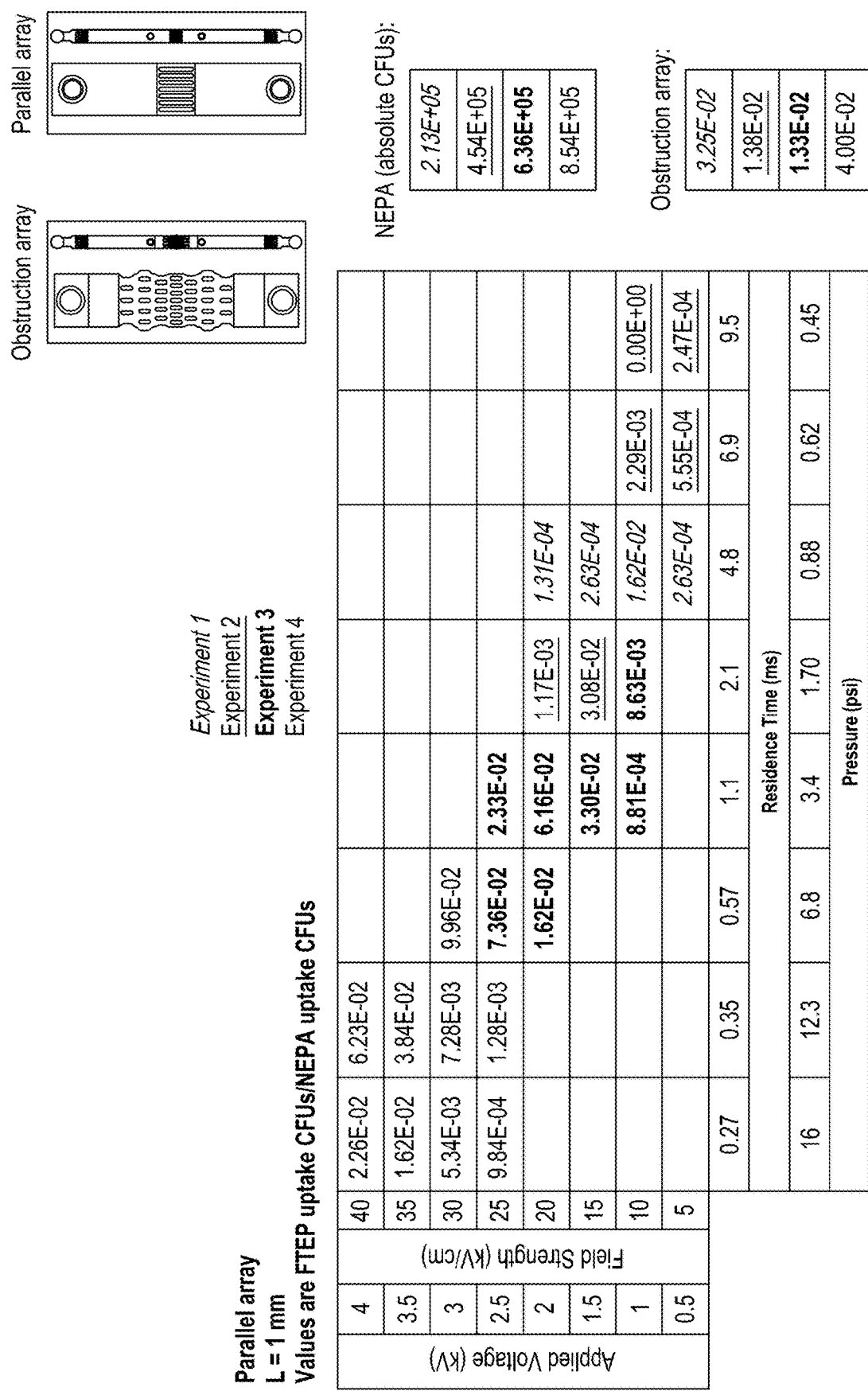
FIG. 14 shows the results of electric field strength and residence time sweeps for the parallel-constriction FTEP as shown in FIG. 1L-1N where the obstructions in the center region define a 1 mm length, which confirms optimal uptake at 6.8 psi, 3 kV.

FIG. 14 shows the results of a sweep of various electric field strengths and residence times with S288c, achieved by varying the applied voltage and pressure, for the parallel-obstruction FTEP embodiment shown in FIG. 1L-1N. The right plot of FIG. 13 demonstrates that the "abrupt step" configuration of FTEP allows for control over the magnitude of a constant electric field strength experienced by cells in the FTEP device; however, though the "abrupt step" configuration allows for control of field strength, the configuration of a single "abrupt step" can lead to clogging of the flow channel, which in turn leads to catastrophic failure of the FTEP device. To decrease the likelihood of clogging while still maintaining a channel configuration that allows tuning of field strength and residence time, the parallel-obstruction FTEP embodiment shown in FIG. 1L-1N was tested. In this embodiment, the obstructions are elongated ovals (1.0 mm in length) which form 8 parallel "lanes" in the center region of the flow channel. Note that for the 1.0 mm-long center obstruction configuration the optimal applied voltage was 3 kV with an applied pressure of 6.8 psi, leading to an uptake value of 8.51E+04 CFUs.

Figure 15:
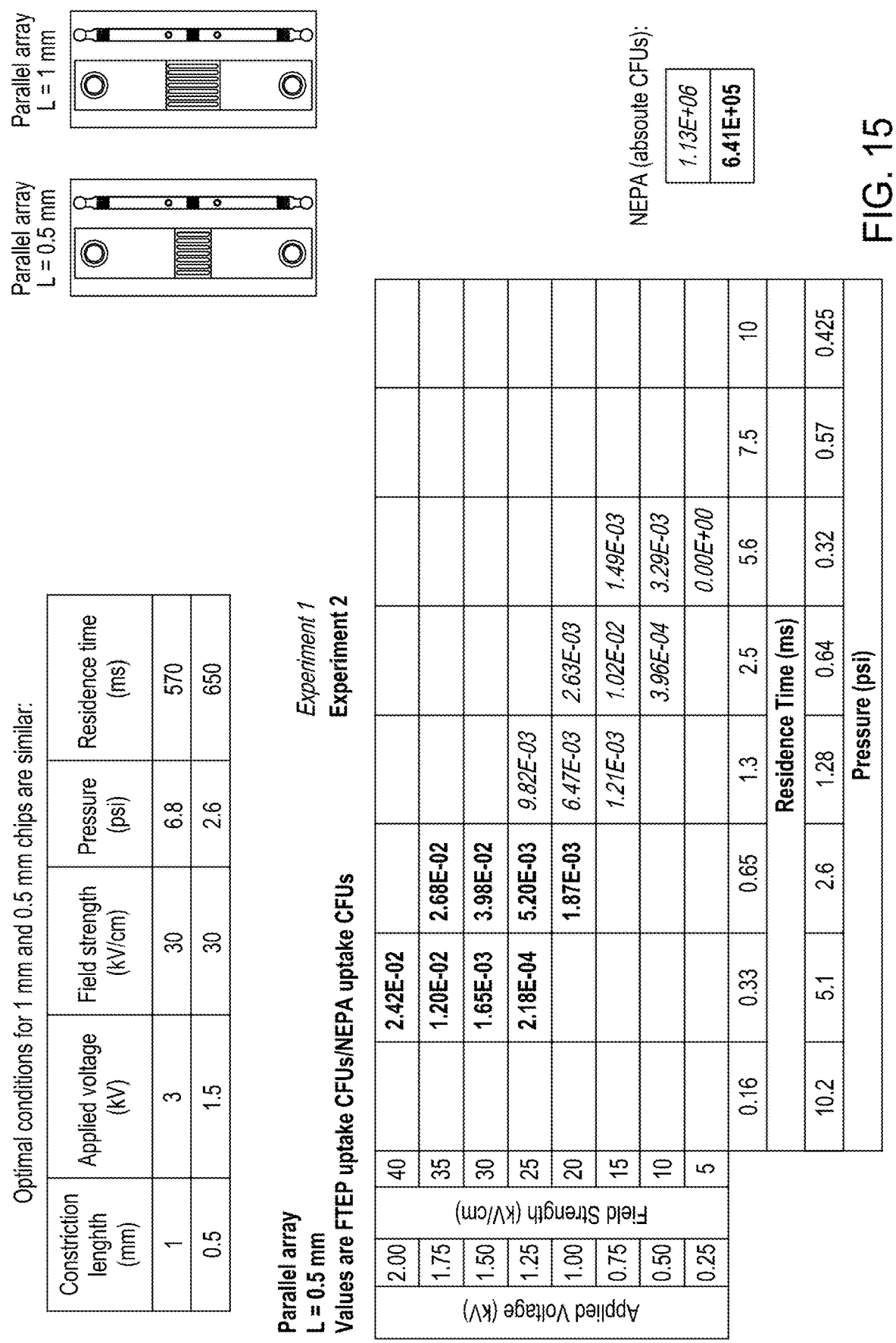
FIG. 15 shows the results of electric field strength and residence time sweeps for the parallel-constriction FTEP as shown in FIG. 1L-1N where the obstructions in the center region define a 0.5 mm length. Note that the parallel-constriction FTEP allows one to control the magnitude of a constant, high electric field strength and the amount of time cells are exposed to the electric field by simply adjusting the applied voltage and pressure.

FIG. 15 shows at top the results of a sweep of various electric field strengths and residence times with S288c, achieved by varying the applied voltage and pressure, for the parallel-obstruction FTEP embodiment shown in FIG. 1L-1N. In this embodiment, the obstructions are elongated ovals that are 0.5 mm in length, which form 8 parallel "lanes" in the center region of the flow channel. Note that the optimal applied voltage was 1.5 kV with an applied pressure of 2.6 psi, leading to an uptake value of 2.55E+04 CFUs. At top shows a comparison between the parallel-obstruction FTEP embodiment shown in FIG. 1L-1N with 1.0 mm-long obstructions vs. 0.5 mm-long obstructions. Note that the magnitude of a constant electric field strength and residence time within the electric field can be controlled in this embodiment FTEP by adjusting the applied voltage and pressure.

Example V: Fully-Automated Singleplex RGN-Directed Editing Run

Singleplex automated genomic editing using MAD7 nuclease was successfully performed with an automated multi-module instrument of the disclosure. See U.S. Pat. No. 9,982,279; and U.S. Ser. No. 16/024,831 filed 30 Jun. 2018; Ser. No. 16/024,816 filed 30 Jun. 2018; Ser. No. 16/147,353 filed 28 Sep. 2018; Ser. No. 16/147,865 filed 30 Sep. 2018; and Ser. No. 16/147,871 filed 30 Jun. 2018.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent E. Coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example VI: Fully-Automated Recursive Editing Run

Recursive editing was successfully achieved using the automated multi-module cell processing instrument. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent E. coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in the isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. Coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing instrument.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A flow-through electroporation (FTEP) device for introducing an exogenous material into cells in a fluid, the FTEP device comprising:
   a. an inlet and an inlet channel for receiving a fluid comprising cells and/or exogenous material into the FTEP device;
   b. an outlet and an outlet channel for removing a fluid comprising transformed cells and exogenous material from the FTEP device;
   c. a flow channel intersecting and positioned between the inlet channel and the outlet channel, wherein the flow channel has, moving from the inlet channel toward the outlet channel, an inlet-filter region, an inlet-proximal region, a central region, an outlet-proximal region, and an outlet-filter region;
   d. an inlet filter comprising filter elements disposed in the inlet-filter region of the flow channel and an outlet filter comprising filter elements disposed in the outlet-filter region of the flow channel;
   e. a plurality of parallel-configured obstructions defining flow lanes disposed within the central region of the flow channel; and
   f. a first and a second electrode positioned in electrode channels, wherein the first electrode is positioned in the inlet proximal region of the flow channel and the second electrode is positioned in the outlet proximal region of the flow channel; wherein the electrodes are positioned perpendicularly to the flow channel, are in fluid and electrical communication with fluid in the flow channel, wherein the electrodes apply one or more electric pulses to the cells in the fluid as they pass through the flow channel, thereby introducing exogenous material into the cells in the fluid, and wherein the device is formed by injection molding in one piece with the exception of the electrodes.

2. The FTEP device of claim 1, wherein there are three or more parallel-configured obstructions.

3. The FTEP device of claim 1, wherein the parallel-configured obstructions are elongated oval-shaped.

4. The FTEP device of claim 3, wherein the FTEP device comprises a second inlet and a second inlet channel and further comprising a reservoir coupled to the second inlet for introducing exogenous material into the FTEP device.

5. The FTEP device of claim 4, wherein the second inlet and second inlet channel are located between the inlet channel and the first electrode.

6. The FTEP device of claim 4, wherein the second inlet and second inlet channel are located between the second electrode and the outlet channel.

7. The FTEP device of claim 1, further comprising a reservoir coupled to the inlet for introducing the cells in fluid into the FTEP device and a reservoir coupled to the outlet for removing transformed cells from the FTEP device.

8. The FTEP device of claim 1, wherein device is configured for use with bacterial, yeast and mammalian cells.

9. The FTEP device of claim 1, wherein the number of obstructions in the central region of the flow channel is from 3 to 15.

10. The FTEP device of claim 9, wherein the narrowest flow path between obstructions is from 30 to 250 µm wide.

11. The FTEP device of claim 1, wherein the narrowest flow path between obstructions is from 10 to 350 µm wide.

12. The FTEP device of claim 1, wherein the electrodes supply a voltage of 1-60 kV/cm.

13. The FTEP device of claim 12, wherein the electrodes supply a voltage of 5-40 kV/cm.

14. The FTEP device of claim 1, wherein the flow through the FTEP device is from 0.01 mL/min to 7.5 mL/min.

15. The FTEP device of claim 1, wherein the pressure in the FTEP is from 1-30 psi.

16. The FTEP device of claim 15, wherein the pressure in the FTEP is from 2-10 psi.

17. The FTEP device of claim 1, wherein the FTEP is from 3-15 cm long.

18. The FTEP device of claim 1, wherein the FTEP is from 0.5 to 5 cm wide.

19. The FTEP device of claim 1, further comprising a ramp in the central region proximal to the inlet-proximal region of the flow channel to a central portion of the central region decreasing the flow channel height, and a ramp from the central portion of the central region to the central region proximal to the outlet-proximal region of the flow channel increasing the flow channel height.

* * * * *